US009273288B2

(12) United States Patent
Mason et al.

(10) Patent No.: US 9,273,288 B2
(45) **Date of Patent: *Mar. 1, 2016**

(54) PSEUDOINFECTIOUS FLAVIVIRUS AND USES THEREOF

(75) Inventors: Peter W. Mason, Galveston, TX (US); Elena Frolova, Galveston, TX (US); Ilya Frolov, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 647 days.

This patent is subject to a terminal disclaimer.

(21) Appl. No.: 13/561,002

(22) Filed: Jul. 28, 2012

(65) Prior Publication Data

US 2013/0023031 A1 Jan. 24, 2013

Related U.S. Application Data

(63) Continuation of application No. 11/711,532, filed on Feb. 27, 2007, now Pat. No. 8,252,574.

(60) Provisional application No. 60/777,189, filed on Feb. 27, 2006.

(51) Int. Cl.
*C12N 7/00* (2006.01)
*A61K 39/12* (2006.01)
*A61K 39/00* (2006.01)

(52) U.S. Cl.
CPC . *C12N 7/00* (2013.01); *A61K 39/12* (2013.01); *A61K 2039/5254* (2013.01); *C12N 2770/24134* (2013.01); *C12N 2770/24162* (2013.01)

(58) Field of Classification Search
CPC ........... C12N 7/00; C12N 2770/24162; C12N 2770/24134; A61K 2039/5254; A61K 39/12
See application file for complete search history.

(56) References Cited

U.S. PATENT DOCUMENTS

| | | | |
|---|---|---|---|
| 8,252,574 | B2 | 8/2012 | Mason et al. |
| 2004/0052818 | A1 | 3/2004 | Heinz et al. |
| 2004/0235133 | A1 | 11/2004 | Frolov et al. |
| 2006/0018928 | A1 | 1/2006 | Pang |
| 2007/0249032 | A1 | 10/2007 | Pang et al. |

FOREIGN PATENT DOCUMENTS

| | | | |
|---|---|---|---|
| WO | WO/99/28487 | A1 | 6/1999 |
| WO | WO/00/14245 | A1 | 3/2000 |
| WO | WO/00/55378 | A1 | 9/2000 |
| WO | WO 02/72803 | A2 | 2/2002 |
| WO | WO/03/046189 | A1 | 6/2003 |
| WO | WO/2004/016794 | A1 | 2/2004 |
| WO | WO/2004/022761 | A1 | 3/2004 |
| WO | WO/2004/108936 | A1 | 12/2004 |
| WO | WO 2006/017206 | A2 | 2/2006 |

OTHER PUBLICATIONS

Harvey, T. et al. "Tetracycline-Inducible Packaging Cell Line for Production of Flavivirus Replicon Particles". Journal of Virology, 78 (1), 2004.
Jones, C. et al. "Flavivirus Capsid is a Dimeric Alpha-Helical Protein". Journal of Virology, 77(12), 2003.
Kofler, R. "Mimicking Live Flavivirus Immunization with a Noninfectious RNA Vaccine". Proceedings of the National Academy of Sciences, 101 (7), 2004, 1951-1956.
Kofler, R. "Spontaneous Mutations Restore the Viability of Tick-Borne Encephalitis Virus Mutants with Large Deletions in Protein C". Journal of Virology, 77(1), 2003.
Mandl, C. "Flavivirus Immunization with Capsid-Deletion Mutants: Basics, Benefits, and Barriers". Viral Immunology, 17(4), 2004.
Aberle et al. Humoral and cellular immune response to RNA immunization with flavivirus replicons derived from tick-borne encephalitis virus. Journal of Virology 79(24), 15107-13 (2005).
Dudek, T. and Knipe, D. Replication-defective viruses as vaccines and vaccine vectors. Virology 344, 230-239 (2006).
Harvey et al. Kunjin Virus Replicon Vectors for Human Immunodeficiency Virus Vaccine Development. Journal of Virology 77(14), 7796 (2003).
Harvey et al. Tetracycline-inducible packaging cell line for production of flavivirus replicon particles. Journal of Virology 78(1), 531-8 (2004).
Jones, C. et al. "Flavivirus Capsid is a Dimeric Alpha-Helical Protein". Journal of Virology, 77(12), 7143-7149 (2003).
Kofler, R. Capsid Protein C of Tick-Borne Encephalitis Virus Tolerates Large Internal Deletions and is a Favorable Target for Attenuation of Virulence. Journal of Virology 76(7), 3534-3543 (2002).
Kofler, R. Spontaneous mutations restore the viability of tick-borne encephalitis virus mutants with large deletions in protein C. Journal of Virology 77(1), 443-451 (2003).
Kofler, R. Mimicking Live Flavivirus Immunization with a Noninfectious RNA Vaccine. Proceedings of the National Academy of Sciences, 101 (7), 1951-1956 (2004).
Mandl, C. Flavivirus Immunization with Capsid-Deletion Mutants: Basics, Benefits, and Barriers. Viral Immunology, 17(4), 461-472 (2004).
Mason et al. Production and characterization of vaccines based on flaviviruses defective in replication. Virology 351, 432-443 (2006).
Scholle et al. Particles: trans-Packaged West Nile Virus-Like Particles: Infectious Properties in Vitro and in Infected Mosquito Vectors. Journal of Virology 78(21), 11605-14 (2004).

(Continued)

*Primary Examiner* — Stacy B Chen
(74) *Attorney, Agent, or Firm* — Norton Rose Fulbright US LLP

(57) ABSTRACT

The present invention discloses a replication-deficient pseudoinfective virus belonging to the Flaviviridae family that lack the capsid gene, where the replication-deficient pseudoinfective virus propagates only in cells expressing the capsid or capsid, prM and envelope protein of the flavivirus. The present also discloses the method of producing such viruses on a large scale and the use of these pseudoinfective viruses as vaccines for preventing diseases caused by infections of humans or animals by the viruses belonging to this family.

24 Claims, 29 Drawing Sheets

(56) References Cited

OTHER PUBLICATIONS

Shustov et al. Production of Pseudoinfectious Yellow Fever Virus with a Two-Component Genome. Journal of Virology 81(21), 11737-11748 (2007).

Wagner et al. Rev-Independent Expression of Synthetic gag-pol Genes of Human Immunodeficiency Virus Type 1 and Simian Immunodeficiency Virus: Implications for the Safety of Lentiviral Vectors. Human Gene Therapy 11, 2403-2413 (2000).

Widman et al. Third-Generation Flavivirus Vaccines Based on Single-Cycle, Encapsidation-Defective Viruses. Advances in Virus Research 72, 77-126 (2008).

Fig.2A

YFV genome: C | prM | E | NS1 | 2A | 2B | NS3 | 4A | 4B | NS5

YF PIV genome: GFP | prM | E | NS1 | 2A | 2B | NS3 | 4A | 4B | NS5

Fig.2B

VEErep/C1/Pac: nsP1 | nsP2 | nsP3 | nsP4 | C | Pac

VEErep/C2/Pac: nsP1 | nsP2 | nsP3 | nsP4 | C | Pac

VEErep/C-prM-E/Pac: nsP1 | nsP2 | nsP3 | nsP4 | C | prM | E | Pac

Fig.2C

Release of YF PIV (inf.u/ml) vs Days post transfection

□ VEErep/C1/Pac
○ VEErep/C2/Pac
△ VEErep/C-prM-E/Pac

ATGagcGgcCGgaAGgGTCAGGgcaAgaGACCCTgGGCGTgaGgCGcGgcGTgCGcAAcAAg
ATcAAgCAgaAAgaCCaAgCAgaTcGgaGAAGaCCcGagcGAGaGccCGCaGGaGTtCATCTTccTG
TTcAACATcCTcAGagCtAAgaAGaTGcGgGTGcGccGAAgATGCTGGAAgAGCGCtgaCACCTTgaGGgCTc
GCgTgCTcAGaAAgTgAAgcGggTGcGcTGcGcctcccTGTCCTTcGcAAgaGgCGcTCCCACGAT
GTgCTcAcCgTccAATTCCTcATTcTGGGAATGcGccGGcCTGGGCGGCTGACCTGgcGCGTCGCGG
cTGCTgCTgaATGTgACcagTGAGGACCTCGGG    SEQ ID NO: 1

Fig. 6C gagtaaatcctgtgtgctaattgaggtgcattggtctgcaaatcgagttgctaggcaataaacacatttggattaattttaatcgt
tcgttgagcgattagcagagaactgaccagaacatgtctggtcgtaaagctcagggaaaaaccctgggcgtcaatatggt
acgacgaggagttcgctccttgtcaaacaccatggtgagcaagggcgaggagctgttcaccggggtggtgcccatcctgg
tcgagctggacggcgacgtaaacggccacaagttcagcgtgtccggcgagggcgagggcgatgccacctacggcaag
ctgaccctgaagttcatctgcaccaccggcaagctgcccgtgccctggcccaccctcgtgaccaccctgacctacggcgtg
cagtgcttcagccgctaccccgaccacatgaagcagcacgacttcttcaagtccgccatgcccgaaggctacgtccagga
gcgcaccatcttcttcaaggacgacggcaactacaagacccgcgccgaggtgaagttcgagggcgacaccctggtgaa
ccgcatcgagctgaagggcatcgacttcaaggaggacggcaacatcctggggcacaagctggagtacaactacaaca
gccacaacgtctatatcatggccgacaagcagaagaacggcatcaaggtgaacttcaagatccgccacaacatcgagg
acggcagcgtgcagctcgccgaccactaccagcagaacacccccatcggcgacggccccgtgctgctgcccgacaac
cactacctgagcacccagtccgccctgagcaaagaccccaacgagaagcgcgatcacatggtcctgctggagttcgtga
ccgccgccgggatcactctcggcatggacgagctgtacaagcttggattgtcctcaaggaaacgccgttcccatgatgttct
gactgtgcaattcctaattttgggaatgctgttgatgacgggtggagtgaccttggtgcggaaaaacagatggttgctcctaa
atgtgacatctgaggacctcgggaaaacattctctgtgggcacaggcaactgcacaacaaacattttggaagccaagtact
ggtgcccagactcaatggaatacaactgtcccaatctcagtccaagagaggagccagatgacattgattgctggtgctatg
gggtggaaaacgttagagtcgcatatggtaagtgtgactcagcaggcaggtctaggaggtcaagaagggccattgacttg
cctacgcatgaaaaccatggtttgaagacccggcaagaaaaatggatgactggaagaatgggtgaaaggcaactccaa
aagattgagagatggttcgtgaggaaccccttttttgcagtgacggctctgaccattgcctaccttgtgggaagcaacatgac
gcaacgagtcgtgattgccctactggtcttggctgttggtccggcctactcagctcactgcattggaattactgacagggatttc
attgaggggtgcatggaggaacttgggtttcagctaccctggagcaagacaagtgtgtcactgttatggcccctgacaag
ccttcattggacatctcactagagacagtagccattgatagacctgctgaggtgaggaaagtgtgttacaatgcagttctcac
tcatgtgaagattaatgacaagtgccccagcactggagaggcccacctagctgaagagaacgaaggggacaatgcgtg
caagcgcacttattctgatagaggctggggcaatggctgtggcctatttgggaaagggagcattgtggcatgcgccaaattc
acttgtgccaaatccatgagtttgtttgaggttgatcagaccaaaattcagtatgtcatcagagcacaattgcatgtaggggcc
aagcaggaaaattggaataccgacattaagactctcaagtttgatgccctgtcaggctcccaggaagtcgagttcattgggt
atggaaaagctacactggaatgccaggtgcaaactgcggtggactttggtaacagttacatcgctgagatggaaacagag
agctggatagtggacagacagtgggcccaggacttgaccctgccatggcagagtggaagtggcggggtgtggagagag
atgcatcatcttgtcgaatttgaacctccgcatgccgccactatcagagtactggccctgggaaaccaggaaggctccttga
aaacagctcttactggcgcaatgaggggttacaaaggacacaaatgacaacaaccttacaaactacatggtggacatgttt
cttgcagagtgaaattgtcagctttgacactcaaggggacatcctacaaaatatgcactgacaaaatgttttttgtcaagaac
ccaactgacactggccatggcactgttgtgatgcaggtgaaagtgtcaaaaggagcccccctgcaggattccagtgatagta
gctgatgatcttacagcggcaatcaataaaggcattttggttacagttaaccccatcgcctcaaccaatgatgatgaagtgct
gattgaggtgaacccaccttttggagacagctacattatcgttgggagaggagattcacgtctcacttaccagtggcacaaa
gagggaagctcaataggaaagttgttcactcagaccatgaaaggcgtggaacgcctggccgtcatgggagacaccgcct
gggatttcagctccgctggagggttcttcacttcggttgggaaaggaattcatacggtgtttggctctgcctttcaggggctattt
ggcggcttgaactggataacaaaggtcatcatggggggcggtacttatatgggttggcatcaacacaagaaacatgacaat
gtccatgagcatgatcttggtaggagtgatcatgatgttttgtctctaggagttggggcggatcaaggatgcgccatcaacttt
ggcaagagagagctcaagtgcggagatggtatcttcatatttagagactctgatgactggctgaacaagtactcatactatc
cagaagatcctgtgaagcttgcatcaatagtgaaagcctcttttgaagaagggaagtgtggcctaaattcagttgactccctt
gagcatgagatgtggagaagcagggcagatgagatcaatgccatttttgaggaaaacgaggtggacatttctgttgtcgtg
caggatccaaagaatgtttaccagagaggaactcatccattttccagaattcgggatggtctgcagtatggttggaagacttg
gggtaagaaccttgtgttctccccagggaggaagaatggaagcttcatcatagatggaaagtccaggaaagaatgcccgt
tttcaaaccgggtctggaattctttccagatagaggagtttgggacgggagtgttcaccacacgcgtgtacatggacgcagt
ctttgaatacaccatagactgcgatggatctatcttgggtgcagcggtgaacggaaaaaagagtgcccatggctctccaac
attttggatgggaagtcatgaagtaaatgggacatggatgatccacaccttggaggcattagattacaaggagtgtgagtgg
ccactgacacatacgattggaacatcagttgaagagagtgaaatgttcatgccgagatcaatcggaggcccagttagctct
cacaatcatatccctggatacaaggttcagacgaacggaccttggatgcaggtaccactagaagtgaagagagaagctt
gcccagggactagcgtgatcattgatggcaactgtgatggacggggaaaatcaaccagatccaccacggatagcggga
aagttattcctgaatggtgttgccgctcctgcacaatgccgcctgtgagcttccatggtagtgatgggtgttggtatcccatgga
aattaggccaaggaaaacgcatgaaagccatctggtgcgctcctgggttacagctggagaaatacatgctgtcccttttggt ttggtgagcatgatgatagcaatggaagtggtcctaaggaaaagacagggaccaaagcaaatgttggttggaggagtag
tgctcttgggagcaatgctggtcgggcaagtaactctccttgatttgctgaaactcacagtggctgtgggattgcatttccatga
gatgaacaatggaggagacgccatgtatatggcgttgattgctgccttttcaatcagaccagggctgctcatcggctttgggc
tcaggaccctatggagccctcggggaacgccttgtgctgaccctaggagcagccatggtggagattgccttgggtggcgtga
tgggcggcctgtggaagtatctaaatgcagtttctctctgcatcctgacaataaatgctgttgcttctaggaaagcatcaaata
ccatcttgccccctcatggctctgttgacacctgtcactatggctgaggtgagacttgccgcaatgttcttttgtgccgtggttatcat
aggggtccttcaccagaatttcaaggacacctccatgcagaagactatacctctggtggccctcacactcacatcttacctg
ggcttgacacaaccttttttgggcctgtgtgcatttctggcaacccgcatatttgggcgaaggagtatcccagtgaatgaggca
ctcgcagcagctggtctagtgggagtgctggcaggactggcttttcaggagatggagaacttccttggtccgattgcagttgg
aggactcctgatgatgctggttagcgtggctgggagggtggatgggctagagctcaagaagcttggtgaagtttcatggga
agaggaggcggagatcagcgggagttccgcccgctatgatgtggcactcagtgaacaaggggagttcaagctgctttctg
aagagaaagtgccatgggaccaggttgtgatgacctcgctggccttggttgggggctgccctccatccatttgctcttctgctgg
tccttgctgggtggctgtttcatgtcaggggagctaggagaagtggggatgtcttgtgggatattcccactcctaagatcatcg
aggaatgtgaacatctggaggatgggatttatggcatattccagtcaaccttcttgggggcctcccagcgaggagtgggagt
ggcacagggagggtgttccacacaatgtggcatgtcacaagaggagctttccttgtcaggaatggcaagaagttgattcc
atcttgggcttcagtaaaggaagaccttgtcgccatggtggctcatggaagttggaaggcagatgggatggagaggaag
aggtccagttgatcgcggctgttccaggaaagaacgtggtcaacgtccagacaaaaccgagcttgttcaaagtgaggaat
gggggagaaatcggggctgtcgctcttgactatccgagtggcacttcaggatctcctattgttaacaggaacggagaggtg
attgggctgtacggcaatggcatccttgtcggtgacaactccttcgtgtccgccatatcccagactgaggtgaaggaagaag
gaaaggaggagctccaagagatcccgacaatgctaaagaaaggaatgacaactgtccttgattttcatcctggagctggg
aagacaagacgtttcctcccacagatcttggccgagtgcgcacggagacgcttgcgcactcttgtgttggccccccaccagg
gttgttctttctgaaatgaaggaggcttttcacggcctggacgtgaaattccacacacaggcttttccgctcacggcagcggg
agagaagtcattgatgccatgtgccatgccaccctaacttacaggatgttggaaccaactaggggttgttaactgggaagtga
tcattatggatgaagcccattttttggatccagctagcatagccgctagaggttgggcagcgcacagagctagggcaaatg
aaagtgcaacaatcttgatgacagccacaccgcctgggactagtgatgaatttccacattcaaatggtgaaatagaagatg
ttcaaacggacatacccagtgagccctggaacacagggcatgactggatcctagctgacaaaaggcccacggcatggtt
ccttccatccatcagagctgcaaatgtcatggcgcctctttgcgtaaggctggaaagagtgtggtggtcctgaacaggaaaa
cctttgagagagaatacccacgataaagcagaagaaacctgactttatattggccactgacatagctgaaatgggagcc
aacctttgcgtggagcgagtgctggattgcaggacggcttttaagcctgtgcttgtggatgaagggaggaaggtggcaata
aaagggccacttcgtatctccgcatcctctgctgctcaaaggagggggcgcattgggagaaatcccaacagagatggag
actcatactactattctgagcctacaagtgaaaataatgcccaccacgtctgctggttggaggcctcaatgctcttggacaac
atggaggtgagggggtggaatggtcgccccactctatggcgttgaaggaactaaaacaccagtttcccctggtgaaatgag
actgagggatgaccagaggaaagtcttcagagaactagtgaggaattgtgacctgcccgtttggctttcgtggcaagtggc
caaggctggtttgaagacgaatgatcgtaagtggtgttttgaaggccctgaggaacatgagatcttgaatgacagcggtga
aacagtgaagtgcagggctcctggaggagcaaagaagcctctgcgcccaaggtggtgtgatgaaagggtgtcatctgac
cagagtgcgctgtctgaatttattaagtttgctgaaggtaggaggggagctgctgaagtgctagttgtgctgagtgaactccct
gatttcctggctaaaaaggtggagaggcaatggataccatcagtgtgttcctccactctgaggaaggctctagggcttacc
gcaatgcactatcaatgatgcctgaggcaatgacaatagtcatgctgtttatactggctggactactgacatcgggaatggtc
atcttttcatgtctcccaaaggcatcagtagaatgtctatggcgatgggcacaatggccggctgtggatatctcatgttccttgg
aggcgtcaaacccactcacatctcctatgtcatgctcatattctttgtcctgatggtggttgtgatccccgagccagggcaaca
aaggtccatccaagacaaccaagtggcatacctcattattggcatcctgacgctggtttcagcggtggcagccaacgagct
aggcatgctggagaaaaccaaagaggacctctttgggaagaagaacttaattccatctagtgcttcaccctggagttggcc
ggatcttgacctgaagccaggagctgcctggacagtgtacgttggcattgttacaatgctctctccaatgttgcaccactggat
caaagtcgaatatggcaacctgtctctgtctggaatagcccagtcagcctcagtcctttctttcatggacaaggggataccatt
catgaagatgaatatctcggtcataatgctgctggtcagtggctggaattcaataacagtgatgcctctgctctgtggcatagg
gtgcgccatgctccactggtctctcattttacctggaatcaaagcgcagcagtcaaagcttgcacagagaagggtgttccat
ggcgttgccgagaaccctgtggttgatgggaatccaacagttgacattgaggaagctcctgaaatgcctgcccttatgaga
agaaactggctctatatctccttcttgctctcagcctagcttctgttgccatgtgcagaacgccctttttcattggctgaaggcattgt
cctagcatcagctgccttagggccgctcatagagggaaacaccagccttcttttggaatggacccatggctgtctccatgaca
ggagtcatgaggggggaatcactatgcttttgtgggagtcatgtacaatctatggaagatgaaaactggacgccgggggag
cgcgaatggaaaaactttgggtgaagtctggaagagggaactgaatctgttggacaagcgacagtttgagttgtataaaag

```
gaccgacattgtggaggtggatcgtgatacggcacgcaggcatttggccgaagggaaggtggacaccggggtggcggt
ctccaggggaccgcaaagttaaggtggttccatgagcgtggctatgtcaagctggaaggtagggtgattgacctggggtg
tggccgcggaggctggtgttactacgctgctgcgcaaaaggaagtgagtggggtcaaaggatttactcttggaagagacg
gccatgagaaacccatgaatgtgcaaagtctggatggaacatcatcaccttcaaggacaaaactgatatccaccgccta
gaaccagtgaaatgtgacaccctttgtgtgacattggagagtcatcatcgtcatcggtcacagagggggaaaggaccgtg
agagttcttgatactgtagaaaaatggctggcttgtgggggttgacaacttctgtgtgaaggtgttagctccatacatgccagat
gttcttgagaaactggaattgctccaaaggaggtttggcggaacagtgatcaggaaccctctctccaggaattccactcatg
aaatgtactacgtgtctggagcccgcagcaatgtcacatttactgtgaaccaaacatcccgcctcctgatgaggagaatga
ggcgtccaactggaaaagtgaccctggaggctgacgtcatcctcccaattgggacacgcagtgttgagacagacaaggg
accccctggacaaagaggccatagaagaaagggttgagaggataaaatctgagtacatgacctcttggttttatgacaatg
acaaccccctacaggacctggcactactgtggctcctatgtcacaaaaacctcaggaagtgcggcgagcatggtaaatggt
gttattaaaattctgacatatccatgggacaggatagaggaggtcacaagaatggcaatgactgacacaaccccttttgga
cagcaaagagtgtttaaagaaaaagttgacaccagagcaaaggatccaccagcgggaactaggaagatcatgaaagt
tgtcaacaggtggctgttccgccacctggccagagaaaagaaccccagactgtgcacaaaggaagaatttattgcaaaa
gtccgaagtcatgcagccattggagcttacctggaagaacaagaacagtggaagactgccaatgaggctgtccaagacc
caaagttctgggaactggtggatgaagaaaggaagctgcaccaacaaggcaggtgtcggacttgtgtgtacaacatgat
ggggaaaagagagaagaagctgtcagagtttgggaaagcaaagggaagccgtgccatatggtatatgtggctgggagc
gcggtatcttgagtttgaggccctgggattcctgaatgaggaccattgggcttccaggaaaactcaggaggaggagtgga
aggcattggcttacaataccctaggatatgtgatcagagacctggctgcaatggatggtggtggattctacgcggatgacacc
gctggatgggacacgcgcatcacagaggcagaccttgatgatgaacaggagatcttgaactacatgagcccacatcaca
aaaaactggcacaagcagtgatggaaatgacatacaagaacaaagtggtgaaagtgttgagaccagccccaggagg
gaaagcctacatggatgtcataagtcgacgagaccagagaggatccgggcaggtagtgacttatgctctgaacaccatc
accaacttgaaagtccaattgatcagaatggcagaagcagagatggtgatacatcaccaacatgttcaagattgtgatgaa
tcagttctgaccaggctggaggcatggctcactgagcacggatgtgacagactgaagaggatggcggtgagtggagacg
actgtgtggtccggcccatcgatgacaggttcggcctggccctgtcccatctcaacgccatgtccaaggttagaaaggacat
atctgaatggcagccatcaaaagggtggaatgattgggagaatgtgcccttctgttcccaccacttccatgaactacagctg
aaggatggcaggaggattgtggtgccttgccgagaacaggacgagctcattgggagaggaaggtgtctccaggaaac
ggctggatgatcaaggaaacagcttgcctcagcaaagcctatgccaacatgtggtcactgatgtattttcacaaaagggac
atgaggctactgtcattggctgtttcctcagctgttcccacctcatgggttccacaaggacgcacaacatggtcgattcatggg
aaaggggagtggatgaccacggaagacatgcttgaggtgtggaacagagtatggataaccaacaacccacacatgca
ggacaagacaatggtgaaaaaatggagagatgtcccttatctaaccaagagacaagacaagctgtgcggatcactgatt
ggaatgaccaatagggccacctgggcctcccacatccatttagtcatccatcgtatccgaacgctgattggacaggagaa
atacactgactacctaacagtcatggacaggtattctgtggatgctgacctgcaactgggtgagcttatctgaaacaccatct
aacaggaataaccgggatacaaaccacgggtggagaaccggactccccacaacctgaaaccgggatataaaccacg
gctggagaaccggactccgcacttaaaatgaaacagaaaccgggataaaaactacggatggagaaccggactccaca
cattgagacagaagaagttgtcagcccagaaccccacacgagttttgccactgctaagctgtgaggcagtgcaggctggg
acagccgacctccaggttgcgaaaaacctggttctgggacctcccaccccagagtaaaaagaacggagcctccgctac
cacccctcccacgtggtggtagaaagacggggtctagaggttagaggagaccctccagggaacaaatagtgggaccata
ttgacgccagggaaagaccggagtggttctctgcttttcctcagaggtctgtgagcacagtttgctcaagaataagcagac
ctttggatgacaaacacaaaaccactgggtcggcatggcatctccacctcctcgcggtccgacctgggcatccgaaggag
gacgcacgtccactcggatggctaagggagagccacgagctcctcgacagatcataatcagccataccacatttgtaga
ggttttacttgctttaaaaaacctcccacacctcccctgaacctgaaacataaaatgaatgcaattgttgttgttaacttgtttatt
gcagcttataatggttacaaataaagcaatagcatcacaaatttcacaaataaagcatttttttcactgcattctagttgtggtttg
tccaaactcatcaagatctcgagcaagacgttcccgttgaatatggctcataacaccccttgtattactgtttatgtaagcaga
cagttttattgttcatgatgatatattttatcttgtgcaatgtaacatcagagattttgagacacaacgtggctttgttgaataaatc
gaacttttgctgagttgaaggatcagatcacgcatcttcccgacaacgcagaccgttccgtggcaaagcaaaagttcaaaa
tcaccaactggtccacctacaacaaagctctcatcaaccgtggctccctcactttctggctggatgatgggcgattcaggc
ctggtatgagtcagcaacaccttcttcacgaggcagacctcagcgctagcggagtgtatactggcttactatgttggcactga
tgagggtgtcagtgaagtgcttcatgtggcaggagaaaaaaggctgcaccggtgcgtcagcagaatatgtgatacaggat
atattccgcttcctcgctcactgactcgctacgctcggtcgttcgactgcggcgagcggaaatggcttacgaacggggcgga
gatttcctggaagatgccaggaagatacttaacagggaagtgagagggccgcggcaaagccgttttccataggctccgc
```

Fig. 8C ccccctgacaagcatcacgaaatctgacgctcaaatcagtggtggcgaaacccgacaggactataaagataccaggcg
tttccctggcggctccctcgtgcgctctcctgttcctgcctttcggtttaccggtgtcattccgctgttatggccgcgtttgtctcatt
ccacgcctgacactcagttccgggtaggcagttcgctccaagctggactgtatgcacgaaccccccgttcagtccgaccgc
tgcgccttatccggtaactatcgtcttgagtccaacccggaaagacatgcaaaagcaccactggcagcagccactggtaat
tgatttagaggagttagtcttgaagtcatgcgccggttaaggctaaactgaaaggacaagttttggtgactgcgctcctccaa
gccagttacctcggttcaaagagttggtagctcagagaaccttcgaaaaaccgccctgcaaggcggttttttcgttttcagag
caagagattacgcgcagaccaaaacgatctcaagaagatcatcttattaaggggtctgacgctcagtggaacgaaaact
cacgttaagggattttggtcatgagattatcaaaaaggatcttcacctagatccttttaaattaaaaatgaagttttaaatcaatc
taaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgatac
cgcgagacccacgctcaccggctccagatttatcagcaataaaccagccagccggaagggccgagcgcagaagtggt
cctgcaactttatccgcctccatccagtctattaattgttgccgggaagctagagtaagtagttcgccagttaatagtttgcgca
acgttgttgccattgctgcaggcatcgtggtgtcacgctcgtcgtttggtatggcttcattcagctccggttcccaacgatcaag
gcgagttacatgatccccatgttgtgcaaaaaagcggttagctccttcggtcctccgatcgttgtcagaagtaagttggccg
cagtgttatcactcatggttatggcagcactgcataattctcttactgtcatgccatccgtaagatgcttttctgtgactggtgagta
ctcaaccaagtcattctgagaatagtgtatgcggcgaccgagttgctcttgcccggcgtcaacacgggataataccgcgcc
acatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacag
gaaggcaaaatgccgcaaaaaagggaataagggcgacacggaaatgttgaatactcatactcttcctttttcaatattattg
aagcatttatcaggggttattgtctcatgagcggatacatatttgaatgtatttagaaaaataaacaaataggggttccgcgcac
atttccccgaaaagtgccacctgacgtgtcgacgcggccgctagcgatgaccctgctgattggttcgctgaccatttccgggt
gcgggacggcgttaccagaaactcagaaggttcgtccaaccaaaccgactctgacggcagtttacgagagagatgatag
ggtctgcttcagtaagccagatgctacacaattaggcttgtacatattgtcgttagaacgcggctacaattaatacataaccttt
atgtatcatacacatacgatttaggtgacactata (SEQ ID NO: 6)

Fig.8D gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattct
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgtgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg

Fig. 8E

```
tgccagagggacatgcaataccogtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccataggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttaacatgatgtgcctgaaagtgcattttaaccacgagatttgcacacaagtcttccacaaaagcatctctcgccgttgca
ctaaatctgtgacttcggtcgtctcaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcaccccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggt
gtgcggagcgctgtataagaaattcccggaaagcttcgatttacagccgatcgaagtaggaaaagcgcgactggtcaaa
ggtgcagctaaacatatcattcatgccgtaggaccaaacttcaacaaagtttcggaggttgaaggtgacaaacagttggca
gaggcttatgagtccatcgctaagattgtcaacgataacaattacaagtcagtagcgattccactgttgtccaccggcatcttt
ccgggaacaaagatcgactaacccaatcattgaaccatttgctgacagctttagacaccactgatgcagatgtagccatat
actgcagggacaagaaatggaaatgactctcaaggaagcagtggctaggagagaagcagtggaggagatatgcata
tccgacgactcttcagtgacagaacctgatgcagagctggtgagggtgcatccgaagagttctttggctggaaggaaggg
ctacagcacaagcgatggcaaaactttctcatatttggaagggaccaagtttcaccaggcggccaaggatatagcagaa
attaatgccatgtggcccgttgcaacggaggccaatgagcaggtatgcatgtatatcctcggagaaagcatgagcagtatt
aggtcgaaatgccccgtcgaagagtcggaagcctccacaccacctagcacgctgccttgcttgtgcatccatgccatgact
ccagaaagagtacagcgcctaaaagcctcacgtccagaacaaattactgtgtgctcatcctttccattgccgaagtataga
atcactggtgtgcagaagatccaatgctcccagcctatattgttctcaccgaaagtgcctgcgtatattcatccaaggaagtat
ctcgtggaaacaccaccggtagacgagactccggagccatcggcagagaaccaatccacagaggggacacctgaac
aaccaccacttataaccgaggatgagaccaggactagaacgcctgagccgatcatcatcgaagaggaagaagaggat
agcataagtttgctgtcagatggcccgacccaccaggtgctgcaagtcgaggcagacattcacgggccgccctctgtatct
agctcatcctggtccattcctcatgcatccgactttgatgtggacagtttatccatacttgacacctggagggagctagcgtg
accagcggggcaacgtcagccgagactaactcttacttcgcaaagagtatggagtttctggcgcgaccggtgcctgcgcct
cgaacagtattcaggaaccctccacatcccgctccgcgcacaagaacaccgtcacttgcacccagcagggcctgctcga
gaaccagcctagtttccaccccgccaggcgtgaatagggtgatcactagagaggagctcgaggcgcttaccccgtcacg
cactcctagcaggtcggtctcgagaaccagcctggtctccaacccgccaggcgtaaatagggtgattacaagagaggag
tttgaggcgttcgtagcacaacaacaatgacggtttgatgcgggtgcatacatcttttcctccgacaccggtcaagggcattta
caacaaaaatcagtaaggcaaacggtgctatccgaagtggtgttggagaggaccgaattggagatttcgtatgccccgcg
cctcgaccaagaaaagaagaattactacgcaagaaattacagttaaatcccacacctgctaacagaagcagatacca
gtccaggaaggtggagaacatgaaagccataacagctagacgtattctgcaaggcctagggcattatttgaaggcagaa
```

Fig. 8F ggaaaagtggagtgctaccgaaccctgcatcctgttcctttgtattcatctagtgtgaaccgtgccttttcaagccccaaggtc
gcagtggaagcctgtaacgccatgttgaaagagaactttccgactgtggcttcttactgtattattccagagtacgatgcctat
tggacatggttgacggagcttcatgctgcttagacactgccagttttgccctgcaaagctgcgcagctttccaaagaaacac
tcctatttggaacccacaatacgatcggcagtgccttcagcgatccagaacacgctccagaacgtcctggcagctgccac
aaaaagaaattgcaatgtcacgcaaatgagagaattgcccgtattggattcggcggcctttaatgtggaatgcttcaagaa
atatgcgtgtaataatgaatattgggaaacgtttaaagaaaacccatcaggcttactgaagaaaacgtggtaaattacatt
accaaattaaaaggaccaaaagctgctgctcttttttgcgaagacacataatttgaatatgttgcaggacataccaatggaca
ggtttgtaatggacttaaagagagacgtgaaagtgactccaggaacaaaacatactgaagaacggcccaaggtacagg
tgatccaggctgccgatccgctagcaacagcgtatctgtgcggaatccaccgagagctggttaggagattaaatgcggtcc
tgccttccgaacattcatacactgtttgatatgtcggctgaagactttgacgctattatagccgagcacttccagcctggggattgt
gttctggaaactgacatcgcgtcgtttgataaaagtgaggacgacgccatggctctgaccgcgttaatgattctggaagactt
aggtgtggacgcagagctgttgacgctgattgaggcggcttccggcgaaatttcatcaatacatttgcccactaaaactaaat
ttaaattcggagccatgatgaaatctggaatgttcctcacactgtttgtaacacagtcattaacattgtaatcgcaagcagag
tgttgagagaacggctaaccggatcaccatgtgcagcattcattggagatgacaatatcgtgaaaggagtcaaatcggac
aaattaatggcagacaggtgcgccacctggttaaatatggaagtcaagattatagatgctgtggtgggcgagaaagcgcc
ttatttctgtggagggtttattttgtgtgactccgtgaccggcacagcgtgccgtgtggcagaccccctaaaaaggctgtttaag
cttggcaaacctctggcagcagacgatgaacatgatgatgacaggagaagggcattgcatgaagagtcaacacgctgg
aaccgagtgggtattcttcagagctgtgcaaggcagtagaatcaaggtatgaaaccgtaggaacttccatcatagttatgg
ccatgactactctagctagcagtgttaaatcattcagctacctgagaggggcccctataactctctacggctaacctgaatgg
actacgacatagtctagtccgccaagtctagaccatgtctggtcgtaaagctcagggaaaaaccctgggcgtcaatatggt
acgacgaggagttcgctccttgtcaaacaaaataaaacaaaaaacaaaacaaattggaaacagacctggaccttcaag
aggtgttcaaggatttatcttttttcttttgttcaacattttgactggaaaaaagatcacagcccacctaaagaggttgtggaaaa
tgctggacccaagacaaggcttggctgttctaaggaaagtcaagagagtggtggccagtttgatgagaggattgtcctcaa
ggaaacgccgttcccatgatgttctgactgtgcaattcctaattttgggaatgctgttgatgacgggtggataagggcccctat
aactctctacggctaacctgaatggactacgacatagtctagtccgccaagtctagagcttaccatgaccgagtacaagcc
cacggtgcgcctcgccacccgcgacgacgtccccagggccgtacgcaccctcgccgccgcgttcgccgactacccgc
cacgcgccacaccgtcgatccggaccgccacatcgagcgggtcaccgagctgcaagaactcttcctcacgcgcgtcgg
gctcgacatcggcaaggtgtgggtcgcggacgacggcgccgcggtggcggtctggaccacgccggagagcgtcgaag
cggggcggtgttcgccgagatcggcccgcgcatggccgagttgagcggttcccggctggccgcgcagcaacagatgg
aaggcctcctggcgccgcaccggcccaaggagcccgcgtggttcctggccaccgtcggcgtctcgcccgaccaccagg
gcaagggtctgggcagcgccgtcgtgctccccggagtggaggcggccgagcgcgccggggtgcccgccttcctggaga
cctccgcgcccgcaacctccccttctacgagcggctcggcttcaccgtcaccgccgacgtcgagtcccgaaggaccg
cgcgacctggtgcatgacccgcaagcccggtgcctgacgcccgccccacgacccgcagcgcccgaccgaaaggagc
gcacgaccccatgatcgctagaccatggggtaccgagtatgttacgtgcaaaggtgattgtcaccccccgaaagaccata
ttgtgacacaccctcagtatcacgcccaaacatttacagccgcggtgtcaaaaaccgcgtggacgtggttaacatccctgct
gggaggatcagccgtaattattataattggcttggtgctggctactattgtgccatgtacgtgctgaccaaccagaaacata
attgaatacagcagcaattggcaagctgcttacatagaactcgcggcgattggcatgccgccttaaaattttttatttatttttctt
ttcttttccgaatcggattttgttttaatatttcaaaaaaaaaaaaaaaaaaaaaaaacgcgtcgaggggaattaattcttga
agacgaaagggccaggtggcacttttcggggaaatgtgcgcggaacccctatttgtttattttctaaatacattcaaatatgta
tccgctcatgagacaataaccctgataaatgcttcaataatattgaaaaggaagagtatgagtattcaacatttccgtgtcg
cccttattccctttttgcggcatttttgccttcctgtttttgctcacccagaaacgctggtgaaagtaaaagatgctgaagatcagtt
gggtgcacgagtgggttacatcgaactggatctcaacagcggtaagatccttgagagttttcgccccgaagaacgttttcca
atgatgagcacttttaaagttctgctatgtggcgcggtattatcccgtgttgacgccgggcaagagcaactcggtcgccgcat
acactattctcagaatgacttggttgagtactcaccagtcacagaaaagcatcttacggatggcatgacagtaagagaatta
tgcagtgctgccataaccatgagtgataacactgcggccaacttacttctgacaacgatcggaggaccgaaggagctaac
cgcttttttgcacaacatggggatcatgtaactcgccttgatcgttgggaaccggagctgaatgaagccataccaaacgac
gagcgtgacaccacgatgcctgtagcaatggcaacaacgttgcgcaaactattaactggcgaactacttactctagcttccc
ggcaacaattaatagactggatggaggcggataaagttgcaggaccacttctgcgctcggcccttccggctggctggtttatt
gctgataaatctggagccggtgagcgtgggtctcgcggtatcattgcagcactggggccagatggtaagccctcccgtatc
gtagttatctacacgacggggagtcaggcaactatggatgaacgaaatagacagatcgctgagataggtgcctcactgatt
aagcattggtaactgtcagaccaagtttactcatatatactttagattgatttaaaacttcattttaatttaaaaggatctaggtga agatccttttgataatctcatgaccaaaatcccttaacgtgagttttcgttccactgagcgtcagaccccgtagaaaagatca
aaggatcttcttgagatcctttttttctgcgcgtaatctgctgcttgcaaacaaaaaaaccaccgctaccagcggtggtttgtttg
ccggatcaagagctaccaactctcttttccgaaggtaactggcttcagcagagcgcagataccaaatactgtccttctagtgta
gccgtagttaggccaccacttcaagaactctgtagcaccgcctacatacctcgctctgctaatcctgttaccagtggctgctgc
cagtggcgataagtcgtgtcttaccgggttggactcaagacgatagttaccggataaggcgcagcggtcgggctgaacgg
ggggttcgtgcacacagcccagcttggagcgaacgacctacaccgaactgagatacctacagcgtgagcattgagaaa
gcgccacgcttcccgaagggagaaaggcggacaggtatccggtaagcggcagggtcggaacaggagagcgcacga
gggagcttccaggggggaaacgcctggtatctttatagtcctgtcgggtttcgccacctctgacttgagcgtcgattttgtgatgc
tcgtcaggggggcggagcctatggaaaaacgccagcaacgcgagctcgatttaggtgacactata
(SEQ ID NO: 7)

Fig. 8H gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgacc..tgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattctt
agaaagaagtatttgaaacc:.tccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccaccttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaataccatgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccatagggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcg:tcatagccattataagacctaaaaaggcagtgctctgcggggatcccaaacagtgcgg
ttttttaacatgatgtgcctgaaagtgcatttaaccacgagatttgcacacaagtcttccacaaaagcatctctgccgttgca
ctaaatctgtgacttcggtcgtctcaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcaccccacctcagaacatgtgaacgtcctactgacccgcacggaggaccgcatc
gtgtggaaaacactagccggcgacccatggataaaaaacactgactgccaagtaccctgggaatttcactgccacgatag
aggagtggcaagcagagcatgatgccatcatgaggcacatcttggagagaccggaccctaccgacgtcttccagaataa

Fig. 8I ggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgactttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggtgtgcg
gagcgctgtataagaaattcccggaaagcttcgatttacagccgatcgaagtaggaaaagcgcgactggtcaaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaatgactctcaaggaagcagtggctaggagagaagcagtggaggagatatgcatatccga
cgactcttcagtgacagaacctgatgcagagctggtgagggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccacctagcacgctgccttgcttgtgcatccatgccatgactccaga
aagagtacagcgcctaaaagcctcacgtccagaacaaattactgtgtgctcatcctttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggcccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagttccaccccgccaggcgtgaatagggtgatcactagagaggagctcgaggcgcttaccccgtcacgcactcc
tagcaggtcggtctcgagaaccagcctggtctccaacccgccaggcgtaaatagggtgattacaagagaggagtttgag
gcgttcgtagcacaacaacaatgacggtttgatgcgggtgcatacatcttttcctccgacaccggtcaagggcatttacaac
aaaaatcagtaaggcaaacggtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatcagtgtgaaccgtgccttttcaagcccccaaggtcgcag
tggaagcctgtaacgccatgttgaaagagaacttccgactgtggcttcttactgtattattccagagtacgatgcctatttgga
catggttgacggagcttcatgctgcttagacactgccagttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaagaaaacccccatcaggcttactgaagaaaacgtggtaaattacattaccaa
attaaaaggaccaaaagctgctgctctttttgcgaagacacataatttgaatatgttgcaggacataccaatggacaggtttgt
aatggacttaaagagagacgtgaaagtgactccaggaacaaaacatactgaagaacggcccaaggtacaggtgatcc
aggctgccgatcgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgtgttctg
gaaactgacatcgcgtcgtttgataaaagtgaggacgacgccatggctctgaccgcgttaatgattctggaagacttaggtg
tggacgcagagctgttgacgctgattgaggcggcttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaaggagtcaaatcggacaaatta
atggcagacaggtgcgccacctggttgaatatggaagtcaagattatagatgctgtggtgggcgagaaagcgccttatttct

Fig. 8J gtggagggtttattttgtgtgactccgtgaccggcacagcgtgccgtgtggcagacccctaaaaaggctgtttaagcttggc
aaacctctggcagcagacgatgaacatgatgatgacaggagaagggcattgcatgaagagtcaacacgctggaaccg
agtgggtattctttcagagctgtgcaaggcagtagaatcaaggtatgaaaccgtaggaacttccatcatagttatggccatga
ctactctagctagcagtgttaaatcattcagctacctgagagggcccctataactctctacggctaacctgaatggactacg
acatagtctagtccgccaagtctagaccatgtctggtcgtaaagctcagggaaaaaccctgggcgtcaatatggtacgacg
aggagttcgctccttgtcaaacaaaataaaacaaaaaacaaaacaaattggaaacagacctggaccttcaagaggtgtt
caaggatttatcttttctttttgttcaacattttgactggaaaaaagatcacagcccacctaaagaggttgtggaaaatgctgga
cccaagacaaggcttggctgttctaaggaaagtcaagagagtggtggccagtttgatgagaggattgtcctcaaggaaac
gccgttcccatgatgttctgactgtgcaattcctaattttgggaatgctgttgatgacgggtggagtgaccttggtgcggaaaaa
cagatggttgctcctaaatgtgacatctgaggacctcgggtaagggcccctataactctctacggctaacctgaatggacta
cgacatagtctagtccgccaagtctagagcttaccatgaccgagtacaagcccacggtgcgcctcgccacccgcgacga
cgtcccagggccgtacgcaccctcgccgccgcgttcgccgactaccccgccacgcgccacaccgtcgatccggaccg
ccacatcgagcgggtcaccgagctgcaagaactcttcctcacgcgcgtcgggctcgacatcggcaaggtgtgggtcgcg
gacgacggcgccgcggtggcggtctggaccacgccggagagcgtcgaagcgggggcggtgttcgccgagatcggccc
gcgcatggccgagttgagcggttcccggctggccgcgcagcaacagatggaaggcctcctggcgccgcaccggccca
aggagcccgcgtggttcctggccaccgtcggcgtctcgcccgaccaccagggcaagggtctgggcagcgccgtcgtgct
ccccggagtggaggcggccgagcgcgccggggtgcccgccttcctggagacctccgcgccccgcaacctcccccttctac
gagcggctcggcttcaccgtcaccgccgacgtcgagtgcccgaaggaccgcgcgacctggtgcatgacccgcaagccc
ggtgcctgacgccgccccacgaccccgcagcgcccgaccgaaaggagcgcacgaccccatgatcgctagaccatgg
ggtaccgagtatgttacgtgcaaggtgattgtcaccccccgaaagaccatattgtgacacaccctcagtatcacgcccaa
acatttacagccgcggtgtcaaaaaccgcgtggacgtggtaacatccctgctgggaggatcagccgtaattattataattg
gcttggtgctggctactattgtggccatgtacgtgctgaccaaccagaaacataattgaatacagcagcaattggcaagctg
cttacatagaactcgcggcgattggcatgccgccttaaaattttatttttattttttcttttcttttccgaatcggattttgtttttaatatttc
aaaaaaaaaaaaaaaaaaaaaaaaacgcgtcgaggggaattaattcttgaagacgaaagggccaggtggcacttttc
ggggaaatgtgcgcggaaccccctatttgtttattttctaaatacattcaaatatgtatccgctcatgagacaataaccctgata
aatgcttcaataatattgaaaaggaagagtatgagtattcaacatttccgtgtcgcccttattcccttttttgcggcattttgcctt
cctgtttttgctcacccagaaacgctggtgaaagtaaaagatgctgaagatcagttgggtgcacgagtgggttacatcgaac
tggatctcaacagcggtaagatccttgagagttttcgccccgaagaacgttttccaatgatgagcacttttaaagttctgctatg
tggcgcggtattatcccgtgttgacgccgggcaagagcaactcggtcgccgcatacactattctcagaatgacttggttgagt
actcaccagtcacagaaaagcatcttacggatggcatgacagtaagagaattatgcagtgctgccataaccatgagtgat
aacactgcggccaacttacttctgacaacgatcggaggaccgaaggagctaaccgcttttttgcacaacatgggggatcat
gtaactcgccttgatcgttgggaaccggagctgaatgaagccataccaaacgacgagcgtgacaccacgatgcctgtag
caatggcaacaacgttgcgcaaactattaactggcgaactacttactctagcttccggcaacaattaatagactggatgga
ggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagt
ttactcatatatactttagattgatttaaaacttcattttaattaaaaggatctaggtgaagatccttttgataatctcatgaccaa
aatcccttaacgtgagttttcgttccactgagcgtcagaccccgtagaaaagatcaaaggatcttcttgagatcctttttttctgc
gcgtaatctgctgcttgcaaacaaaaaaaccaccgctaccagcggtggtttgtttgccggatcaagagctaccaactctttt
ccgaaggtaactggcttcagcagagcgcagataccaaatactgtccttctagtgtagccgtagttaggccaccacttcaag
aactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagct
tggagcgaacgacctacaccgaactgagatacctacagcgtgagcattgagaaagcgccacgcttcccgaagggaga
aaggcggacaggtatccggtaagcggcagggtcggaacaggagagcgcacgagggagcttccaggggggaaacgcc
tggtatctttatagtcctgtcgggtttcgccacctctgacttgagcgtcgatttttgtgatgctcgtcaggggggcggagcctatgg
aaaaacgccagcaacgcgagctcgatttaggtgacactata (SEQ ID NO: 8)

Fig.8K

```
gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattctt
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccaccctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggacttttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccatagggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttaacatgatgtgcctgaaagtgcattttaaccacgagatttgcacacaagtcttccacaaaagcatctctcgccgttgca
ctaaatctgtgacttcggtcgtctcaaccttgttacgacaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcacccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggatt
aggcatcccaggtgatgtgcccaaatatgacataatatttgttaatgtgaggacccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggagggggtgtgcg
```

Fig. 8L gagcgctgtataagaaattcccggaaagcttcgatttacagccgatcgaagtaggaaaagcgcgactggtcaaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaatgactctcaaggaagcagtggctaggagagaagcagtggaggagatatgcatatccga
cgactcttcagtgacagaacctgatgcagagctggtgagggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccacctagcacgctgccttgcttgtgcatccatgccatgactccaga
aagagtacagcgcctaaaagcctcacgtccagaacaaattactgtgtgctcatccttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggccccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagttccaccccgccaggcgtgaataggggtgatcactagagaggagctcgaggcgcttaccccgtcacgcactcc
tagcaggtcggtctcgagaaccagcctggtctccaacccgccaggcgtaaataggggtgattacaagagaggagtttgag
gcgttcgtagcacaacaacaatgacggtttgatgcgggtgcatacatctttttcctccgacaccggtcaagggcatttacaac
aaaaatcagtaaggcaaaccgtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatctagtgtgaaccgtgccttttcaagcccaaggtcgcag
tggaagcctgtaacgccatgttgaaagagaactttccgactgtggcttcttactgtattattccagagtacgatgcctatttgga
catggttgacggagcttcatgctgcttagacactgccagttttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaaagaaaaccccatcaggcttactgaagaaaacgtggtaaattacattaccaa
attaaaaggaccaaaagctgctgctcttttgcgaagacacataatttgaatatgttgcaggacataccaatggacaggtttgt
aatggacttaaagagagacgtgaaagtgactccaggaacaaaacatactgaagaacggcccaaggtacaggtgatcc
aggctgccgatccgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgtgtctg
gaaactgacatcgcgtcgtttgataaaagtgaggacgacgccatggctctgaccgcgttaatgattctggaagacttaggtg
tggacgcagagctgttgacgctgattgaggcggctttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaaggagtcaaatcggacaaatta
atggcagacaggtgcgccacctggttgaatatggaagtcaagattatagatgctgtggtgggcgagaaagcgccttatttct
gtggagggtttattttgtgtgactccgtgaccggcacagcgtgccgtgtggcagacccccctaaaaaggctgtttaagcttggc
aaacctctggcagcagacgatgaacatgatgatgacaggagaagggcattgcatgaagagtcaacacgctggaaccg
agtgggtattctttcagagctgtgcaaggcagtagaatcaaggtatgaaaccgtaggaacttccatcatagttatggccatga
ctactctagctagcagtgttaaatcattcagctacctgagaggggcccctataactctctacggctaacctgaatggactacg
acatagtctagtccgccaagtctagaccatgtctggtcgtaaagctcagggaaaaaccctgggcgtcaatatggtacgacg
aggagttcgctccttgtcaaacaaaataaaacaaaaacaaaacaaattggaaacagacctggaccttcaagaggtgtt
caaggatttatcttttctttttgttcaacattttgactggaaaaaagatcacagcccacctaaagaggttgtggaaaatgctgga
cccaagacaaggcttggctgttctaaggaaagtcaagagagtggtggccagtttgatgagaggattgtcctcaaggaaac
gccgttcccatgatgttctgactgtgcaattcctaattttgggaatgctgttgatgacgggtggagtgaccttggtgcggaaaaa
cagatggttgctcctaaatgtgacatctgaggacctcgggaaaacattctctgtgggcacaggcaactgcacaacaaacat
tttggaagccaagtactggtgcccagactcaatggaatacaactgtcccaatctcagtccaagagaggagccagatgaca
ttgattgctggtgctatggggtggaaaacgttagagtcgcatatggtaagtgtgactcagcaggcaggtctaggaggtcaag
aagggccattgacttgcctacgcatgaaaaccatggtttgaagacccggcaagaaaaatggatgactggaagaatgggt

```
gaaaggcaactccaaaagattgagagatggttcgtgaggaaccccttttttgcagtgacggctctgaccattgcctaccttgt
gggaagcaacatgacgcaacgagtcgtgattgccctactggtcttggctgttggtccggcctactcagctcactgcattgga
attactgacagggatttcattgaggggggtgcatggaggaacttgggtttcagctaccctggagcaagacaagtgtgtcactgt
tatggcccctgacaagccttcattggacatctcactagagacagtagccattgatagacctgctgaggtgaggaaagtgtgt
tacaatgcagttctcactcatgtgaagattaatgacaagtgccccagcactggagaggcccacctagctgaagagaacga
aggggacaatgcgtgcaagcgcacttattctgatagaggctggggcaatggctgtggcctatttgggaaagggagcattgt
ggcatgcgccaaattcacttgtgccaaatccatgagtttgtttgaggttgatcagaccaaaattcagtatgtcatcagagcac
aattgcatgtaggggccaagcaggaaaattggaataccgacattaagactctcaagtttgatgccctgtcaggctcccagg
aagtcgagttcattgggtatggaaaagctacactggaatgccaggtgcaaactgcggtggactttggtaacagttacatcgc
tgagatggaaacagagagctggatagtggacagacagtgggcccaggacttgaccctgccatggcagagtggaagtgg
cggggtgtggagagagatgcatcatcttgtcgaatttgaacctccgcatgccgccactatcagagtactggccctgggaaa
ccaggaaggctccttgaaaacagctcttactggcgcaatgagggttacaaaggacacaaatgacaacaacctttacaaa
ctacatggtggacatgtttcttgcagagtgaaattgtcagctttgacactcaaggggacatcctacaaaatatgcactgacaa
aatgttttttgtcaagaacccaactgacactggccatggcactgttgtgatgcaggtgaaagtgtcaaaaggagcccctgc
aggattccagtgatagtagctgatgatcttacagcggcaatcaataaaggcattttggttacagttaaccccatcgcctcaac
caatgatgatgaagtgctgattgaggtgaacccacccttttggagacagctacattatcgttgggagaggagattcacgtctca
cttaccagtggcacaaagagggaagctcaataggaaagttgttcactcagaccatgaaaggcgtggaacgcctggccgt
catgggagacaccgcctgggatttcagctccgctggagggttcttcacttcggttgggaaaggaattcatacggtgtttggctc
tgcctttcaggggctattggcggcttgaactggataacaaaggtcatcatgggggcggtacttatatggggttggcatcaaca
caagaaacatgacaatgtccatgagcatgatcttggtaggagtgatcatgatgttttgtctctaggagttggggcgtaagcg
gcccctataactctctacggctaacctgaatggactacgacatagtctagtccgccaagtctagagcttaccatgaccgagt
acaagcccacggtgcgcctcgccacccgcgacgacgtccccagggccgtacgcaccctcgccgccgcgttcgccgact
accccgccacgcgccacaccgtcgatccggaccgccacatcgagcgggtcaccgagctgcaagaacttcctcacgc
gcgtcgggctcgacatcggcaaggtgtgggtcgcggacgacggcgccgcggtggcggtctggaccacgccggagagc
gtcgaagcgggggcggtgttcgccgagatcggcccgcgcatggccgagttgagcggttcccggctggccgcgcagcaa
cagatggaaggcctcctggccgccgcaccggcccaaggagcccgcgtggttcctggccaccgtcggcgtctcgcccgac
caccagggcaagggtctgggcagcgccgtcgtgctccccggagtggaggcggccgagcgcgccggggtgcccgcctt
cctggagacctccgcgccccgcaacctccccttctacgagcggctcggcttcaccgtcaccgccgacgtcgagtgcccga
aggaccgcgcgacctggtgcatgacccgcaagcccggtgcctgacgcccgccccacgacccgcagcgcccgaccga
aaggagcgcacgaccccatgatcgctagaccatgggtaccgagtatgttacgtgcaaaggtgattgtcaccccccgaa
agaccatattgtgacacacccctcagtatcacgcccaaacatttacagccgcggtgtcaaaaaccgcgtggacgtggttaac
atccctgctgggaggatcagccgtaattattataattggcttggtgctggctactattgtggccatgtacgtgctgaccaaccag
aaaacataattgaatacagcagcaattggcaagctgcttacatagaactcgcggcgattggcatgccgccttaaaattttattt
tattttttctttctttttccgaatcggattttgttttaatatttcaaaaaaaaaaaaaaaaaaaaaacgcgtcgaggggaatt
aattcttgaagacgaaagggccaggtggcacttttcggggaaatgtgcgcggaaccccctatttgtttatttttctaaatacattc
aaatatgtatccgctcatgagacaataaccctgataaatgcttcaataatattgaaaaaggaagagtatgagtattcaacatt
tccgtgtcgcccttattccctttttttgcggcattttgccttcctgtttttgctcacccagaaacgctggtgaaagtaaaagatgctga
agatcagttgggtgcacgagtggttacatcgaactggatctcaacagcggtaagatccttgagagttttcgccccgaaga
acgttttccaatgatgagcacttttaaagttctgctatgtggcgcggtattatcccgtgttgacgccgggcaagagcaactcggt
cgccgcatacactattctcagaatgacttggttgagtactcaccagtcacagaaaagcatcttacggatggcatgacagtaa
gagaattatgcagtgctgccataaccatgagtgataacactgcggccaacttacttctgacaacgatcggaggaccgaag
gagctaaccgcttttttgcacaacatgggggatcatgtaactcgccttgatcgttgggaaccggagctgaatgaagccatac
caaacgacgagcgtgacaccacgatgcctgtagcaatggcaacaacgttgcgcaaactattaactggcgaactacttact
ctagcttcccggcaacaattaatagactggatggaggcggataaagttgcaggaccacttctgcgctcggcccttccggct
ggctggtttattgctgataaatctggagccggtgagcgtgggtctcgcggtatcattgcagcactggggccagatggtaagc
cctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcattttaatttaaaag
gatctaggtgaagatcctttttgataatctcatgaccaaaatcccttaacgtgagttttcgttccactgagcgtcagaccccgta
gaaaagatcaaaggatcttcttgagatcctttttttctgcgcgtaatctgctgcttgcaaacaaaaaaaccaccgctaccagc
ggtggtttgtttgccggatcaagagctaccaactctttttccgaaggtaactggcttcagcagagcgcagataccaaatactgt
ccttctagtgtagccgtagttaggccaccacttcaagaactctgtagcaccgcctacatacctcgctctgctaatcctgttacca
```

Fig. 8N gtggctgctgccagtggcgataagtcgtgtcttaccggggttggactcaagacgatagttaccggataaggcgcagcggtcg
ggctgaacgggggggttcgtgcacacagcccagcttggagcgaacgacctacaccgaactgagatacctacagcgtgag
cattgagaaagcgccacgcttcccgaagggagaaaggcggacaggtatccggtaagcggcagggtcggaacaggag
agcgcacgagggagcttccaggggggaaacgcctggtatctttatagtcctgtcgggtttcgccacctctgacttgagcgtcg
atttttgtgatgctcgtcagggggggcggagcctatggaaaaacgccagcaacgcgagctcgatttaggtgacactata
(SEQ ID NO: 9)

Fig. 8O gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggcttttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattct
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattacctttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaataccccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaagaactagtcactgggct
agggctcacaggcgagctggtggatcctcccttccatgaattcgcctacgagagtctgagaacacgaccagccgctcctta
ccaagtaccaaccataggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttaacatgatgtgcctgaaagtgcattttaaccacgagatttgcacacaagtcttccacaaaagcatctctcgccgttgca
ctaaatctgtgacttcggtcgtcicaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcacccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggcttagtgccggtgctgaagaccgctggcatagacatgaccactgaacaatggaac
actgtggattattttgaaacggacaaagctcactcagcagagatagtattgaaccaactatgcgtgaggttctttggactcgat

Fig. 8P

```
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggtgtgcg
gagcgctgtataagaaattccnggaaagcttcgatttacagccgatcgaagtaggaaaagcgcgactggtcaaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaigactctcaaggaagcagtggctaggagagaagcagtggaggagatatgcatatccga
cgactcttcagtgacagaacctgatgcagagctggtgagggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccaccagcacgctgccttgcttgtgcatccatgccatgactccaga
aagagtacagcgcctaaaagcctcacgtccagaacaaattactgtgtgctcatcctttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggcccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagtttccaccccgccaggcgtgaataggtgatcactagagaggagctcgaggcgcttacccgtcacgcactcc
tagcaggtcggtctcgagaaccagcctggtctccaacccgccaggcgtaaataggtgattacaagagaggagtttgag
gcgttcgtagcacaacaacaatgacggtttgatgcgggtgcatacatctttcctccgacaccggtcaagggcatttacaac
aaaaatcagtaaggcaaacggtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatcagtgtgaaccgtgccttttcaagcccccaaggtcgcag
tggaagcctgtaacgccatgttgaaagagaacttccgactgtggcttcttactgtattattccagagtacgatgcctatttgga
catggttgacggagcttcatgctgcttagacactgccagttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaagaaaacccatcaggcttactgaagaaaacgtggtaaattacattaccaa
attaaaaggaccaaaagctgctgctcttttcgcgaagacacataatttgaatatgttgcaggacataccaatggacaggtttgt
aatggacttaaagagagacgtgaaagtgactccaggaacaaaacatactgaagaacggcccaaggtacaggtgatcc
aggctgccgatccgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgttctg
gaaactgacatcgcgtcgtttgataaaagtgaggacgacgccatggctctgaccgcgttaatgattctggaagacttaggtg
tggacgcagagctgttgacgctgattgaggcggcttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaaggagtcaaatcggacaaatta
atggcagacaggtgcgccacctggttgaatatggaagtcaagattatagatgctgtggtgggcgagaaagcgcctatttct
gtggagggtttattttgtgtgactccgtgaccggcacagcgtgccgtgtggcagaccccctaaaaaggctgtttaagcttggc
aaacctctggcagcagacgatgaacatgatgatgacaggagaagggcattgcatgaagagtcaacacgctggaaccg
```

Fig. 8Q agtgggtattctttcagagctgtgcaaggcagtagaatcaaggtatgaaaccgtaggaacttccatcatagttatggccatga
ctactctagctagcagtgttaaatcattcagctacctgagaggggcccctataactctctacggctaacctgaatggactacg
acatagtctagtccgccaagtctagaccatgagcggccggaaggctcagggcaagaccctgggcgtgaacatggtgag
gcgcggcgtgcgcagcctctccaacaagatcaagcagaagaccaagcagatcggcaacagacccggaccgagccg
gggcgtccagggggttcatcttcttcttcctgttcaacatcctcacaggtaagaagatcacggctcacctgaagaggctctgga
agatgctggaccctcgccaggggctcgcggtgctcagaaaggtgaagcgggtcgtcgccctccctgatgcgcggcctgtcc
tctcgcaagaggcgctcccacgatgtgctcaccgtccaattcctcattctggaatgctgctgatgactggcggcgtgaccctg
gtgcgcaagaaccgctggctgctgctgaatgtgaccagtgaggacctcgggtaagggcccctataactctctacggctaa
cctgaatggactacgacatagtctagtccgccaagtctagagcttaccatgaccgagtacaagcccacggtgcgcctcgc
cacccgcgacgacgtccccagggccgtacgcaccctcgccgccgcgttcgccgactaccccgccacgcgccacaccgt
cgatccggaccgccacatcgagcgggtcaccgagctgcagaactcttcctcacgcgcgtcgggctcgacatcggcaag
gtgtgggtcgcggacgacggcgccgcggtggcggtctggaccacgccggagagcgtcgaagcggggcggtgttcgc
cgagatcggcccgcgcatggccgagttgagcggttcccggctggccgcgcagcaacagatggaaggcctcctggcgcc
gcaccggcccaaggagcccgcgtggttcctggccaccgtcggcgtctcgcccgaccaccagggcaagggtctgggcag
cgccgtcgtgctccccggagtggaggcggccgagcgcgccggggtgcccgccttcctggagacctccgcgccccgcaa
cctcccccttctacgagcggctcggcttcaccgtcaccgccgacgtcgaggtgcccgaaggaccgcgcacctggtgcatga
cccgcaagcccggtgcctgacgcccgccccacgacccgcagcgcccgaccgaaaggagcgcacgacccccatgatcg
ctagaccatggggtaccgagtatgttacgtgcaaaggtgattgtcaccccccgaaagaccatattgtgacacaccctcagt
atcacgcccaaacatttacagccgcggtgtcaaaaaccgcgtggacgtggttaacatccctgctgggaggatcagccgta
attattataattggcttggtgctggctactattgtggccatgtacgtgctgaccaaccagaaacataattgaatacagcagcaa
ttgcaagctgcttacatagaactcgcggcgattggcatgccgccttaaaattttttattttattttttctttctttttccgaatcggatttt
gtttttaatatttcaaaaaaaaaaaaaaaaaaaaaacgcgtcgaggggaattaattcttgaagacgaaagggccag
gtggcacttttcggggaaatgtgcgcggaaccccctatttgtttatttttctaaatacattcaaatatgtatccgctcatgagacaat
aaccctgataaatgcttcaataatattgaaaaaggaagagtatgagtattcaacatttccgtgtcgcccttattccctttttgcg
gcattttgccttcctgttttgctcacccagaaacgctggtgaaagtaaaagatgctgaagatcagttgggtgcacgagtgggt
tacatcgaactggatctcaacagcggtaagatccttgagagttttcgccccgaagaacgttttccaatgatgagcacttttaaa
gttctgctatgtggcgcggtattatcccgtgttgacgccgggcaagagcaactcggtcgccgcatacactattctcagaatga
cttggttgagtactcaccagtcacagaaaagcatcttacggatggcatgacagtaagagaattatgcagtgctgccataac
catgagtgataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgacaccacg
atgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgga
gccggtgagcgtgggtctcgcggtatcattgcagcactggggccagatggtaagccctcccgtatcgtagttatctacacga
cggggagtcaggcaactatggatgaacgaaatagacagatcgctgagataggtgcctcactgattaagcattggtaactgt
cagaccaagtttactcatatatactttagattgatttaaaacttcattttaatttaaaaggatctaggtgaagatccttttgataat
ctcatgaccaaaatcccttaacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcaca
cagcccagcttggagcgaacgacctacaccgaactgagatacctacagcgtgagcattgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcagggggcg
gagcctatggaaaaacgccagcaacgcgagctcgatttaggtgacactata (SEQ ID NO: 10)

Fig. 8R

```
gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattctt
agaaagaagtatttgaaaccatccaacaatgttcattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttggctttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctccta
ccaagtaccaaccatagggtgtatggcgtgccaggatcaggcaagtctggcatcattaaaagcgcagtcaccaaaaaa
gatctagtggtgagcgccaagaaagaaaactgtcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcgggggatcccaaacagtgcgg
ttttttttaacatgatgtgcctgaaagtgcattttaaccacgagatttgcacacaagtcttccacaaaagcatctctcgccgttgca
ctaaatctgtgacttcggtcgtctcaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgatatgacggcagctgcctctcaagggctgacccgtaaaggtgtgtatgccgttcggtacaa
ggtgaatgaaaatcctctgtacgcacccaccctcagaacatgtgaacgtcctactgacccgcacggaggaccgcatcgtgt
ggaaaacactagccggcgacccatggataaaaacactgactgccaagtaccctgggaatttcactgccacgatagagg
agtggcaagcagagcatgatgccatcatgaggcacatcttggagagaccggaccctaccgacgtcttccagaataaggc
aaacgtgtgttgggccaaggctttagtgccggtgctgaagaccgctggcatagacatgaccactgaacaatggaacactg
tggattattttgaaacggacaaagctcactcagcagagatagtattgaaccaactatgcgtgaggttctttggactcgatctgg
actccggtctattttctgcacccactgttccgttatccattaggaataatcactgggataactccccgtcgcctaacatgtacgg
gctgaataaagaagtggtccgtcagctctctcgcaggtacccacaactgcctcgggcagttgccactggaagagtctatga
catgaacactggtacactgcgcaattatgatccgcgcataaacctagtacctgtaaacagaagactgcctcatgctttagtc
ctccaccataatgaacacccacagagtgacttttcttcattcgtcagcaaattgaagggcagaactgtcctggtggtcgggg
aaaagttgtccgtcccaggcaaaatggttgactggttgtcagaccggcctgaggctaccttcagagctcggctggatttagg
catcccaggtgatgtgcccaaatatgacataatatttgttaatgtgaggaccccatataaataccatcactatcagcagtgtg
aagaccatgccattaagcttagcatgttgaccaagaaagcttgtctgcatctgaatcccggcggaacctgtgtcagcatagg
ttatggttacgctgacagggccagcgaaagcatcattggtgctatagcgcggcagttcaagttttcccgggtatgcaaaccg
aaatcctcacttgaagagacggaagttctgtttgtattcattgggtacgatcgcaaggcccgtacgcacaatccttacaagctt
tcatcaaccttgaccaacatttatacaggttccagactccacgaagccggatgtgcaccctcatatcatgtggtgcgaggg
atattgccacgccaccgaaggagtgattataaatgctgctaacagcaaaggacaacctggcggaggggtgtgcggag
```

Fig. 8S cgctgtataagaaattcccggaaagcttcgatttacagccgatcgaagtaggaaaagcgcgactggtcaaaggtgcagct
aaacatatcattcatgccgtaggaccaaacttcaacaaagtttcggaggttgaaggtgacaaacagttggcagaggcttat
gagtccatcgctaagattgtcaacgataacaattacaagtcagtagcgattccactgttgtccaccggcatcttttccgggaa
caaagatcgactaacccaatcattgaaccatttgctgacagctttagacaccactgatgcagatgtagccatatactgcagg
gacaagaaatgggaaatgactctcaaggaagcagtggctaggagagaagcagtggaggagatatgcatatccgacga
ctcttcagtgacagaacctgatgcagagctggtgaggtgcatccgaagagttctttggctggaaggaagggctacagca
caagcgatggcaaaactttctcatatttggaagggaccaagtttcaccaggcggccaaggatatagcagaaattaatgcc
atgtggcccgttgcaacggaggccaatgagcaggtatgcatgtatatcctcggagaaagcatgagcagtattaggtcgaa
atgccccgtcgaagagtcggaagcctccacaccacctagcacgctgccttgcttgtgcatccatgccatgactccagaaag
agtacagcgcctaaaagcctcacgtccagaacaaattactgtgtgctcatcctttccattgccgaagtatagaatcactggtg
tgcagaagatccaatgctcccagcctatattgttctcaccgaaagtgcctgcgtatattcatccaaggaagtatctcgtggaa
acaccaccggtagacgagactccggagccatcggcagagaaccaatccacagaggggacacctgaacaaccacca
cttataaccgaggatgagaccaggactagaacgcctgagccgatcatcatcgaagaggaagaagaggatagcataagt
ttgctgtcagatggcccgacccaccaggtgctgcaagtcgaggcagacattcacgggccgccctctgtatctagctcatcct
ggtccattcctcatgcatccgactttgatgtggacagtttatccatacttgacaccctggagggagctagcgtgaccagcggg
gcaacgtcagccgagactaactcttacttcgcaaagagtatggagtttctggcgcgaccggtgcctgcgcctcgaacagta
ttcaggaaccctccacatcccgctccgcgcacaagaacaccgtcacttgcacccagcagggcctgctcgagaaccagcc
tagtttccaccccgccaggcgtgaataggtgatcactagagaggagctcgaggcgcttaccccgtcacgcactcctagc
aggtcggtctcgagaaccagctggtctccaacccgccaggcgtaaataggtgattacaagagaggagtttgaggcgttc
gtagcacaacaacaatgacggtttgatgcgggtgcatacatctttcctccgacaccggtcaagggcatttacaacaaaaat
cagtaaggcaaacggtgctatccgaagtggtgttggagaggaccgaattggagatttcgtatgccccgcgcctcgaccaa
gaaaaagaagaattactacgcaagaaattacagttaaatcccacacctgctaacagaagcagataccagtccaggaag
gtggagaacatgaaagccataacagctagacgtattctgcaaggcctagggcattatttgaaggcagaaggaaaagtgg
agtgctaccgaaccctgcatcctgttcctttgtattcatcagtgtgaaccgtgccttttcaagccccaaggtcgcagtggaagc
ctgtaacgccatgttgaaagagaactttccgactgtggcttcttactgtattattccagagtacgatgcctatttggacatggttg
acggagcttcatgctgcttagacactgccagttttttgccctgcaaagctgcgcagcttttccaaagaaacactcctatttggaac
ccacaatacgatcggcagtgccttcagcgatccagaacacgctccagaacgtcctggcagctgccacaaaaagaaattg
caatgtcacgcaaatgagagaattgcccgtattggattcggcggccttaatgtggaatgcttcaagaaatatgcgtgtaata
atgaatattgggaaacgtttaaagaaaaccccatcaggcttactgaagaaaacgtggtaaattacattaccaaattaaaag
gaccaaaagctgctgctcttttgcgaagacacataatttgaatatgttgcaggacataccaatggacaggtttgtaatggact
taaagagagacgtgaaagtgactccaggaacaaaacatactgaagaacggcccaaggtacaggtgatccaggctgcc
gatccgctagcaacagcgtatctgtgcggaatccaccgagagctggttaggagattaaatgcggtcctgcttccgaacattc
atacactgtttgatatgtcggctgaagactttgacgctattatagccgagcacttccagcctggggattgtgttctggaaactga
catcgcgtcgtttgataaaagtgaggacgacgccatggctctgaccgcgttaatgattctggaagacttaggtgtggacgca
gagctgttgacgctgattgaggcggcttcggcgaaatttcatcaatacatttgcccactaaaactaaatttaaattcggagcc
atgatgaaatctggaatgttcctcacactgtttgtgaacacagtcattaacattgtaatcgcaagcagagtgttgagagaacg
gctaaccggatcaccatgtgcagcattcattggagatgacaatatcgtgaaaggagtcaaatcggacaaattaatggcag
acaggtgcgccacctggttgaatatggaagtcaagattatagatgctgtggtgggcgagaaagcgccttatttctgtggagg
gtttattttgtgtgactccgtgaccggcacagcgtgccgtgtggcagaccccctaaaaaggctgtttaagcttggcaaaccct
ggcagcagacgatgaacatgatgatgacaggagaagggcattgcatgaagagtcaacacgctggaaccgagtgggta
ttctttcagagctgtgcaaggcagtagaatcaaggtatgaaaccgtaggaacttccatcatagttatggccatgactactcta
gctagcagtgttaaatcattcagctacctgagaggggcccctataactctctacggctaacctgaatggactacgacatagt
ctagtccgccaagtctagaccatgagcggccggaaggctcagggcaagaccctgggcgtgaacatggtgaggcgcgg
cgtgcgcagcctctccaacaagatcaagcagaagaccaagcagatcggcaacagacccggaccgagccggggcgtc
cagggggttcatcttcttcttcctgttcaacatcctcacaggtaagaagatcacggctcacctgaagaggctctggaagatgct
ggaccctcgccaggggctcgcggtgctcagaaaggtgaagcgggtcgtcgcctccctgatgcgcggcctgtcctctcgca
agaggcgctcccacgatgtgctcaccgtccaattcctcattctgggaatgctgttgatgacgggtggagtgaccttggtgcgg
aaaaacagatggttgctcctaaatgtgacatctgaggacctcgggaaaacattctctgtgggcacaggcaactgcacaac
aaacattttggaagccaagtactggtgcccagactcaatggaatacaactgtcccaatctcagtccaagagaggagccag
atgacattgattgctggtgctatgggtggaaaacgttagagtcgcatatggtaagtgtgactcagcaggcaggtctaggag
gtcaagaagggccattgacttgcctacgcatgaaaaccatggtttgaagacccggcaagaaaaatggatgactggaaga

Fig. 8T

```
atgggtgaaaggcaactccaaaagattgagagatggttcgtgaggaaccccttttttgcagtgacggctctgaccattgcct
accttgtgggaagcaacatgacgcaacgagtcgtgattgccctactggtcttggctgttggtccggcctactcagctcactgc
attggaattactgacagggatttcattgaggggtgcatggaggaacttgggtttcagctaccctggagcaagacaagtgtg
tcactgttatggcccctgacaagccttcattggacatctcactagagacagtagccattgatagacctgctgaggtgaggaa
agtgtgttacaatgcagttctcactcatgtgaagattaatgacaagtgccccagcactggagaggcccacctagctgaaga
gaacgaaggggacaatgcgtgcaagcgcacttattctgatagaggctggggcaatggctgtggcctatttgggaagggg
agcattgtggcatgcgccaaattcacttgtgccaaatccatgagtttgtttgaggttgatcagaccaaaattcagtatgtcatca
gagcacaattgcatgtaggggccaagcaggaaaattggaataccgacattaagactctcaagtttgatgccctgtcaggct
cccaggaagtcgagttcattgggtatggaaaagctacactggaatgccaggtgcaaactgcggtggactttggtaacagtt
acatcgctgagatggaaacagagagctggatagtggacagacagtgggcccaggacttgaccctgccatggcagagtg
gaagtggcggggtgtggagagagatgcatcatcttgtcgaatttgaacctccgcatgccgccactatcagagtactggccct
gggaaaccaggaaggctccttgaaaacagctcttactggcgcaatgagggttacaaaggacacaaatgacaacaacct
ttacaaactacatggtggacatgtttcttgcagagtgaaattgtcagctttgacactcaaggggacatcctacaaaatatgca
ctgacaaaatgttttttgtcaagaacccaactgacactggccatggcactgttgtgatgcaggtgaaagtgtcaaaaggagc
cccctgcaggattccagtgatagtagctgatgatcttacagcggcaatcaataaaggcattttggttacagttaaccccatcg
cctcaaccaatgatgatgaagtgctgattgaggtgaacccaccttttggagacagctacattatcgttgggagaggagattc
acgtctcacttaccagtggcacaaagagggaagctcaataggaaagttgttcactcagaccatgaaaggcgtggaacgc
ctggccgtcatgggagacaccgcctgggatttcagctccgctggagggttcttcacttcggttgggaaaggaattcatacggt
gtttggctctgcctttcaggggctatttggcggcttgaactggataacaaaggtcatcatgggggcggtacttatatgggttggc
atcaacacaagaaacatgacaatgtccatgagcatgatcttggtaggagtgatcatgatgttttgtctctaggagttggggc
gtaagcggcccctataactctctacggctaacctgaatggactacgacatagtctagtccgccaagtctagagcttaccatg
accgagtacaagcccacggtgcgcctcgccacccgcgacgacgtccccagggccgtacgcaccctcgccgccgcgttc
gccgactaccccgccacgcgccacaccgtcgatccggaccgccacatcgagcgggtcaccgagctgcaagaactcttc
ctcacgcgcgtcgggctcgacatcggcaaggtgtgggtcgcggacgacggcgccgcggtggcggtctggaccacgccg
gagagcgtcgaagcgggggcggtgttcgccgagatcggcccgcgcatggccgagttgagcggttcccggctggccgcg
cagcaacagatggaaggcctcctggcgccgcaccggcccaaggagcccgcgtggttcctggccaccgtcggcgtctcg
cccgaccaccagggcaagggtctgggcagcgccgtcgtgctcccgggagtggaggcggccgagcgcgccggggtgc
ccgccttcctggagacctccgcgccccgcaacctcccccttctacgagcggctcggcttcaccgtcaccgccgacgtcgag
gtgcccgaaggaccgcgcacctgatgcatgacccgcaagcccggtgcctgacgcccgccccacgacccgcagcgccc
gaccgaaaggagcgcacgaccccatgatcgctagaccatggggtaccgagtatgttacgtgcaaaggtgattgtcaccc
cccgaaagaccatattgtgacacaccctcagtatcacgcccaaacatttacagccgcggtgtcaaaaaccgcgtggacgt
ggttaacatccctgctgggaggatcagccgtaattattataattggcttggtgctggctactattgtggccatgtacgtgctgac
caaccagaaacataattgaatacagcagcaattggcaagctgcttacatagaactcgcggcgattgcatgccgcccttaaa
atttttattttattttttcttttcttttccgaatcggattttgtttttaatatttcaaaaaaaaaaaaaaaaaaaaaaaacgcgtcgag
gggaattaattcttgaagacgaaagggccaggtggcacttttcggggaaatgtgcgcggaaccccctatttgtttatttttctaaa
tacattcaaatatgtatccgctcatgagacaataaccctgataaaatgcttcaataatattgaaaaaggaagagtatgagtatt
caacatttccgtgtcgcccttattccctttttgcggcattttgccttcctgttttgctcacccagaaacgctggtgaaagtaaaag
atgctgaagatcagttgggtgcacgagtgggttacatcgaactggatctcaacagcggtaagatccttgagagttttcgccc
cgaagaacgttttccaatgatgagcacttttaaagttctgctatgtggcgcggtattatcccgtgttgacgccgggcaagagc
aactcggtcgccgcatacactattctcagaatgacttggttgagtactcaccagtcacagaaaagcatcttacggatggcat
gacagtaagagaattatgcagtgctgccataaccatgagtgataacactgcggccaacttacttctgacaacgatcggag
gaccgaaggagctaaccgcttttttgcacaacatgggggatcatgtaactcgccttgatcgttgggaaccggagctgaatg
aagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggc
ccttccggctggctggtttattgctgataaatctggagccggtgagcgtgggtctcgcggtatcattgcagcactggggccag
atggtaagccctcccgtatcgtagttatctacacgacggggagtcaggcaactatggatgaacgaaatagacagatcgct
gagataggtgcctcactgattaagcattggtaactgtcagaccaagtttactcatatatactttagattgatttaaaacttcatttt
aatttaaaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccacc
gctaccagcggtggtttgtttgccggatcaagagctaccaactctttttccgaaggtaactggcttcagcagagcgcagatac
caaatactgtccttctagtgtagccgtagttaggccaccacttcaagaactctgtagcaccgcctacatacctcgctctgctaa
```

Fig. 8U tcctgttaccagtggctgctgccagtggcgataagtcgtgtcttaccgggttggactcaagacgatagttaccggataaggcg
cagcggtcgggctgaacgggggttcgtgcacacagcccagcttggagcgaacgacctacaccgaactgagataccta
cagcgtgagcattgagaaagcgccacgcttcccgaagggagaaaggcggacaggtatccggtaagcggcagggtcg
gaacaggagagcgcacgacggagcttccaggggaaacgcctggtatctttatagtcctgtcgggtttcgccacctctgac
ttgagcgtcgattttgtgatgctcgtcagggggcggagcctatggaaaaacgccagcaacgcgagctcgatttaggtga
cactata (SEQ ID NO: 11)

Fig. 8V

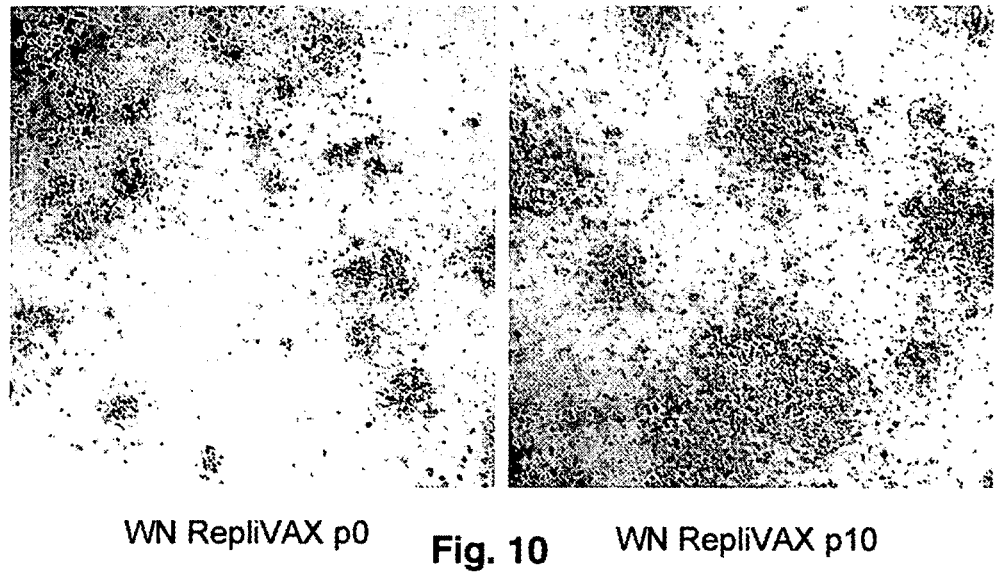
WN RepliVAX p0  Fig. 10  WN RepliVAX p10

PSEUDOINFECTIOUS FLAVIVIRUS AND USES THEREOF

This application is a Continuation of U.S. patent application Ser. No. 11/711,532 filed Feb. 27, 2007 (currently pending), which is a non-provisional application of U.S. Provisional Application No. 60/777,189 filed Feb. 27, 2006. Priority is claimed to all the above referenced applications and the content of each of the above-referenced applications is incorporated herein by reference in its entirety.

FEDERAL FUNDING LEGEND

This invention was produced in part using funds obtained through National Institute of Health grants (R01AI053135 and 1U54AI057156-010004). Consequently, the federal government has certain rights in this invention.

BACKGROUND OF THE INVENTION

1. Field of the Invention

The present invention relates to the fields of molecular biology, virology and immunology. In general, the present invention discloses construction of replication-deficient viruses belonging to the Flaviviridae family and their use as vaccine in prevention of diseases caused by viruses belonging to this family. More specifically, the present invention provides replication-deficient flaviviruses or pseudoinfectious flaviviruses (PIV aka RepliVAX) and discloses its use as preventive vaccines against flavivirus-associated diseases.

2. Description of the Related Art

The Flavivirus genus of the Flaviviridae family contains a variety of important human and animal pathogens and have been classified into four distinct antigenic complexes based on differences in reactivity in immunological tests. Generally, the flaviviruses circulate between avian or mammalian amplifying hosts and mosquito or tick vectors.

The flavivirus genome is a single-stranded capped RNA of positive polarity lacking a 3' terminal poly(A) sequence. It encodes a single polypeptide that is co- and post-translationally processed into viral structural proteins, C, prM/M, and E, forming viral particles, and the nonstructural proteins, NS1, NS2A, NS2B, NS3, NS4A, NS4B and NS5, required for replication of viral genome and its packaging into infectious virions (Chambers, 1990). Virions contain a single copy of viral genomic RNA packaged into a C protein-containing nucleocapsid, surrounded by lipid envelope holding heterodimers of M and E proteins. In contrast to many other enveloped viruses, interaction between nucleocapsid and envelope spikes is not very specific and M/E-containing envelope can efficiently form around nucleocapsid derived from heterologous flavivirus, demonstrating limited level of homology in capsid sequence (Lorenz, 2002). Alternatively, expression of prM and E in the absence of C can lead to formation of subviral particles (SVPs), containing no RNA or C protein (Mason, 1991).

PrM/M-E cassettes producing subviral particles have been the basis of several vaccine candidates that are known in the art. These vaccine candidates include subunit (Konishi, 1992; 2001; 2002; Qiao, 2004), DNA (Phillpotts, 1996; Kochel, 1997; Schmaljohn, 1997; Colombage, 1998; Aberle, 1999; Konishi, 2000; Konishi, 2000; Kochel, 2000; Davis, 2001), and live-vectored (Mason, 1991; Konishi, 1992; Pincus, 1992; Fonseca, 1994; Pugachev, 1995; Colombage, 1998; Kanesa, 2000; Minke, 2004) vaccines. However, these vaccines have serious disadvantages. For instance, the subunit vaccines are safe to use but difficult to produce large quantities; the DNA vaccines are poorly immunogenic, and the viral vectored vaccines suffer from lack of potency in the presence of vector immunity.

Therefore, in spite of a great concern about flavivirus-associated diseases and continuing spread of the flaviviruses into the new areas, antiviral therapeutics have not yet been developed for these infections, and a very limited number of approved vaccines have been produced to-date. Inactivated viral vaccines (INVs) have been licensed to prevent tick-borne encephalitis (TBEV) and Japanese encephalitis (JEV). However, like other inactivated viral vaccines, these vaccines have low limited potency and require multiple vaccinations. Despite these drawbacks the Japanese encephalitis and tick-borne encephalitis INVs have an advantage of good safety records. The only licensed live-attenuated vaccine (LAV) for a flavivirus is the widely utilized live-attenuated vaccine based on the yellow fever virus (YFV) 17D strain that was developed by serial passaging of the wild type Asibi strain of yellow fever virus in chicken embryo tissues. Although this live-attenuated vaccine is considered very safe and effective, cases of yellow fever in vaccinees have been reported, including a recent case in a US military recruit (Gerasimon, 2005). Furthermore, this vaccine is not recommended for use in infants, pregnant women or the immunocompromised individuals due to adverse effects, including vaccine-associated encephalitis.

However, the development of the reverse genetics systems for flaviviruses has led to the production and designing of new types of live-attenuated vaccine, based on rational attenuation of these viruses. This new class of vaccines includes yellow fever virus 17D-based chimeras, in which the yellow fever virus prM-E-encoding genome fragment cassette has been replaced with the prM-E-cassette derived from heterologous flaviviruses (Chambers, 1999). Similar chimeric virus-based approach was applied for dengue- and TBE-based backbones (Pletnev, 2002; Huang, 2003). In most cases, chimeric flaviviruses demonstrate a highly attenuated phenotype and are capable of eliciting efficient protective immune response and protect against following infection with viruses, whose structural proteins are expressed by the chimeras (Monath, 2002). Effective vaccination with these chimeric vaccine candidates appears not to be prevented by pre-existing "vector" immunity (Monath, 2002), which has interfered with potency of recombinant viral vaccines based on other viral vectors. Further, although chimeric flaviviruses might provide a reasonably universal approach to producing new vaccines, there are concerns that the chimeras themselves might be pathogenic (Chambers, 1999) at least in the immunocompromised individuals, or that pathogenic chimeras might arise, since mutations have been detected during the process of propagation of these viruses (Pugachev, 2004).

Another promising direction in vaccine development is based on creating of irreparable deletions in flavivirus genome that make productive virus replication in the vaccinated host either a less efficient or an impossible event. In the latter case, viral genomes encoding the entire replicative machinery, but lacking, for instance, the C-coding region, can be delivered for in vivo immunization either as in vitro-synthesized RNA, capable of self-replication (Kofler, 2004; Aberle, 2005), or, probably, in DNA form (under control of the RNA polymerase II promoters or as in vitro-synthesized RNA, capable of self-replication (Kofler, 2004; Aberle, 2005). Direct immunization with in vitro synthesized defective RNA genomes, which specifies the production of SVPs in the absence of a complete viral replication cycle, has been demonstrated to be safe and effective in producing protective immunity (Kofler, 2004; Aberle, 2005). However, there may be significant obstacles in producing an RNA-based vaccine candidate, due to synthesis, stability, and delivery issues.

Thus, prior art is deficient is deficient in a safe, potent and effective type of vaccine that can be used against diseases caused by infection with viruses belonging to the Flaviviridae family. The present invention fulfills this long-standing need and desire in the art.

SUMMARY OF THE INVENTION

In one embodiment of the present invention, there is provided a replication-deficient pseudoinfectious virus of Flaviviridae family. Such a replication-deficient pseudoinfectious virus comprises: a deletion in the nucleotide sequence encoding capsid (C) protein such that the deletion does not disrupt the RNA sequence required for genome cyclization, the signal sequence for prM protein that is required for the proper maturation of prM/M or a combination thereof, where the replication-deficient pseudoinfectious virus replicates only in cells expressing C protein or C, prM, envelope protein, mutated C protein, mutated prM, mutated envelope protein or combinations thereof of the virus of the Flaviviridae family.

In another related embodiment of the present invention, there is provided a cell culture system expressing C protein or C, prM, envelope protein, mutated C protein, mutated prM, mutated envelope protein or combinations thereof of the virus of the Flaviviridae family effective to enable propagation of the above-described replication-deficient pseudoinfectious virus of the Flaviviridae family under suitable conditions.

In yet another embodiment of the present invention, there is provided a method of producing the replication-deficient pseudoinfectious virus of the Flaviviridae family described above. Such a method comprises generating a replication-deficient pseudoinfectious virus of the Flaviviridae family that comprises deletion in the capsid gene such that the deletion does not disrupt the RNA sequence required for genome cyclization, the signal sequence for prM protein that is required for the proper maturation of prM/M or a combination thereof; generating a cell line that expresses C protein or C, prM, envelope protein, mutated C protein, mutated prM, mutated envelope protein or combinations thereof of the virus of the Flaviviridae family, where the cell line provides high levels of the proteins of the Flaviviridae needed for propagation of the replication-deficient pseudoinfectious virus of the Flaviviridae family; and infecting the cell line with the pseudoinfectious virus of the Flaviviridae family, thereby producing the replication-deficient pseudoinfectious virus of the Flaviviridae family.

In another related embodiment of the present invention, there is provided a pharmaceutical composition, comprising the replication-deficient pseudoinfectious virus of the Flaviviridae family produced by the method described herein.

In a further related embodiment of the present invention, there is provided a method of protecting a subject from infections resulting from exposure to Flaviviridae. Such a method comprises administering to the subject an immunologically effective amount of the pharmaceutical composition produced by the method described herein, that elicits an immune response against the Flaviviridae in the subject, thereby protecting the subject from the infections.

BRIEF DESCRIPTION OF THE DRAWINGS

FIGS. 2A-2C show that YFV C and YFV C, prM and E-expressing cell lines can complement replication of YF PIV. FIG. 2A is a schematic representation of YFV and GFP-expressing YF PIV genome. FIG. 2B is a schematic representation of VEEV replicons expressing Pac gene and YFV C with the signal peptide of prM (anchored C; VEErep/C1/Pac), or anchored C with 20 a. a. of prM (VEErep/C2/Pac), or all of the YFV structural proteins (VEErep/C-prM-E/Pac). FIG. 2C shows the release of YF PIV by the cell lines transfected with in vitro-synthesized PIV genome. Media was replaced at the indicated time points, and titers of PIVs were determined. Arrows indicate time points when cells were subpassaged at a 1:5 ratio.

FIGS. 3A-3B show growth curves of YF PIV on the packaging cell lines. BHK-21 cells containing VEErep/C2/Pac and VEErep/C-prM-E/Pac replicons were infected with YF PIV at indicated MOIs in infectious units per cell. At the indicated times, media was replaced and titers of released PIV were determined. Arrows indicate time points when cells were subpassaged at 1:5 ratio. FIG. 3A shows growth curve at MOI 10 inf.u/cell and FIG. 3B shows growth curve at MOI 0.1 inf.u/cell.

FIGS. 4A-4C show that cells expressing codon-optimized C gene produced YF PIV. FIG. 4A shows the nucleotide sequence of synthetic gene. The introduced mutations are indicated by lowercase letters (SEQ ID NO: 1). FIG. 4B shows growth curves of YF PIV on the packaging cell lines. BHK-21 cells containing VEErep/C2/Pac, VEErep/C-prM-E/Pac, VEErep/C2opt/Pac and VEErep/Copt-prM-E/Pac replicons were infected with YF PIV at indicated MOIs in infectious units per cell. At the indicated times, media was replaced and titers of released PIV were determined. FIG. 4C shows plaques developed in VEErep/C2opt/Pac-containing cell line by YFV and YF PIV after 4 days of incubation at 37° C.

FIGS. 5A-5C show that WN PIV develops spreading infection in packaging cells. FIG. 5A is a schematic representation of WN PIV genome and VEEV replicon expressing WNV structural genes. FIG. 5B shows that WN PIV produced foci of WNV antigen-positive cells (revealed with an antibody to NS1-upon infection of BHK(VEErep/C*-E*-Pac) cells after 70 hours of incubation. FIG. 5C shows the same WN PIV preparations produced only single infected cells (revealed at 70 hours post infection with the same tragacanth staining method used in FIG. 5B) upon infection of Vero cell monolayers.

FIGS. 6A-6C show detection of E protein upon release from cells infected with YF and WN PIVs. In FIG. 6A, BHK-21 cells were infected with YF PIV at an MOI of 5 inf.u/cell. The released SVPs were harvested and purified by ultracentrifugation. Samples were resolved by SDS PAGE, transferred to filters, E protein was detected by D1-4G2 MAB. Media harvested from uninfected cells, lane 1; media harvested from the cells infected with YF PIV at 48 h post infection, lane 2; media harvested from the cells infected with YF PIVs at 72 h post infection, lane 3; YFV ($2 \times 10^7$ PFU), lane 4. In FIG. 6B, vero cells were infected with WN PIV for 24 hrs, and then portions of the clarified culture fluid (collected before any cell lysis was detected), were resolved by SDS PAGE, transferred to filters, and reacted with an E-specific MAB (7H2; Bioreliance). Reaction of the same samples with polyclonal sera failed to reveal any cell-associated non-structural proteins in this preparation (results not shown) confirming that the E protein was actively secreted. Sample of WNV, lane 1; media harvested from uninfected cells, lane 2; media harvested from the cells infected with WN PIV at 48 h post infection, lane 3. In FIG. 6C, a western blot showing E protein content of fractions prepared form a sucrose density gradient obtained from SVPs harvested from normal (non-packaging) BHK cells electroporated with YFV PIV RNA. The peak of E protein reactivity (at 32% sucrose) corresponded to the density of SVPs and in agreement with this fact, migrated more slowly than YFV run in a side-by-side analyses (42%).

FIG. 7A shows pYFPIV, FIG. 7B shows pWNPIV, FIG. 7C shows pVEErep/C1/Pac, FIG. 7D shows pVEErep/C2/Pac, FIG. 7E shows pVEErep/C3/PAc, FIG. 7F shows pVEErep/C*-E*-Pac.

FIGS. 8A-8V show the sequences of the plasmids used herein. FIGS. 8A-8D shows sequence of pYFPIV (SEQ ID NO: 6), FIGS. 8E-8H shows sequence of pVEErep/C1/Pac (SEQ ID NO: 7), FIGS. 8I-8K shows sequence of pVEErep/C2/Pac (SEQ ID NO: 8), FIGS. 8L-8O shows sequence of pVEErep/C-prM-E/Pac (SEQ ID NO: 9), FIGS. 8P-8R shows sequence of pVEErep/C2opt/pac (SEQ ID NO: 10), FIGS. 8S-8V shows sequence of pVEErep/Copt-prM-E/Pac (SEQ ID NO:11).

FIG. 10 shows side by side comparison of infectious foci produced in the C-expressing cell line {BHK(VEErep/Pac-Ubi-C*)} by WN RepliVAX at passage 0 (from electroporation) and passage 10 reveals that better-growing variants are readily selected.

FIG. 11 shows titration of RepliVAX PIV produced in WHO-certified Vero cells containing a C-expression cassette (VEErep/Pac-Ubi-C*). Although the resulting PIV is of a slightly lower titer than that produced in BHK cells, the Vero cells multiple harvests of high titer PIV, which is not possible with BHK cells.

FIG. 12A shows replication of WNV/IRES-RLuc replicon with single-base, matching CS mutations demonstrates that some single-base mutations replicate at WT levels. Left part of panel shows the test genome above the 5' and 3' CS sequences. Right side shows replication levels detected using Rluc reporter, as a percentage of the WT replication levels. Underlined bases denotes mutated bases. FIG. 12B shows replication of WNV/IRES-RLuc replicon with matching the double-base changes (m17) derived by combining m10 and m13 (Panel A), compared to replication levels detected with mutants that combine the WT and mutated CS in either possible format, along with a mutant designed to produce an inactive polymerase (negative control). Left part of panel shows the test genome above the 5' and 3' CS sequences. Right side shows replication levels detected using Rluc reporter, as a percentage of the WT replication levels. Underlined bases denotes mutated bases. * denotes no replication detected.

DETAILED DESCRIPTION OF THE INVENTION

Figure 1:
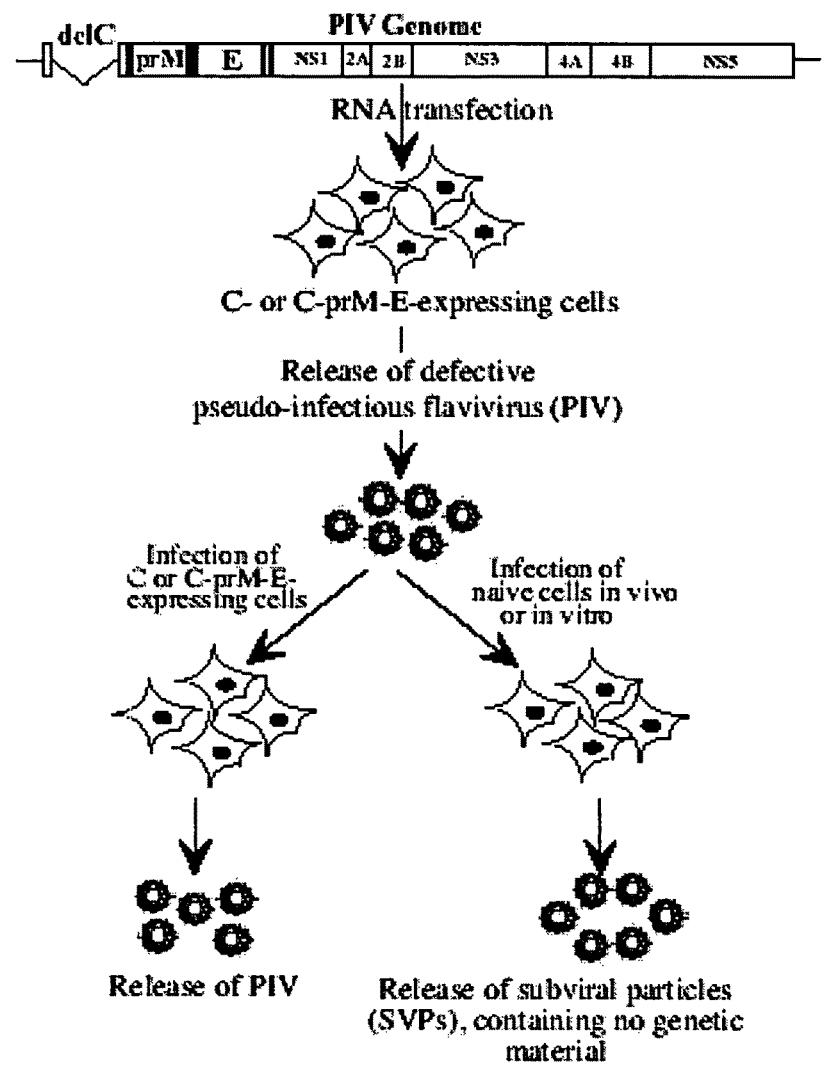
FIG. 1 is a schematic representation of flavivirus PIV replication in the cells producing C or all of the viral structural proteins for trans-complementation of the defect. Replication of PIVs in normal cells in vivo or in vitro leads to release SVPs having no nucleocapsid.
Figure 7A:
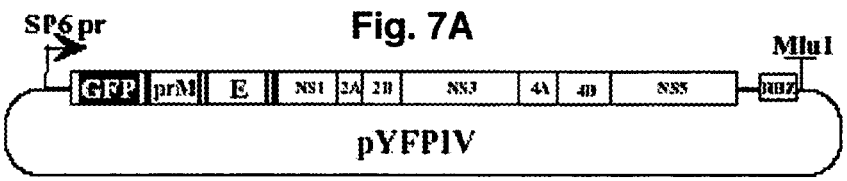
FIGS. 7A-7F show schematic representation of plasmids used for Yellow fever (YF) and West Nile (WN) pseudoinfectious virus (PIV) production.
Figure 7B:
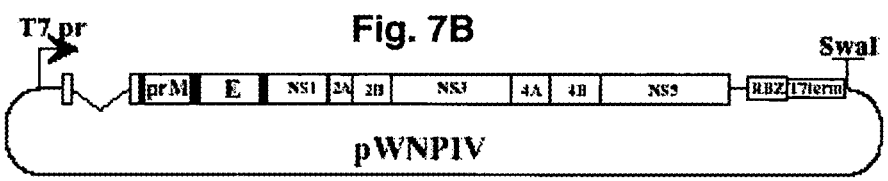
Figure 7C:
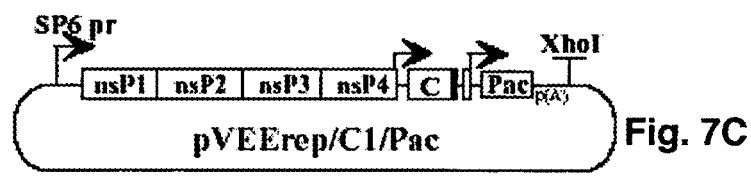
Figure 7D:
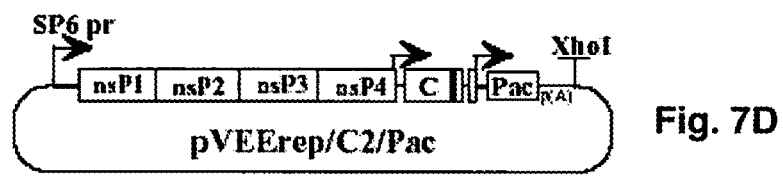
Figure 7E:
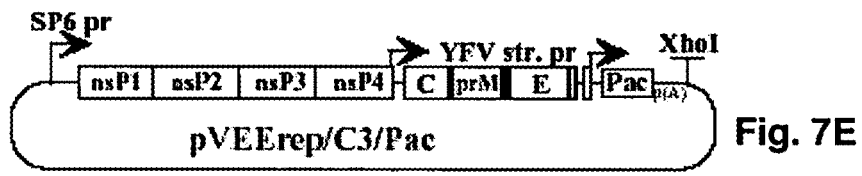
Figure 7F:
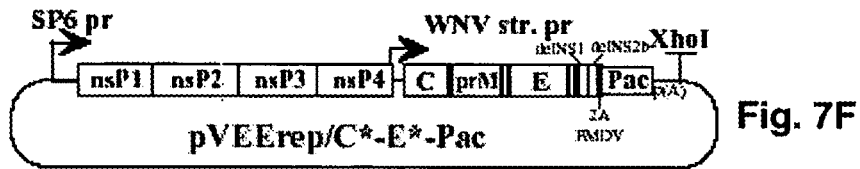

Safe and effective vaccines have only been produced for a handful of diseases caused by flaviviruses. The classical inactivated viral vaccine (INV) and live-attenuated vaccine (LAV) methods that have been used to produce vaccines to YF, JE, and TBEV have not yet yielded licensed products to prevent diseases caused by other flaviviruses, notably dengue and West Nile encephalitis (WNE). There remain safety concerns about existing LAVs (residual virulence or reversion to virulence) and INV products (reactogenicity due to antigen load and adventitious antigens). Additionally, INVs usually require multiple vaccinations. Further, both types of vaccines are subject to production concerns, including the need to avoid reversion to virulence during propagation of live-attenuated vaccine, and due to the amounts of material needed to produce strong immune responses to the inactivated viral vaccine products and the need for high containment facilities to propagate the virulent viruses used to produce INV products. Although there are promising candidates for new types of flavivirus vaccines, the road to their development will need to overcome these problems.

The present invention in general, is drawn to construction and utilization of replication-deficient pseudoinfective viruses belonging to the Flaviviridae family. In this regard, the present invention describes the development a new type of replication-deficient flaviviruses also referred to as RepliVAX that combines the safety of inactivated vaccines with the efficacy and scalability of live attenuated vaccines. These flaviviruses also identified as pseudo-infectious viruses (PIVs) in the present invention contain genetically engineered flavivirus genomes with a deletion of most of the capsid (C)-encoding region, thereby preventing this genome from producing infectious progeny in normal cell lines or vaccinated animals. However, these pseudo-infectious viruses can be propagated in cell lines expressing either C, or a C-prM-E cassette, where they replicate to high levels. Thus, these pseudoinfectious flaviviruses cannot develop spreading infection in normal cells in vitro or in vivo due to lack of trans-complementation by C protein, and therefore are incapable of causing disease in animals.

In contrast to the vaccines and the methods to generate these vaccines that are known in the art, the present invention provides a system for industrial-scale production of pseudo-infectious flaviviruses that would make such vaccines cheaper to produce than inactivated vaccines at the same time making it safer to use than live-attenuated vaccines. It does so by providing a new type of recombinant vaccine that is capable of only single round of replication in the immunized animals or humans leading to release of subviral particles (SVPs) lacking the genetic material but serving as efficient immunogens.

The present invention has demonstrated that pseudoinfectious flaviviruses can be generated for either yellow fever virus (YFV) or West Nile virus (WNV). Based on this, the present invention contemplates that the method described herein could be broadly applicable to the development of vaccines against other flaviviruses. Further, infection of normal cell lines with such pseudoinfectious flaviviruses produced SVPs that lacked nucleocapsid and a genetic material. The pseudoinfectious flaviviruses described herein demonstrated inability to cause any disease and thus were safe. Additionally, these pseudoinfectious flaviviruses were immunogenic in mice due to competency for single round of replication and release of SVPs, presenting viral antigens. WN PIVs also protected mice from a lethal encephalitis following challenge with WNV.

The PIVs described herein could be produced in a manner that allows for high-yield production in cell culture, and inability to cause disease in animals. These products could be delivered to animals where their defective replication process prevents spread and disease, but permitted the production of SVPs, a flavivirus subunit immunogen that has been shown to be effective in eliciting an efficacious immune response against disease caused by several flaviviruses.

The present invention also demonstrated that the pseudo-infectious flaviviruses approach could be applied to two distantly related mosquito-borne flaviviruses. The applicability of a similar technology to the development of RNA-based vaccines for a tick-borne flavivirus (Kofler, 2004) indicates that the PIV-based technology will be applicable to more distantly related flaviviruses. Additionally, the work with TBEV RNA-based vaccines indicates that in addition to antibody responses to the SVPs (similar to that described herein), the introduction of replicationally active flavivirus genomes into the cells of the vaccinated hosts will produce T-cell responses as well (Kofler, 2004; Aberle, 2005). Although the T cell responses were not measured herein, it is contemplated that the PIVs are capable of inducing T cell response that mimics those produced by viral infection.

Although the PIV vaccines described herein rely on the same flavivirus replication and SVP production strategy that was utilized by the RNA-based vaccines prepared for TBEV (Kofler, 2004; Aberle, 2005), these PIV vaccines do not require gene-gun delivery to animals, can be readily grown in cell cultures, and can subjected to the same types of stabilization and storage (freeze drying) conditions currently being applied to the commercially produced YFV 17D vaccine, thus providing a scalable, storable, and marketable vaccine product. Preliminary studies on stability of WN RepliVAX have shown that freeze-dried preparations show no detectable loss in titer when stored for 30 days at 4 C.

To develop the high-level growth conditions required for efficient trans-complementation (and hence yield) of pseudo-infectious flaviviruses, the present invention utilized cells expressing high levels of C (or C-prM-E) from VEEV replicons. VEEV replicons are less cytopathic than the replicons derived from other alphaviruses and readily establish persistent replications in some cell lines of vertebrate and insect origin. This system appears to be suitable for production of pseudoinfectious flaviviruses, since i) VEEV replicons are highly efficient in synthesis of heterologous proteins and, in the present invention synthesized C to the level required for flavivirus genome incapsidation. ii) VEEV replicons do not detectably interfere with flavivirus replication (Petrakova, 2005). Moreover, VEE replicons and the YF PIV genomes can replicate together in BHK-21 cells without causing CPE. iii) VEEV replicons can be packaged at high-titers into VEE virions that can be used for rapid establishment of the packaging cell lines producing flavivirus structural protein(s).

Furthermore, examination of the effect of context of C expression on yield of PIV indicated that the packaging cells expressing anchored form of C with an additional 20 a.a. of prM produced more particles than cells expressing anchored C alone, suggesting the importance of the proper sequence of processing events in virions formation. The basis for the enhanced packaging efficiency by the construct containing the first 20 amino acids of prM is unclear but this phenomenon might be explained by a requirement of specific order of cleavage at the two nearby cleavage sites (NS2B/NS3- and signal peptidase-specific) (Yamshchikov and Compans, 1994) and/or differences in distribution/stability of C protein products in these two different contexts. In addition, it was observed that co-expression of C with prM and E (VEErep/C-prM-E/Pac) caused only minor increase in PIV yield compared to VEErep/C2/Pac, which expressed anchor C with the fragment of prM.

When the codon-optimization of the VEEV replicon-encoded C genes was examined to determine if this alteration of the C gene sequence enhanced yield of PIV, it did not reveal a strong difference in YFV PIV release from the cells not expressing a codon-optimized C gene. This observation suggested that even with the non-optimized gene VEEV replicons appear to produce C at a saturating level. These results were consistent with other studies demonstrating that the cell lines that expressed VEEV replicons encoding the WNV C-E cassette produced level of E greater than those detected in WNV-infected cells. Despite the inability of the trans-expressed optimized C gene to increase yield of YF PIV, the cells harboring the VEEV replicon expressing Copt developed CPE and produced plaques when infected with YF PIV. This made a PIV infection in the Copt cells even more similar to infection developed by replication-competent virus. An additional advantage of the use of VEEV replicons encoding a YFV Copt gene in pseudoinfectious flavivirus production was the level of safety, since the changes in the codons reduced the chance of homologous recombination with the pseudoinfectious flavivirus genome. Furthermore, the Copt gene was also altered in its cyclization sequence (as described herein for the WNV C coding region in the BHK(VEErep/C*-E*-Pac) cells), to reduce the chance of the recombination producing a replicationally active C-encoding flavivirus. To date, neither the WN nor YF PIV systems described herein have produced replicationally active flaviviruses that could be detected in either cell culture, or in highly susceptible animals. Additionally, in vivo experiments demonstrated that both YF and WN PIVs were safe and could not cause any disease even after i.c. inoculation of 3- to 4-day-old mice with the highest dose of the PIVs. Nevertheless, WN PIVs were capable of inducing high levels of neutralizing antibodies and protected mice against infection with replication competent WNV.

Furthermore, Hepatitis C ranks with AIDS as a major infectious cause of morbidity and mortality for which no vaccine is currently available. In Japan and Korea, HCV now exceeds hepatitis B in contributing to the development of hepatocellular carcinoma, one of the most common types of cancer and a common mode of death due to liver disease. This pattern is likely to become increasingly common in other Asian countries and elsewhere in the developing world, due to the increasing prevalence of HCV coupled with effective immunization against hepatitis B. In some communities in Egypt and elsewhere, the prevalence of hepatitis C infection is spectacularly high, likely due at least in part to traditional health care practices and/or the introduction of dangerous Western technologies in the past (e.g., needle-borne transmission of the virus during public health campaigns directed against schistosomiasis).

In many developing countries, where rates of liver cancer and cirrhosis are high, there is little effective control of hepatitis C during blood transfusion. Hepatitis C is also a major public health problem within the United States, where there are approximately 4 million carriers of HCV, many of whom are at risk of death due to end-stage liver disease or liver cancer. Currently it is estimated that there are between 8,000 and 10,000 deaths annually due to hepatitis C in the United States. This number is likely to triple over the next 10-20 years, potentially exceeding the number of deaths due to AIDS, in the absence of new therapeutic or preventive measures.

Yet, no vaccine is available for prevention of this infection, and efforts (both national and international) to develop a vaccine are severely limited due to perceived technical difficulties, little interest in vaccine development generally on the part of big pharma, and the inertia of major funding agencies. And, as with many infectious diseases, it is the disadvantaged who are at greatest risk of serious liver disease or death due to hepatitis C.

To date attempts to create an effective vaccine against HCV infection have been unsuccessful. However, within last few years, the HCV field started to rapidly develop, and now this virus replicates in tissue culture to reasonably high titers, approaching $10^6$ inf.u/ml. There is a number of obvious similarities between the HCV genome and the genomes of other flaviviruses, like YF, JEV, TBE and others. Therefore, the strategy of designing replication-deficient flaviviruses can be applied not only to the members of the Flavivirus genus, but to *Hepacivirus* genus (that include HCV) as well. The HCV capsid protein can produced by recombinant alphavirus replicons (based on SINV, VEEV EEEV and others) in a number of cell lines, including Huh-7 and Huh-7.5 cells that are currently known to be susceptible to HCV infection. Replication-deficient HCV genomes, lacking the capsid gene can be transfected into the capsid-producing cell lines and will be packaged into infectious, capsid-containing particles. The successive rounds of infection required for the large-scale production, can be performed on these cells as well. However, in vivo, in the naïve hepatocytes (and possibly other cell types), the HCV genomes lacking the complete capsid gene or no capsid gene at all, will produce only the nonstructural viral proteins, and glycoproteins E1 and E2. These proteins will be presented to immune system i) after proteasome degradation; ii) on the cell surface and iii) in the form of virus-like particles with E1- and E2-containing envelope. Capsid deficiency will make virus incapable of spreading, and thus limited to the cells infected by the vaccinating dose.

In summary, the present invention demonstrated that capsid-deficient, pseudoinfectious flaviviruses i) could produce a spreading infection in the cell lines expressing capsid or all of the flavivirus structural genes; ii) PIVs were incapable of producing spreading infection in normal cells, (iii) PIVs produced E protein containing SVPs when they infected normal cells; (iv) PIVs displayed a high level of safety in the animals; (v) PIVs protected the mice from subsequent flavivirus infection. Taken together, the present invention demonstrated that flavivirus PIVs might be a safe, potent, and efficacious platform for development of vaccines against flavivirus infections and infections caused by viruses similar to Flavivirus.

The present invention is directed to a replication-deficient pseudoinfectious Flaviviridae, comprising: a deletion in the nucleotide sequence encoding capsid (C) protein such that the deletion does not disrupt the RNA sequence required for genome cyclization, the signal sequence for prM protein that is required for the proper maturation of prM/M or a combination thereof, where the Flaviviridae replicate only in cells expressing Cprotein or C, prM, envelope protein, mutated C protein, mutated prM, mutated envelope protein or combinations thereof of a virus of the Flaviviridae family. Generally, the Flaviviridae comprises a virus belonging to the genus flavivirus, Hepacivirus or Pestivirus or other chimeras of said viruses created by exchanging the prM-E cassettes of other viruses with the prM-E cassettes of the pseudoinfectious Flaviviridae. The examples of the viruses belonging to the genus Flavivirus are not limited to but may include yellow fever virus, West Nile virus, dengue virus, tick-borne encephalitis virus, Saint Louis encephalitis virus, Japanese encephalitis virus, Murray Valley encephalitis virus. Furthermore, the example of the virus belonging to the genus Hepacivirus includes but is not limited to Hepatitis C virus and those belonging to the genus Pestivirus include but are not limited to Bovine virus diarrhea, a swine fever virus or a hog cholera virus.

In case of flavivirus, the nucleotide sequence encoding the C protein of the Flavivirus that is deleted may encode amino acids 26 to 100 or a combination of amino acids within amino acids 26 to 100 of the C protein. Such combinations may include but are not limited to amino acids 26-93, 31-100 or 31-93. One of ordinary skill in the art can use the same guidelines to delete nucleotide sequence of C protein from other viruses belonging to the Flaviviridae family or other viruses having the same genetic makeup as these viruses. In general and applicable to all the viruses, the deleted gene is replaced by a gene encoding a marker protein or an antigen. The example of a marker protein may include but is not limited to a green fluorescent protein.

The present invention is also directed to a cell culture system expressing C protein or C, prM, envelope protein, mutated C protein, mutated prM, mutated envelope protein or combinations thereof of a virus of the Flaviviridae family, effective to enable propagation of the above-described replication-deficient Flaviviridae under suitable conditions. For this purpose, the cells expressing wild type or mutated proteins of the Flaviviridae may be generated using genetically engineered replicons derived from viral vectors.

In general, the gene encoding the protein(s) of the virus of the virus Flaviviridae family in the replicon is replaced by a codon-optimized version of the gene encoding the protein(s) of the virus such that the replacement reduces the ability of the cell line-encoded genes to recombine with the genome of the pseudoinfectious virus of the Flaviviridae family and/or increases the production of the pseudoinfectious virus of the Flaviviridae family.

For instance, such replicons may express a C protein that comprises mutations in at least 36 nucleotide positions of the gene encoding C protein of the virus of the Flaviviridae family. The replicon may express a C protein in the replicon that comprises unnatural cyclization sequences such that presence of the cyclization sequences reduces the chances of productive recombination of the replication-deficient pseudoinfective virus with natural viruses. Further, the replicon may express proteins comprising altered nucleotide sequences encoding truncated C-prM junction such that presence of such altered sequences enhances yield of the replication-deficient pseudoinfective virus in cell culture, prM/E containing SVP yield in vivo or a combination thereof.

Furthermore, the replicons expressing the proteins of Flaviviridae are introduced into the cells by transfection with in vitro synthesized replicon RNAs, by transfection with plasmid DNAs designed to synthesize functional alphaviral replicons from cellular RNA-polymerase II-specific promoters or by infection with alphaviral replicons packaged inside the alphaviral structural proteins. The viral vectors used herein may be alphaviruses. Representative examples of such alphaviruses are not limited but may include Venezuelan Equine Encephalitis Virus (VEEV), Sindbis virus, Eastern Equine Encephalitis virus (EEEV), Western Equine Encephalitis virus (WEEV) or Ross River virus.

The present invention is further directed to a method of producing a replication-deficient pseudoinfectious virus of the Flaviviridae family, comprising; generating a replication-deficient pseudoinfectious virus of the Flaviviridae family that comprises a deletion in the capsid gene such that the deletion does not disrupt the RNA sequence required for genome cyclization, the signal sequence for prM protein that is required for the proper maturation of prM/M or a combination thereof; generating a cell line that expresses C protein or C, prM, envelope protein, mutated C protein, mutated prM, mutated envelope protein or combinations thereof of a virus of the Flaviviridae family, where the cell line provides high levels of the proteins needed for propagation of the replication-deficient pseudoinfectious virus of the Flaviviridae family; and infecting the cell line with the pseudoinfectious virus of the Flaviviridae family, thereby producing the replication-deficient pseudoinfectious virus of the Flaviviridae family. All other aspects regarding the types of viruses, the position of deletions in the capsid gene, the method of generation of the cell line expressing the mutated and wild type proteins of the Flaviviridae, the type of replicons and the mutations within the replicons and the modifications in the gene encoding the mutated and wild type proteins of the Flaviviridae in the replicons are the same as discussed supra.

The present invention is also directed to a pharmaceutical composition, comprising the replication-deficient pseudoinfectious virus of the Flaviviridae family produced by the method described supra. The present invention is further directed to a method of protecting a subject from infections resulting from exposure to Flaviviridae, comprising administering to the subject an immunologically effective amount of the pharmaceutical composition described herein, where the composition elicits an immune response against the Flaviviridae in the subject, thereby protecting the subject from the infections. Such a composition may be administered via intraperitoneal, intradermal, subcutaneous, intramuscular, oral, or intranasal route. Furthermore, the subject benefiting from use of this composition may be a human, or an animal.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term, "Flaviviridae" includes the genera Flavivirus, Hepacivirus and Pestivirus. The examples of virus belonging to the genus Flavivirus include but are not limited to yellow fever virus, West Nile virus, dengue virusm a tick borne encephalitis virusm a Saint Louis encephalitis virus, a Japanese encephalitis virus or a Murray Valley encephalitis virus, Similarly, the example of virus belonging to the genus Hepacivirus includes but is not limited to Hepatitis C virus and those belonging to the genus Pestivirus include but are not limited to Bovine virus diarrhea, a swine fever virus or a hog cholera virus.

Furthermore, although the present invention discloses the construction and utility of a replication-deficient pseudoinfectious Flaviviridae belonging to the genus Flavivirus, one of ordinary skill in the art can use the same guidelines to construct chimeras comprising other viruses belonging to the Flaviviridae or to construct chimeras by exchanging the prM-E cassettes of viruses within the Flaviviridae or other similar viruses and the viruses within the Falviviridae.

The pharmaceutical compositions comprising the pseudoinfectious viruses belonging to the Flaviviridae family discussed herein may be administered concurrently or sequentially with each other or with other pharmaceutical composition(s). The effect of co-administration of such compositions is to protect an individual from the infections caused by such viruses and other vaccine-treatable disease. The composition described herein, the other pharmaceutical composition, or combination thereof can be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration and are well known to an individual having ordinary skill in this art.

The composition described herein, the other pharmaceutical composition or combination thereof may be administered independently one or more times to achieve, maintain or improve upon a therapeutic effect. It is well within the skill of an artisan to determine dosage or whether a suitable dosage of either or both of the compositions comprises a single administered dose or multiple administered doses. An appropriate dosage depends on the subject's health, the protection of the individual from flaviviral infections, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Cell Cultures

The BHK-21 cells were provided by Paul Olivo (Washington University, St. Louis, Mo.). They were maintained at 37° C. in alpha minimum essential medium (aMEM) supplemented with 10% fetal bovine serum (FBS) and vitamins. WHO-certified Vero cells, originally prepared for use in human vaccine manufacture were provided by Dr. Steve Whitehead of the NIH. Vero cells were maintained in MEM containing 6% FBS.

Example 2

Plasmid Constructs

Standard recombinant DNA techniques were used for all plasmid constructions. A schematic representation of the plasmids used are shown in FIGS. 7A-7F. Maps and sequences are shown in FIGS. 8A-8F. The parental low-copy number plasmid pACNR/FLYF-17Dx containing infectious cDNA of YFV 17D strain genome was described elsewhere (Bredenbeek et al., 2003) and provided by Dr. Charles M. Rice (Rockefeller University, New York, N.Y.). pYFPIV contained defective YFV genome (YF PIV), in which fragment encoding amino acid. 26-93 of YF capsid gene was replaced by codon-optimized GFP gene derived from pEGFP-N1 (Clontech). The WN PIV genome (pWNPIV) was derived from a Texas 2002 infectious cDNA (Rossi et al., 2005), by fusion of codon 30 of C to codon 101 of C (see FIG. 5A). The plasmids pVEErep/C1/Pac, pVEErep/C2/Pac and pVEErep/C-prM-E/Pac (FIG. 2A) encoded double subgenomic VEEV replicons, in which the first subgenomic promoter was driving transcription of the RNAs containing 5'UTR of VEEV 26S RNA followed by sequences, corresponding to nt 119-481, 119-541 and 119-2452 of YFV genome, respectively. The second subgenomic promoter was driving the expression of puromycin acetyltransferase (Pac) gene, whose product was making cells resistant to translational arrest caused by puromycin (Pur). Non-cytopathic VEEV replicons expressing the C-prM-E cassette of WNV {derived from a Sindbis virus replicon (Scholle et al., 2004)} fused to the Pac gene (designated pVEErep/C*-E*-Pac) was created from a VEE non-cytopathic replicon (Petrakova et al., 2005); E-coding sequence was fused with Pac gene through a linker consisting of the first 9 codons of NS1 and the last 25 codons of NS2B, followed by 2 codons of NS3 fused directly to FMDV 2A (see FIG. 5A). The codon-optimized sequence encoding YFV 17D capsid and first 20 amino acid of prM was designed using the codon frequency data described elsewhere (Haas et al., 1996). This gene was synthesized by PCR from the overlapping synthetic oligonucleotides. The amplified fragment was sequenced before cloning into expression cassettes VEErep/C2opt/Pac and VEErep/Copt-prM-E/Pac. The latter replicons had essentially the same design as pVEErep/C2/Pac and pVEErep/C-prM-E/Pac, but contained codon-optimized sequence presented in FIG. 4A.

Additionally, a chimeric WN-RepliVAX expressing the JEV prM-E has also been generated. This was constructed by substituting the prM and E genes of Nakayama strain of JEV in A RepliVAX encoding the WNV genome. The gene exchange was achieved by direct fusion of the last codon of the truncated WNV C protein to the first codon of the prM coding sequence of JEV (Nakayama strain). The same fusion strategy was employed at the 3' end of the cassette, with the final codon of the JEV E protein fused directly to the first codon of NS1 of WNV. These fusions were introduced into a BAC plasmid encoding the entire WN RepliVAX cDNA bounded by a T7 promoter and a ribozyme, and RNA recovered from this BAC DNA was introduced into BHK(VEErep/Pac-Ubi-C*) cells. The resulting RepliVAX (designated JE RepliVAX) formed spreading infectious foci on BHK (VEErep/Pac-Ubi-C*). As for WN RepliVAX, the foci formed on this cell line are smaller than those produced by a fully infectious WNV-JEV chimera. JE RepliVAX grows to titers approximately 10 times lower than WN RepliVAX, achieving titers of over $10^6$ U/ml in BHK(VEErep/Pac-Ubi-C*). As expected, JE RepliVAX reacts with JE-specific MAbs, and it is anticipated that like chimeric flaviviruses, JE RepliVAX will induce high levels of JEV-neutralizing antibodies, and protect against JE.

Example 3

RNA Transciptions

Plasmids were purified by centrifugation in CsCl gradients. Before the transcription reaction, the plasmids were linearized by XhoI (for pYFPIV) or MhuI (for VEE replicon and VEE helper encoding plasmids) or SwaI (for pWNPIV). RNAs were synthesized by SP6 or T7 RNA polymerase in the presence of cap analog. The yield and integrity of transcripts were analyzed by gel electrophoresis under non-denaturing conditions. Aliquots of transcription reactions were used for electroporation without additional purification.

Example 4

RNA Transfections and PIV Replication Analysis

Electroporation of BHK-21 cells was performed under previously described conditions (Liljestrom et al., 1991). For establishing packaging cell cultures, Pur was added to the media to a concentration of 10 g/ml 24 h post electroporation of the VEEV replicons. Transfection of in vitro-synthesized YF PIV genome was performed 5 days later, when replicon-containing cells resumed efficient growth. Samples were harvested at the time points indicated in the figures by replacing the media with the same media, containing Pur. In many experiments, PIV-secreting cells were split upon reaching the confluency.

VEEV replicons were packaged into VEEV infectious virions by co-electroporation of the in vitro synthesized replicon and 2 helper RNAs (Volkova et al., 2006) into BHK-21 cells. Replicon-containing viral particles were harvested 24 h post transfection and used for infecting of naïve BHK-21 cells, followed by Pur selection. In the case of WN PIV, the in vitro-synthesized PIV RNA was transfected into BHK cells containing VEErep/C*-E*-Pac replicon expressing WN C, prM and E and Pac [BHK(VEErep/C*-E*-PAC) cells]. THE scheme of the VEErep/C*-E*-PAC genome is presented in FIG. 5A. Harvested PIVs were passaged on these cells using standard methods (Rossi et al., 2005).

Example 5

Measuring the Titers of YF PIV

For measuring the titers of released YF PIV, BHK-21 cells were seeded into six-well Costar dishes at a concentration of $5 \times 10^5$ cells/well. Four hours later, cells were infected with different dilutions of packaged replicons, and after 1 h incubation at 37° C. in an 5% $CO_2$ incubator, they were overlaid with 2 ml of MEM supplemented with 10% FBS. The numbers of infected cells were estimated by counting GFP-positive cells under an inverted UV microscope. The fraction of infected cells from the seed quantity was determined via counting of fluorescence-producing cells in a defined area of microscopic field. Counts for 5 different fields were averaged and recalculated for the titer corresponding to each serial dilution.

In the later experiments, titers were also measured by plaque assay on the monolayers of BHK-21 cells, carrying VEErep/Copt-prM-E/Pac replicon, using previously described conditions (Lemm et al., 1990), except cells were incubated under agarose for plaque development for 5 days, then fixed by 2.5% formaldehyde and stained with crystal violet.

Example 6

Passaging of YF PIVs

Packaging cell lines were established either by transfection of the in vitro-synthesized VEEV replicon RNAs or by infecting cells with the same replicons packaged into VEEV structural proteins at a multiplicity of infection (MOI) of 10 inf.u/cell. After Pur selection, they were infected with YF PIV at different MOIs. Samples were harvested at the time points indicated in the figures by replacing the media.

Example 7

Analysis of YF SVP Production

BHK-21 cells were seeded at a concentration of $2 \times 10^6$ per 100-mm dish. After 4 h incubation at 37° C., cells were infected with YF PIV at an MOI of 10 inf.u/cell, and then incubated for 24 h in 10 ml of MEM supplemented with 10% FBS. Then the medium was replaced by 10 ml of serum-free medium VP-SF (Invitrogen) that was replaced every 24 h to analyze SVP release. The collected VP-SF samples were clarified by low-speed centrifugation (5,000 r.p.m, 10 min, 4° C.), and then concentrated by ultracentrifugation through 2 ml of 10% sucrose, prepared on PBS, in SW-41 rotor at 39,000 r.p.m, 4° C. for 6 h. Pellet material was dissolved in the loading buffer for SDS-polyacrylamide gel electrophoresis, lacking b-mercaptoethanol (to preserve binding to D1-4G2 MAB) and further analyzed by Western blotting. After protein transfer, the nitrocellulose membranes were processed by D1-4G2 MAB, and horseradish peroxidase (HRP)-conjugated secondary donkey anti-mouse antibodies purchased from Santa Cruz Biotechology. HRP was detected using the Western Blotting Luminol Reagent according to the manufacurer's recommendations (Santa Cruz Biotechnology). To obtain positive control sample, YFV ($2\times10^8$ PFU) was subjected to ultracentrifugation through 10% sucrose cushion as described above for SVPs.

For sucrose density gradient analysis of YFV SVPs, BHK-21 cells were electroporated with the in vitro synthesized YF PIV genome RNA. At 24 hours post-transfection, the complete MEM was replaced by VP-SF medium, which was harvested 24 hours later. At this time, more than 95% of the cells were GFP-positive and did not exhibit any signs of CPE. The harvested sample was clarified by low-speed centrifugation (5000 rpm, 10 min, 4° C.) and then concentrated by overnight centrifugation in a SW-28 rotor at 25,000 rpm, 4° C. The resulting pellet was suspended in TN buffer (10 nm Tris HCl (pH 7.5), 100 mM NaCl, 0.1% BSA) and further analysis was performed as described (Schalich et al., 1996).

Briefly, 0.5 ml samples were loaded in to the discontinuous sucrose gradient (1.5 ml of 50%, 1.5 ml of 35% and 1.5 ml of 10% sucrose prepared in PBS buffer). Centrifugation was performed in SW-55 rotor at 45,000 rpm at 4° C. for 1 h in Optima MAX Ultracentrifuge (Beckman). Pellets were dissolved in the loading buffer for SDS polyacrylamide gel electrophoresis, lacking b-mercaptoethanol (to preserve binding to D1-4G2 MAB) and further analyzed by Western blotting. After protein transfer, the nitrocellulose membranes were processed by D1-4G2 MAB and horseradish peroxidase (HRP)-conjugated secondary donkey anti-mouse antibodies purchased from Santa Cruz Biotechnology. HRP was detected using Western Blotting Luminol Reagebbr according to the manufacturer's recommendation (SantaCruz Biotechnology). Side by side gradient analyses were performed with YFV ($2\times10^8$ PFU), subjected to the same procedures as described above for YFV-PIV derived SVPs.

Example 8

Analyses of WN PIV

Titers of WN PIV were determined by infecting Vero cell monolayers with serial dilutions of virus, and then fixing 24 hours later and immunohistochemically staining with a polyclonal hyperimmune mouse ascite fluid specific for WNV, as previously described (Rossi et al., 2005). Infected cells were enumerated and used to determine the titer. To evaluate the ability of WN PIV for foci formation on Vero cells or the BHK(VEErep/C*-E*-PAC) cells, monolayers were infected with dilutions of WN PIV, overlaid with a semisolid tragacanth overlay, incubated at 37 C, and then fixed and stained with a MAB specific for WNV NS1 (provided by E. Konishi, Kobe, Japan), as described above.

Example 9

PIV Safety Studies

PIV safety was established by inoculation of different doses of virus (YFV 17D or WNV TX02 recovered from parental infectious cDNAs) or PIV into 3- to 4-day-old mice (outbred Swiss Webster, Harlan) by the intracranial (i.c.) route (20 ml volume), or 4-5 week old female mice (outbred Swiss Webster, Harlan) by the intraperitoneal (i.p.) route (100 ml volume). Mice were monitored for 14 days for signs of disease and death, animals that were moribund, and appeared to be unable to survive until the next day were humanely euthanized and scored as "dead" the following day.

Example 10

WN PIV Potency and Efficacy Studies

Selected animals inoculated with WN PIV as described above were euthanized and bled at 21 days post inoculation. Sera were harvested from the animals, pooled, and tested for their ability to reduce WNV focus formation on Vero cell monolayers using the methods described above. The remaining animals were inoculated with 1,000 inf.u (determined by focus-forming assay on Vero cells), corresponding to approximately 100 $LD_{50}$ of the NY99 strain of WNV (Xiao et al., 2001), and animals were then observed for an additional 14 days as described above.

Example 11

Both YFV C- and YFV C-prM-E-expressing Cassettes can Complement Replication of YFV PIV The general strategy for complementation of a C deletion defect in the flavivirus genome is presented FIG. 1. It is based on development of genomes lacking the C gene, and propagation of these pseudoinfectious viral genomes (PIV genomes) in cells expressing C (or all of the viral structural proteins), but not in normal cells. Replication in the latter cells, producing no viral structural proteins required for transcomplementation of the defect in PIV genome, leads to release of SVPs containing the critical protective immunogen E, but lacking the nucleocapsid containing C and the viral genetic material.

A recombinant YFV genome (YF PIV genome) was engineered to contain GFP in place of amino acid 26-93 of C, cloned in-frame with the rest of the polypeptide (FIG. 2A). The expression of GFP provided a convenient way of determining the titers of genome-containing PIVs in the experiments. The deletion in the C-coding sequence from this PIV genome was expected to destroy the ability of C to form a functional nucleocapsid, but it was not expected to affect production of functional forms of prM and E. Thus, cells expressing this genome, which produced GFP fluorescence could not release infectious virus. However, infectious progeny was expected to be produced from "packaging" cells expressing high levels of C.

For rapid development of the cell lines for efficient PIV production, the Venezuelan equine encephalitis virus (VEEV) genome-based expression system (replicons) (Petrakova et al., 2005) was used. VEEV replicons are less cytopathic than replicons derived from other alphaviruses and readily establish persistent replication in some cell lines of vertebrate and insect origin. The expression cassettes were designed as double subgenomic constructs (FIG. 2B), in which one of the subgenomic promoters was driving the expression of Pac, providing an efficient means to eliminate cells in the transfected cultures that do not contain the Pac-expressing VEEV replicon. The second subgenomic promoter was driving the transcription of subgenomic RNA encoding YFV structural proteins. To identify the most efficient packaging cassettes, VEEV replicons encoding either i)

YFV C with the signal peptide of prM, also known as anchored C (Lindenbach and Rice, 2001), (VEErep/C1/Pac), or ii) C with the signal peptide and 20 amino acid of prM (VEErep/C2/Pac), or iii) all of the YFV structural proteins (VEErep/C-prM-E/Pac). The rationale of the design was to retain the signal peptide in the C-coding cassettes that was expected to be essential for targeting C into proper cellular compartment.

The in vitro-synthesized VEEV replicon RNAs were transfected into BHK-21 cells and the $Pur^R$ stable cell lines were selected over the next 4-5 days in the Pur-containing medium. During the first 2-3 days post transfection, replication of VEEV-derived RNAs caused growth-arrest, then, as described our previously (Petrakova et al., 2005), replication became less efficient and cells resumed their growth. The resulting $Pur^R$ cultures were transfected with the in vitro-synthesized YF PIV RNAs, and at different times post transfection, titers of the released infectious particles, containing GFP-expressing genomes were determined (FIG. 2C). Surprisingly, the presence of two different replicating RNAs (YFV- and VEEV-specific) in BHK-21 cells did not result in cytopathic effect (CPE), and maintained both resistance to Pur and expression of high level of GFP, indicating replication of both the VEEV replicon and YF PIV RNA. As shown in FIG. 2C, cultures expressing both of these marker genes were capable of growing and required subpassaging (at ~1:5 ratio every 4 days) to prevent the cultures from reaching confluency. The experiments shown in FIG. 2 demonstrated that all three VEEV replicons were capable of supplying YFV C at levels sufficient for formation of infectious PIVs; no infectious particles were released from the naive BHK-21 cells transfected with the YF PIV RNA in the absence of VEEV replicons (data not shown). However, cells expressing these packaging cassettes differed in their ability to produce PIV. Constructs expressing YFV C followed by the prM signal peptide (anchored C; VEErep/C1/Pac) demonstrated the lowest level of YF PIV RNA packaging, compared to cassettes expressing longer protein sequences. The basis for the lower packaging efficiency is by the C1 construct is unclear, but this phenomenon might be explained by a requirement for a specific ordering of cleavage at the two nearby cleagage sties (NS2B/NS3 and signal peptidase) (Yamshchikov and Compans, 1994), and/or differences in distribution/stability of the C protein produced in these two different contexts. of the stability of this protein. Thus, after these experiments, VEErep/C1/Pac was eliminated from all further experiments. Both VEErep/C2/Pac and VEErep/C-prM-E/Pac replicons packaged YF PIV to the similar titers approaching above $10^7$ inf.u/ml. Moreover, the release of PIV particles continued until the experiments were terminated, with each cell releasing ~20 infectious YF PIV per 24 h time period. The same cells were probably also releasing prM/E-containing SVPs lacking the nucleocapsid and genome, but this possibility was not further investigated.

Example 12

YF PIVs with Defective Genomes can be Produced at a Large Scale

The ultimate utility of PIV as vaccine candidates is dependent upon the ability to produce these particles at the scales needed, for instance, for commercial production. Reliance on an RNA-based trans-complementation system (VEEV replicons) for vaccine manufacture requires further standardization since there is a possibility of accumulation of mutations in the heterologous genes cloned into genomes of RNA viruses. The use of low-passage cell lines, is one of the solutions for overcoming this limitation. Alternatively, accumulation of mutations in the VEErep genomes can be minimized by repeated transfection of the replicon into naïve cells, or by production of packaged VEEV replicons followed by infection of naïve cells. The use of packaged VEE replicons was considered to be one simple and efficient means for establishing the packaging cell lines.

Figures 3A, 3B:
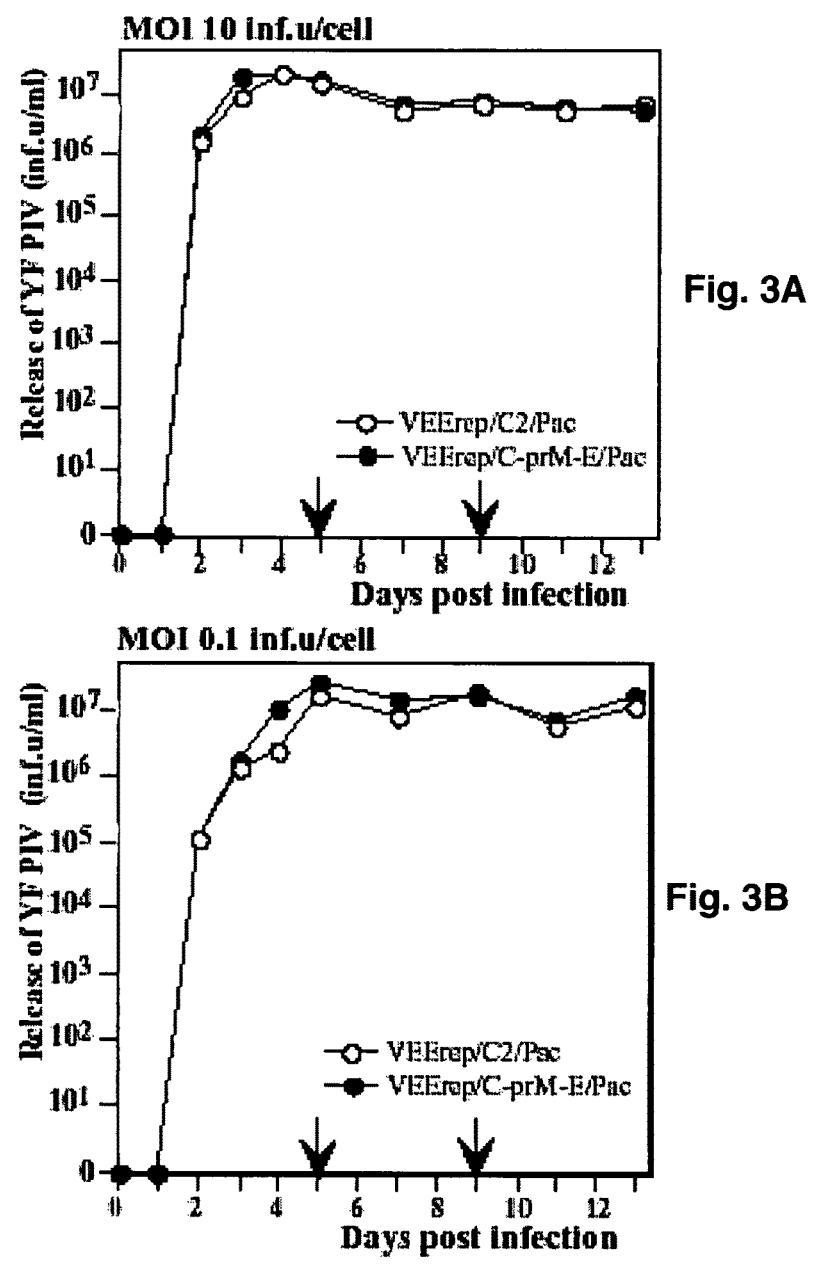

To efficiently produce PIVs, a technology that permits production of alpha virus replicon expressing cell cultures in previously packaged VEEV replicons was used. Briefly, VEEV replicons were packaged into VEEV infectious virions using previously described two-helper system (Volkova et al., 2006), into preparations that contained titers approaching $10^9$ inf.u/ml. BHK-21 cells infected with these particles and selected in the presence of Pur could be used to obtain YFV structural protein-encoding cell cultures in 3-5 days. Following establishment, the VEErep/C2/Pac- and VEErep/C-prM-E/Pac-containing cell lines were infected with previously generated samples of YF PIVs at high (10 inf.u/cell) and low (0.1 inf.u/cell) MOIs. In all cases, the defective YFVs replicated productively (see FIG. 3) and infected all of cells in the monolayers producing high titers of PIVs. Thus, rapid establishment of packaging cell lines by infecting cells with packaged VEEV replicons, followed by infection with PIVs appears to be a simple and efficient system a for large-scale production of PIVs with the deleted C sequence in the genome.

Example 13

Production of YF PIVs Using VEE Replicons Expressing Codon-Optimized Form of YFV C Gene Another possible problem in using the packaging systems to support replication of defective viruses is recombination between the defective viral genomes and the RNAs encoding the trans-complementing gene(s). Such recombination might lead to generation of the infectious viruses. In the experiments described herein, infectious YFV using a plaque assay were never detected, but it was necessary to rule out the possibility that live virus can be formed in these cells.

In addition, the proteins encoded by many arthropod-borne viruses are expected to have evolved to utilize the translational machinery in two very different hosts. Thus, their codon usage is not expected to be optimal for expression in either host. Therefore, the C-coding sequence in the expression cassettes was modified to achieve two goals: i) to enhance the yield of C production and ii) to reduce possibility of homologous recombination between YF PIV genome and C-coding subgenomic RNA of VEE replicons. YFV C was synthesized using the codon frequency found in the most efficiently translated mammalian genes (FIG. 4A). These silent mutations also disrupted the cyclization sequence required for flavivirus genome replication, thus, reducing the possibility of generating replication competent YFV in an event of recombination between YF PIV genome and YFV C-coding RNA of VEEV replicon.

The Copt gene was cloned into VEErep constructs, VEErep/Copt/Pac and VEErep/Copt-prM-E/Pac, using the same strategy as VEErep/C2/Pac and VEErep/C-prM-E/Pac, and trans-complementing $Pur^R$ cell lines were established either by RNA transfection or by infecting the cells with packaged RNAs. Transfection of these cells with the in vitro-synthesized PIV genome RNA produced PIV with efficiencies that were similar to those selected with the cells expressing VEEV replicons expressing the non-optimized YFV C gene (FIG. 4B). However, the cells expressing the codon-optimized C proved to be a useful reagent in that they were capable of developing CPE and forming clearly visible plaques when infected with YF PIV and overlaid with agarose containing media with low concentration of FBS (FIG. 4C). Thus, although codon optimization of YFV C gene did not alter PIV production from these cells, the cells expressing the codon-optimized YFV C represent a very useful system for evaluation of YF PIVs, particularly those expressing no fluorescent markers. In additional tests, a very good correlation was observed between the titers of the same samples determined in plaque-forming assays and GFP-foci assays.

Plaques formed by YF PIV were smaller than those of YFV indicating that structural proteins were most likely produced in cis functio more efficiently in viral particle formation. The reason for attaining the ability to form plaques is not completely understood yet. However, it is speculated that YFV C has some level of cytotoxicity because of cell lines containing VEEV replicons expressing the codon-optimized version of this protein demonstrated lower growth rates (data not shown) than corresponding counterparts with replicon encoding natural C gene. Thus, YF PIV genome replication might lead to additional changes in the intracellular environment that were sufficient to cause CPE.

Example 14

PIVs can be Generated for Other Flaviviruses

Figures 5A, 5B, 6A, 6B, 6C:
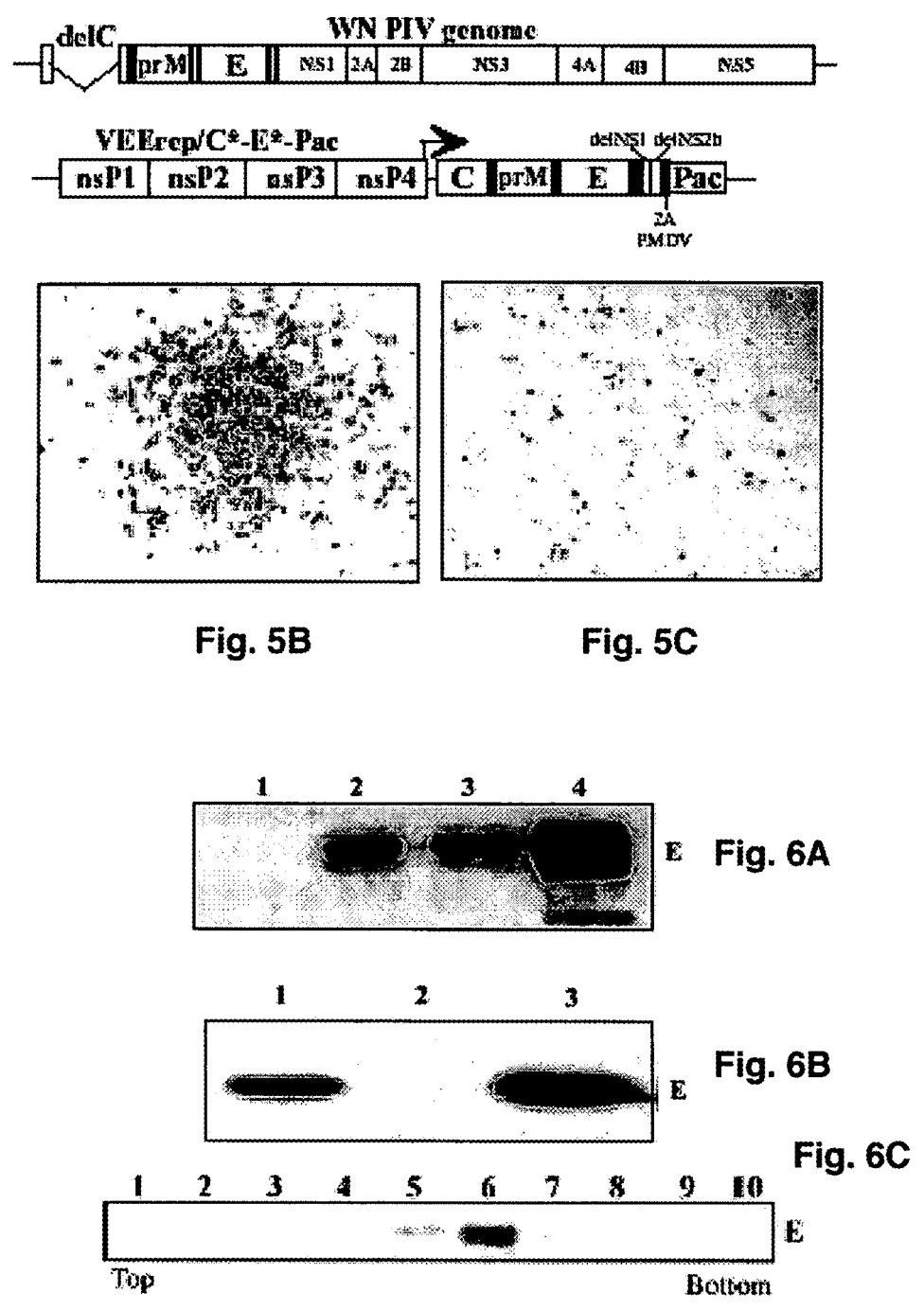

To prove that PIVs can be easily generated for other flaviviruses, the strategy described above was applied to WNV. To this end, a WN PIV genome with a 35-amino acid-long C protein was created (FIG. 5A). To package this WN PIV genome, a packaging cell line generated by transfection of BHK cells with a non-cytopathic VEEV replicon expressing WNV C/prM/E and Pac [BHK(VEErep/C*-E*-Pac)] was used. To minimize the chance that recombination between WN PIV genomes replicating in this cell line and the VEErep RNA-encoded C protein could lead to generation of the infectious WNV, the WNV C-coding gene in the VEEV replicon was modified to contain clustered silent mutations in the WNV cyclization domain.

Media harvested from BHK (VEErep/C*-E*-Pac) cells transfected with the synthetic WN PIV genome were capable of producing antigen-positive foci in the packaging cells (FIG. 5B) indicating that infectious WN PIV had been produced. However, only antigen-positive cells were detected upon infection of Vero cell monolayers with same samples (FIG. 5C). Titers of up to $1 \times 10^8$ inf.u/ml of WN PIV were produced on the packaging cells, and as expected, WN PIV could be repeatedly passed on this cell line. Thus, using an established cell line, high titer stocks of WN PIV could be readily obtained using the same complementation system described above for YFV. Interestingly, in the case of the WNV packaging cell line and WN PIV, it was observed that the virus yields plateaued late in infection, simultaneously with the appearance of CPE (results not shown), whereas the cells co-replicating YF PIV genome and VEEV replicons continued to produce PIV for many days (FIG. 2).

Example 15

Cells Infected with YF or WN PIVs Produce SVPs

To demonstrate that cells infected with PIVs produced SVPs, BHK-21 cells were either transfected with the in vitro-synthesized YF PIV RNA or infected with YF PIVs produced in C-expressing cells. The particles released from the BHK-21 cells were purified by ultracentrifugation, and analyzed by western blotting using a mouse monoclonal antibody (MAB) specific for E, D1-4G2 (Gentry et al., 1982). Both RNA-transfected and PIV-infected cells produced E protein that could be pelleted from the media (FIG. 6A), indicating that it was present in a particulate form. Since these cells did not exhibit any CPE, and the samples were clarified at low-speed centrifugation prior to ultracentrifugation, it is unlikely that the E protein detected in the pelleted fraction represented cellular debris. Similarly, western blot analyses demonstrated that Vero cells infected with the WN PIV produced (before development of any signs of CPE) extracellular forms of E that were indistinguishable in size from those produced by WNV-infected Vero cells (FIG. 6B).

To further evaluate the physical nature of the E protein released by PIV-infected cells, media collected from cells containing replicating PIV genomes only were subjected to sucrose density gradient analysis in agreement with published data (Schalich et al., 1996). SVPs were found in the fraction having 2% sucrose (FIG. 6C). In the same experiment, YFV virions demonstrated high density and were detected in the fraction with 42% sucrose. E protein-containing particles that migrate at the expected size of WNV SVPs have also been detected in cultures infected with WNV PIVs. The presence of E in the media of PIV-infected cells was consistent with the production of SVPs by cells expressing only prM/E or TBEV RNA vaccines lacking a functional C gene.

Example 16

PIV Safety, Potency, and Efficacy in Animals

Safety of WN and YF PIVs was established by i.c. inoculation of litters of 3 to 4-day-old mice. These studies showed that mice inoculated with WT YFV or WNV were quickly killed, and these viruses displayed a 50-percent lethal dose ($LD_{50}$) of approximately 1 PFU in these animals (Table 1). However, WN and YF PIVs inoculated into suckling mice at a dose of $2 \times 10^6$ inf.u failed to kill any mice (Table 1). Safety was further documented by i.p. inoculation of adult mice with wild type (wt) viruses and WN PIVs. These studies showed that the WN PIVs were completely safe in adult mice (Table 2). Furthermore, wt WNV killed a significant portion of adult mice, with an $LD_{50}$ of less than 1 PFU, and doses of up to $3 \times 10^6$ inf.u of WN PIV failed to cause any death (Table 2). Most interestingly, however, is the finding that the WN PIVs were very potent immunogens (NEUT titers were detected with inoculation of as few as 30,000 inf.u), and 100% of the animals vaccinated with $3 \times 10^4$, $3 \times 10^5$, or $3 \times 10^6$ inf.u were protected from a 100$LD_{50}$ challenge of the NY99 strain of WNV (Table 2).

TABLE 1

Safety of PIVs in suckling mice.

| Inoculum[a] | Dose (inf · u)[b] | % Survival[c] | Average survival time[d] |
|---|---|---|---|
| WN PIV | 2,000,000 | 100 (9/9) | NA[e] |
| WNV TX02 | 0.2 | 56 (5/9) | 8.5 (+/−2.9) |
| WNV TX02 | 2 | 0 (0/9) | 5.4 (+/−0.5) |
| WNV TX02 | 20 | 0 (0/8) | 6 (+/−0) |
| WNV TX02 | 200 | 0 (0/10) | 4.9 (+/−0.3) |
| YF PIV | 2,000,000 | 100 (10/10) | NA[e] |
| YFV 17D | 0.2 | 89 (8/9) | 8 (+/−0) |
| YFV 17D | 2 | 56 (5/9) | 7 (+/−0) |

TABLE 1-continued

Safety of PIVs in suckling mice.

| Inoculum[a] | Dose (inf · u)[b] | % Survival[c] | Average survival time[d] |
|---|---|---|---|
| YFV 17D | 20 | 11 (1/9) | 6.9 (+/−2.4) |
| YFV 17D | 200 | 0 (0/12) | 6 (+/−0) |

[a]Inoculated preparation, diluted in culture media with 10% FBS
[b]Delivered by i.c. route in a volume of 20 ml/animal
[c]Survival at 14 days postinoculation (live/dead)
[d]Average survival time from animals that died from infection (standard deviation)
[e]Not applicable

TABLE 2

Safety, potency and efficacy of PIV in adult mice

| Inoculum[a] | Dose (inf · u)[b] | % Survival[c] | Average survival time[d] | NEUT titer[e] | % Protection[f] |
|---|---|---|---|---|---|
| none (diluent) | 0 | 100 (8/8) | NA[g] | <1:40[h] | 14 (1/7) |
| WN PIV | 30,000 | 100 (10/10) | NA[g] | 1:40 | 100 (8/8) |
| WN PIV | 300,000 | 100 (10/10) | NA[g] | 1:160 | 100 (8/8) |
| WN PIV | 3,000,000 | 100 (10/10) | NA[g] | 1:160 | 100 (8/8) |
| WNV TX02 | 1 | 40 (4/10) | 8.5 (+/−1.4) | | |
| WNV TX02 | 10 | 30 (3/10) | 8 (+/−1.2) | | |
| WNV TX02 | 100 | 10 (1/10) | 7.8 (+/−1.4) | | |

[a]Inoculated preparation, diluted in culture media with 10% FBS.
[b]Delivered by i.p. route in a volume of 100 ml/animal.
[c]Survival at 14 days postinoculation (live/dead).
[d]Average survival time from animals that died from infection (standard deviation).
[e]NEUT titer of pooled sera collected from 2 animals at 21 days postinoculation (titer shown is the highest dilution giving 80% reduction of WNV foci formation).
[f]Protection from challenge with 100LD$_{50}$ of the NY99 strain of WNV demonstrated by survival at 14 days post-challenge; single survivor from the diluent-inoculated group showed signs of disease (hunched back; ruffled fur, and malaise) from days 8-14. None of the PIV inoculated animals displayed any signs of disease in the 14-day postchallenge observation period.
[g]Not applicable.
[h]NEUT titers in sera from unimmunized mice tested side-by-side with sera from the WN PIV-inoculated mice.

Example 17

Further Modifications to Increase the Yield and Safety of PIVs/RepliVAX

Figure 9:
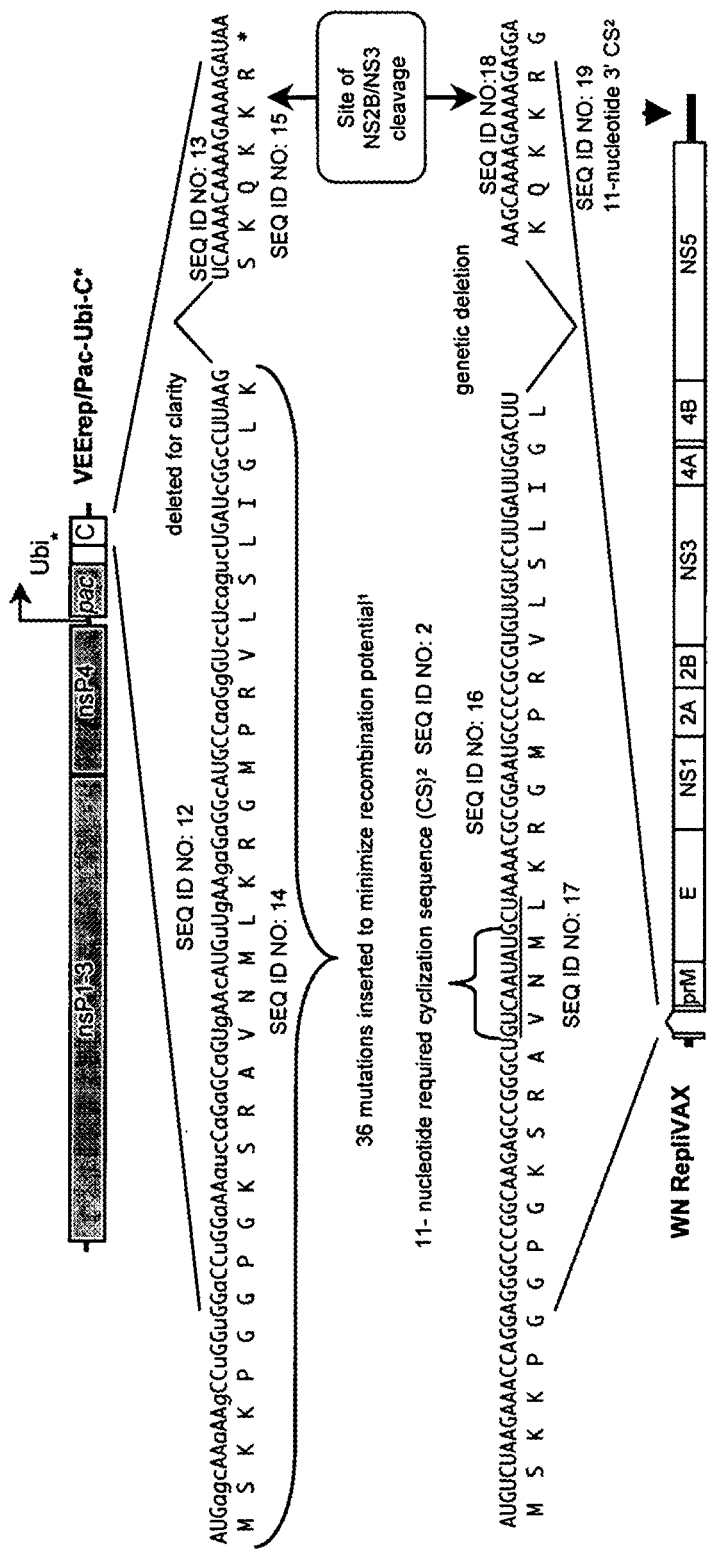
FIG. 9 shows a schematic representation of overlapping regions of RepliVAX and the VEE replicon used to provide C in trans. [1]Thirty-six mutations were inserted into the VEErep/pac-Ubi-C* to minimize homologous recombination with the fragment of C encoded by the RepliVAX genome. [2]Position of 5' and 3' CS sequences in the RepliVAX genome.

The present invention demonstrates that repeated passaging of RepliVAX did not result in recombination, but variants with enhanced growth were selected: The WNV RepliVAX has been repeatedly passaged on a cell line that encodes the WNV C protein. This C protein was produced by fusing a copy of the WNV C gene to a Pac gene driven by the subgenomic promoter of a non-cytopathic VEErep (Petrakova et al., 2005). In the resulting construct (VEErep/Pac-Ubi-C*), the ubiquitin (Ubi) gene was inserted in front of the C gene, and C was followed by a stop codon. In this context, a Pac-Ubi fusion protein would be produced along with a mature C protein (lacking the hydrophobic anchor; see FIG. 9). The C gene in this VEErep (denoted as "C*") was further modified by insertion of 36 mutations that ablate the CS signal, converting this 11-base region from GUCAAUAUGCU (SEQ ID NO: 2) to GUgAAcAUGuU (SEQ ID NO: 3) while maintaining C coding capacity. This large number of mutations dramatically reduces the likelihood of homologous recombination, and furthermore, if recombination did occur between the genomes, the production of a replicationally active genome could not occur, since the resulting RNA would have unmatched CSs, preventing replication (FIG. 9).

To test for the unlikely possibility of productive recombination, a clonal cell line was derived from BHK cells expressing VEErep/Pac-Ubi-C* {BHK(VEErep/Pac-Ubi-C*)}, and this cell line was used to passage the WN RepliVAX 10 times (in each case with infection at an MOI of 0.01), and the resulting RepliVAX was characterized in detail. To determine if this passage 10-(p10) population contained any live virus, Vero cell monolayers were infected at multiplicities of 0.1, 1, and 10 with the p10 WN RepliVAX, and washed extensively to remove extracellular RepliVAX. These monolayers were re-washed 24 hours later, and then harvested 2 days later. Passage of supernatant fluids from these cultures onto fresh Vero cell cultures failed to reveal any immunopositive cells when stained with a highly sensitive polyclonal antibody for WNV, indicating that RepliVAX had not productively recombined with the C protein encoded by the packaging cell line.

Interestingly, when the p10 WN RepliVAX was compared to p0 RepliVAX on the BHK(VEErep/Pac-Ubi-C*) cell line, the p10 RepliVAX produced polymorphic foci of infection, many of which were much larger than those produced by the p0 RepliVAX (FIG. 10). Furthermore, p10 RepliVAX replicates 10 times higher than p0 RepliVAX at early time points, with an endpoint titer twice as high.

Analyses of the PCR products obtained from cDNA produced from Vero cells infected with this p10 RepliVAX demonstrated that there were no products that contained a full-length C coding region. However, sequence analyses of the C-prM junction of the product spanning these regions revealed that two mutations had arisen during passaging. As expected from the heterogeneous nature of the foci produced by the p10 RepliVAX on the packaging cells (FIG. 10), both mutations were present as mixtures with the original RepliVAX sequence. One of the mutations, which appeared to be present over half of the nucleic acid population in these sequence reactions (sequenced in both directions), consisted of a AGC>uGC (S>C) mutation at the P4 position preceding the signal peptidase cleavage site (S(c)VGA|VTLS (SEQ ID NO: 4) in the RepliVAX genome. The second mutation, which was present in only about 30% of the amplified sequences (again in reactions completed in both directions) consisted of an AAG>AuG (K>M) at position P3 following the NS2B/NS3 cleavage site (QKKR|GGK(m)T) (SEQ ID NO: 5). Although these mutations are in the position of the deleted SL5, they do not alter predicted RNA structures. The rapid selection (only 10 growth cycles) of a better-growing RepliVAX is very exciting since it indicates that selection of better-growing variants is a powerful method to improve RepliVAX. The positions of these mutations was not unexpected since it is known that altering efficiency of NS2B/NS3 versus signal peptidase cleavage can influence flavivirus particle yield and infectivity (Keelapang et al., 2004; Lee et al., 2000; Lobigs and Lee, 2004; Yamschikov et al., 1997). Studies are continuing on selection of even better growing variants, and these two mutations are being targeted for insertion into second-generation RepliVAX constructs, to confirm their ability to work separately (or together) to improve RepliVAX yield and antigen production. Nevertheless, the data presented herein indicate that under these passage conditions: 1) no recombination occurred, 2) positive selection could be used to produce improved RepliVAXs.

Blind passage of JE RepliVAX similarly yielded better-growing variants with mutations in the same regions of the genome. The ability to blind passage RepliVAX products to produce better growing variants is a key feature of this invention, and a clear advantage over traditional LAV, where production of better-growing variants is always complicated by the concern that these better-growing variants may have lost their attenuation in man.

Furthermore, the mutated, improved C-expression cassette (VEErep/Pac-Ubi-C*), which has been shown to be stable, and demonstrated freedom from recombination when used in a BHK cell line (not approved for human vaccine generation), has also been shown to be stable and useful for PIV propagation when introduced into Vero cells (an accepted cell line for the production of human vaccines). Specifically, RNAs corresponding to the VEE replicon have been introduced Vero cells from a certified seed using the same methods applied to BHK cells. Following introduction of the RNA into these Vero cells, the cells were maintained in serum free media (an important issue for vaccine generation) containing puromycin, and these cells were shown to be useful for PIV propagation. Under these propagation conditions, these cells have been shown to produce slightly lower titers of PIV than similarly derived BHK cells, but the VEErep/Pac-Ubi-C*-Vero cells hold up better under these culture conditions, permitting multiple harvests. FIG. 11 shows the production of PIV from these cells can be obtained for multiple harvests under serum-free conditions.

In summary, propagation of PIVs in cell lines that express C (especially C cassettes that contain the signal sequence of prM, or this region plus portions of the prM and E genes) can theoretically recombine with the PIV genome, producing a live virus that could cause disease, increasing the risk of the method of vaccine generation. To overcome this problem, the present invention demonstrated that cell lines for the propagation of WN PIV can be produced using a C protein that ends precisely at the NS2B/NS3 cleavage site, minimizing the chance of recombination at this region of the PIV genome, providing an advantage over other propagation methods in which cell lines encode RNAs that encode the portion of the anchor of C (that is also know as the signal peptide of prM) that are shared by the PIV.

To further enhance the safety of this C-expression cassette, the present invention demonstrated that the portion of the cassette that is used to make the VEErep-encoded C that complements the PIV genome (namely the first 30 codons encoding the amino acid sequence that are required to produce a replicating PIV genome due to underlying RNA elements required for viral replication) could be specifically mutated to produce a cassette that differs from the PIV genome at 36 nucleotide positions (introduced without altering the protein product) resulting in a C gene that has a dramatically reduced probability of recombination with the PIV genome (FIG. 9). Furthermore, this mutated C gene was created to have three mutations in the cyclization signal (CS) that must be complementary to a CS in the 3'UTR of the PIV genome to allow viral replication, providing a further safety feature to prevent recombination (FIG. 9). Finally, this C gene was inserted into the VEEreplicon following the selectable marker gene (pac), by using a ubiquitin gene to the intact C product from the resulting polyprotein (alternative self-cleaving sequences such as the auto-proteinase 2A of FMDV, or other related sequences could easily be substituted for ubiquitin). Creation of this single-polyprotein cassette provides the advantage of producing a genetically more stable VEEreplicon, reducing the chance of recombination within the propagating cell lines, eliminating the C-expression cassette, and reducing PIV yield. The resulting construct (VEErep/Pac-Ubi-C*, FIG. 9) was introduced into BHK cells, and the cells were used to produce a clonal cell line expressing the VEE replicon using established methods (Fayzulin et al., Virology 2006).

One clonal cell line was examined after 18 passages from single-cell cloning, and found to have no evidence of any genetic deletion of the C cassettes (by RT-PCR), nor was it found to have any detectable mutations within the C-expression cassette. Most importantly, this cell line displayed similar ability to propagate the WNV PIV at a passage level as high as 41. Finally, following 10 passages of PIV on this cell line, no evidence of recombination producing PIV-recombinants capable of productive replication on cells that do not express the C cassette (namely WT Vero cells), and no evidence of introduction of C-encoding sequences into the PIV genome by RT PCR was observed.

Figure 12A:
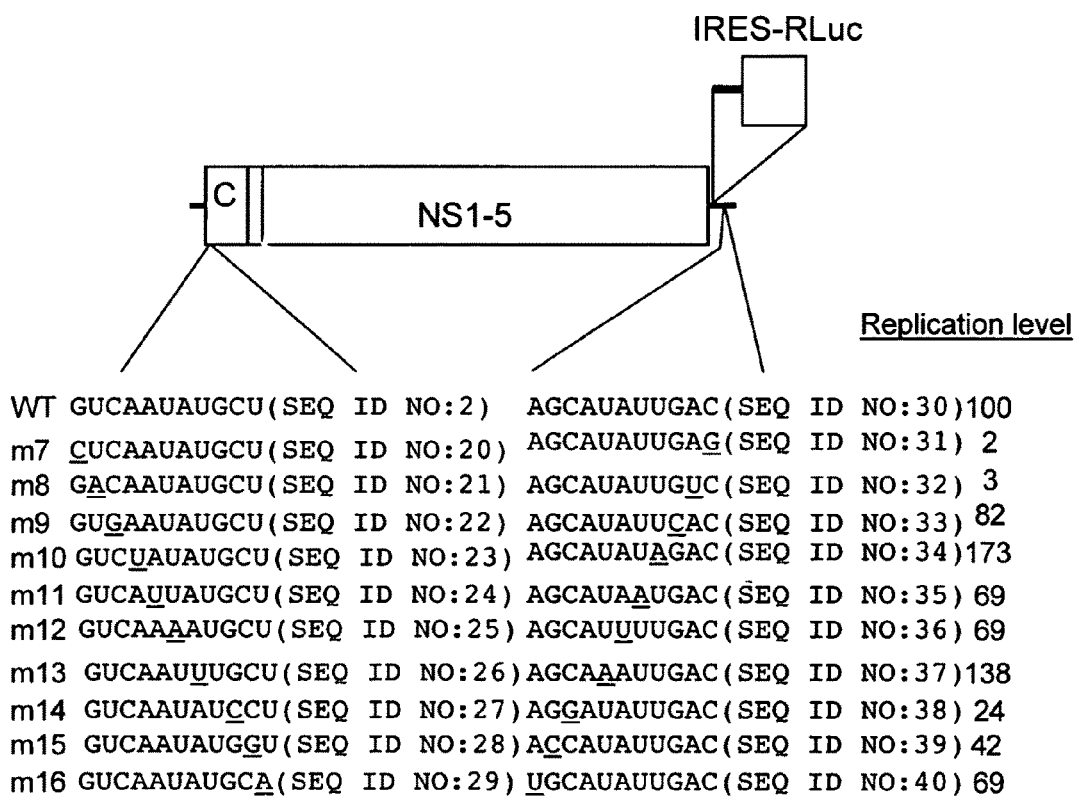
FIGS. 12A-12B show cyclization mutants.
Figure 12B:
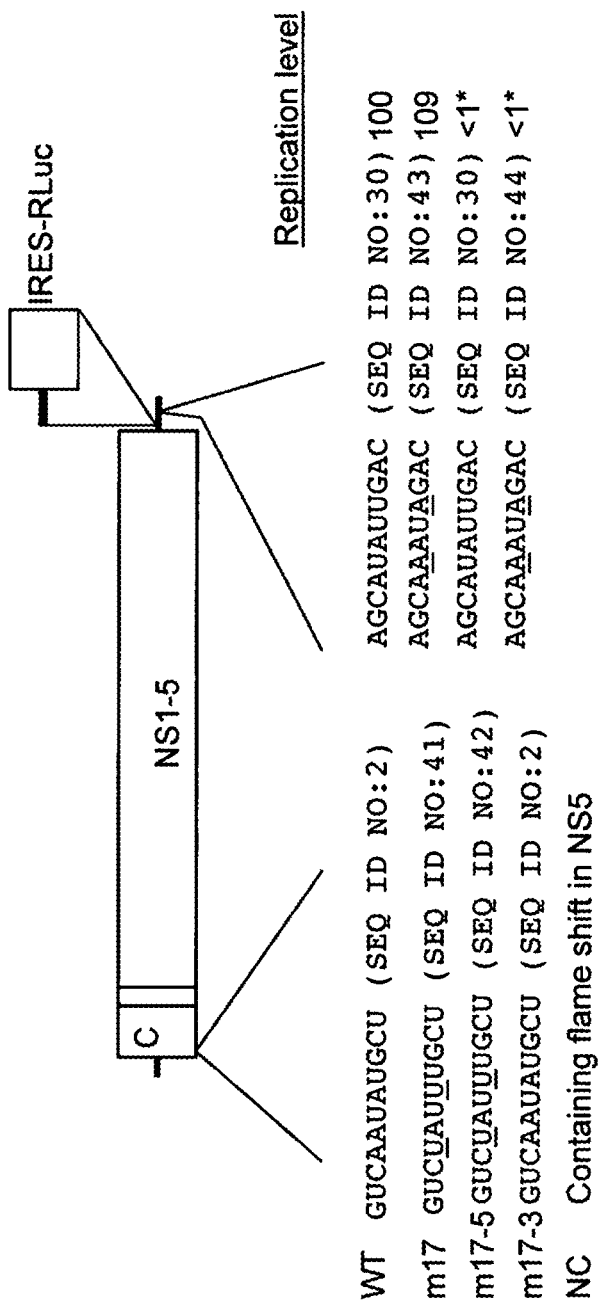

Furthermore, to address concerns that PIV might recombine with flaviviruses in vaccines at the time of their vaccination, producing novel, virulent flaviviruses, the present invention demonstrated that WNV genomes with "unnatural" cyclization signals (CS) present in all known naturally circulating flaviviruses, can be generated that replicate to high levels. Evidence has been produced in several laboratories that the two CS found at the 5' and 3' ends of the genomes of all flaviviruses must be 100% complementary to provide productive viral replication (Khromykh et al. J. Virol., 2001; Lo et al., J. Virol., 2003; Alvarez et al., Virol., 2003). These studies also demonstrated that unnatural CSs could produce replicating genomes, as long as the CS were 100% complementary. However these investigators reported that all genomes with unnatural CS sequences had replication defects. By systematic analysis of CS in WNV genomes, specifically the testing the ability of carefully selected single base swaps to produce high-level replication, single-base changes, and subsequent double-base changes that permit high-levels of genome replication (FIG. 12A) were identified. FIG. 12B demonstrates that high-level replication of WNV genome with two-base substitutions is possible, and that genomes intentionally created with mis-matched CS sequences (namely WT and the 2-base mutant) are not replicationally active. This mutation, and others like it, can therefore be utilized to produce PIV with a superior safety profile, since any recombinant virus resulting from a single-point genetic recombination between the CS-modified PIV vaccine and a virus circulating in areas where people are undergoing vaccination would not be replicationally active, and hence could not cause disease.

Example 18

BHK Cells Expressing WNV C Gene Maintain their Phenotype for Multiple Passages

Studies with a WNV C-expressing clonal cell line derived from BHK cells transfected with VEErep/Pac-Ubi-C* has demonstrated its long-term stability and utility in generating RepliVAX for several reasons. Firstly, these cells were useful for repeated passaging of RepliVAX. Secondly, side-by side focus-formation assays on cells at two different passage levels (passages 8 & 24 after single-cell cloning) showed indistinguishable WN RepliVAX titers and foci sizes. Finally, direct analysis of the sequence of the C-encoding cassette in these cells at the passage-24 level revealed no changes relative to the original VEErep sequence. Taken together these data indicate that cells harboring C-expressing VEEreps should be stable enough for use in the currently accepted master cell seed lot format used to produce human vaccines. Furthermore, the fact that VEEreps have already been used in human trials, make it likely that the application of the VEErep-cell technology to Vero cells will not encounter any unexpected hurdles during regulatory approval.

Example 19

Lymphoid Tissue Targeting of WNV VLPs

As indicated supra, WNV VLPs are similar to RepliVAX, except in place of the flavivirus prM/E proteins, they can encode a reporter gene, or they can simply contain a flavivirus replicon without a reporter. VLPs can be readily produced in packaging cells expressing all three WNV structural proteins, and have been produced at high titer (Fayzulin et al., 2006). When $10^7$ U of VLP were inoculated into mice, these animals produced 1,000 to 5,000 U/ml of type I interferon (IFN) in their serum 24 hr post-inoculation. IFN responses were produced by both ip and subcutaneous footpad injection (fp). Furthermore, popliteal lymph nodes dissected 24 hrs after fp inoculation with b-galactosidase-expressing VLPs contained large numbers of b-galactosidase-positive cells, indicating that VLPs, which enter cells in a manner indistinguishable from RepliVAX, are targeting important lymph organs. This result is consistent with the high levels of IFN elicited by VLP-injection and suggests that similar targeting is responsible for the high potency and efficacy of RepliVAX.

The following references were cited herein:

Aberle, J. H. et al., 1999, *J Immunol* 163, 6756-61.
Aberle, J. H. et al., 2005, *J Virol* 79, 15107-13.
Bredenbeek, P. J. et al., 2003 *J Gen Virol* 84, 1261-8.
Chambers, T. J. et al., 1999 *J Virol* 73, 3095-101.
Clyde and HArris, 2006, *J Virol* 80: 2170-2182.
Colombage, G. et al. 19.98, *Virology* 250, 151-63.
Davis, B. S. et al., 2001, *Journal of Virology* 75, 4040-4047.
Fayzulin et al., 2006, *Virology* 351: 196-209.
Filomatori et al., 2006, *Genes Dev* 20: 2238-2249.
Fonseca, B. A., et al., 1994, *Vaccine* 12, 279-85.
Gentry, M. K et al., 1982, *Am J Trop Med Hyg* 31, 548-55.
Gerasimon, G., and Lowry, K., 2005, *South Med J*98, 653-6.
Haas, J., et al., 1996 *Curr Biol* 6, 315-24.
Hall, R. A., et al., 2003, *Proc Natl Acad Sci USA* 100, 10460-10464.
Huang, C. Y., et al., 2003, *J Virol* 77, 11436-47.
Kanesa, T. N., et al., 2030 *Vaccine* 19, 483-491.
Keelapang et al., 2004, *J Virol* 78: 2367-2381.
Kochel, T et al., 1997, *Vaccine* 15, 547-52.
Kochel, T. J. et al., 2000. *Vaccine* 18, 3166-3173.
Kofler, R. M., et al., 2004, *Proc Natl Acad Sci USA* 101, 1951-6.
Konishi, E., and Fujii, A., 2002, *Vaccine* 20, 1058-67.
Konishi, E et al., 2001 *Journal of Virology* 75, 2204-2212.
Konishi, E et al., 1992a *Virology* 190, 454-8.
Konishi, E et al., 1992b, *Virology* 188, 714-20.
Konishi, E et al., 2000a, *Vaccine. Jan.* 18, 1133-1139.
Konishi, E. et al., 2000b, *Virology* 268, 49-55.
Lee et al., 2000, *J Virol;* 74: 24-32.
Lemm, J. A et al., 1990, *J Virol* 64, 3001-11.
Liljestrom, P et al., 1991 *J Virol* 65, 4107-13.
Lobigs and Lee, 2004, *J Virol* 78: 178-186.
Lindenbach et al., 2001, 2001, Flaviviridae: the viruses and their replication Knipe et al., (Eds. $4^{th}$ Ed. Fields Virology, Vol. 1, Lippincott Williams and Wilkins, Philadelphia., pp. 991-1041(2 vols)).
Lorenz, I. C. et al., 2002 *J Virol* 76, 5480-91.
Mason, P. W. et al., 1991, *Virology* 180, 294-305.
Minke, J. M. et al., 2004, *Arch Virol Suppl,* 221-30.
Mishin, V. P. et al., 2001 *Virus Research* 81, 113-123.
Monath, T. P. 1991, *Am J Trop Med Hyg* 45, 1-43.
Monath, T. P. et al., 2002 *Vaccine* 20, 1004-18.
Petrakova, O et al., 2005 *J Virol* 79, 7597-608.
Phillpotts, R. J. et al., 1996 *Arch Virol* 141, 743-9.
Pincus, S., et al., 1992 *Virology* 187, 290-7.
Pletnev et al., 2002, *Proc. National Academy of Sciences USA* 99, 3036-3041.
Pugachev, K. V. et al., 2004 *J Virol* 78, 1032-8.
Pugachev, K. V., et al., 1995 *Virology* 212, 587-94.
Qiao, M. e al., 2004 *J Infect Dis* 190, 2104-8.
Rossi, S. L. et al, 2005, *Virology* 331, 457-70.
Schalich et al., 1996, *Virology,* 70: 4549-4557.
Schmaljohn, C. et al., 1997, *J Virol* 71, 9563-9.
Scholle, F. et al., 2004, *J Virol* 78, 11605-14.
Volkova, E. et al., 2006, *Virology* 344, 315-27.
Xiao, S. Y. et al. 2001, *Emerging Infectious Diseases Jul. Aug.* 7, 714-721.
Yamshchikov, V. F., and Compans, R. W., 1994), *J Virol* 68, 5765-71.
Yamshchikov et al., 1997, *J Virol,* 71: 4364-4371.
Zuker, 2003, *Nucleic Acid Res* 31: 3406-3415.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A replication-deficient pseudoinfectious virus comprising:
a mutant flavivirus genome having a deletion of nucleotide sequence encoding amino acids 26 to 93, 31 to 93, 31 to 100, or 26 to 100 of the flavivirus capsid protein, wherein the deletion mutant genome cannot produce capsid-containing viral particles in a cell that does not express a capsid protein, and wherein the deletion does not disrupt the maturation of prM protein or the RNA sequence required for genome cyclization.

2. The replication-deficient pseudoinfectious virus of claim 1, wherein said virus is a chimeric virus comprising a heterologous prM-E cassette.

3. The replication-deficient pseudoinfectious virus of claim 2, wherein the heterologous prM-E cassette is from a yellow fever virus, a West Nile virus, a dengue virus, a tick-borne encephalitis virus, a Saint Louis encephalitis virus, a Japanese encephalitis virus, or a Murray Valley encephalitis virus.

4. The replication-deficient pseudoinfectious virus of claim 1, wherein the mutant genome further encodes a heterologous marker protein or an antigen.

5. The replication-deficient pseudoinfectious virus of claim 4, wherein the marker protein is a green fluorescent protein.

6. The replication-deficient pseudoinfectious virus of claim 1, wherein the deletion mutant genome further comprises one or both of altered C-prM junction sequences SEQ ID NO:4 and SEQ ID NO:5.

7. An isolated host cell comprising a flavivirus deletion mutant genome having a deletion of nucleotide sequence encoding amino acids 26 to 93, 31 to 93, 31 to 100, or 26 to 100 of the flavivirus capsid protein, wherein the deletion mutant genome cannot produce capsid-containing viral particles in a cell that does not express a capsid protein, and wherein the deletion does not disrupt the maturation of prM protein or the RNA sequence required for genome cyclization.

8. A cell culture system comprising:
(a) a flavivirus deletion mutant genome comprising a deletion of the nucleotide sequence encoding amino acids 26 to 93, 31 to 93, 31 to 100, or 26 to 100 of the capsid protein, wherein the deletion mutant genome cannot produce capsid-containing viral particles in a cell that does not express a capsid protein, and wherein the deletion does not disrupt the maturation of prM protein or the RNA sequence required for genome cyclization; and
(b) a host cell expressing a flavivirus capsid protein.

9. The cell culture system of claim 8, wherein the cell comprises a replicon encoding a codon-optimized flavivirus capsid protein.

10. The cell culture system of claim 9, wherein the replicon is an alphavirus replicon.

11. The cell culture system of claim 8, wherein the flavivirus capsid protein expressed by the host cell is a Venezuelan Equine Encephalitis Virus capsid protein.

12. A method of producing a replication-deficient pseudoinfectious virus comprising:
introducing into a cell expressing a flavivirus capsid protein a flavivirus deletion mutant genome comprising a deletion of the nucleotide sequence encoding amino acids 26 to 93, 31 to 93, 31 to 100, or 26 to 100 of the capsid protein, wherein the deletion mutant genome cannot produce capsid-containing viral particles in a cell that does not express a capsid protein, and wherein the deletion does not disrupt the maturation of prM protein or the RNA sequence required for genome cyclization; and
culturing the cell comprising the flavivirus deletion mutant genome under conditions that result in the production of replication-deficient pseudoinfectious virus.

13. The method of claim 12, wherein the deletion mutant genome comprises a heterologous prM-E cassette.

14. The method of claim 13, wherein the heterologous prM-E cassette is from a yellow fever virus, a West Nile virus, a dengue virus, a tick-borne encephalitis virus, a Saint Louis encephalitis virus, a Japanese encephalitis virus, or a Murray Valley encephalitis virus.

15. The method of claim 12, wherein the cell comprises a replicon expressing a flavivirus capsid protein.

16. The method of claim 15, wherein the replicon is an alphavirus replicon.

17. The method of claim 16, wherein the alphavirus is Venezuelan Equine Encephalitis Virus, Sindbis virus, Eastern Equine Encephalitis virus, Western Equine Encephalitis virus, or Ross River virus.

18. The method of claim 15, wherein the replicon comprises a codon-optimized nucleic acid sequence encoding the flavivirus capsid protein.

19. The method of claim 15, wherein the replicon comprises a cyclization sequence of SEQ ID NO:3.

20. The method of claim 12, wherein the mutant flavivirus genome comprises an altered C-prM junction sequence of SEQ ID NO:4 and/or SEQ ID NO:5.

21. The replication-deficient pseudoinfectious virus of claim 1, wherein the mutant flavivirus genome is a dengue virus genome.

22. The host cell of claim 7, wherein the mutant flavivirus genome is a dengue virus genome.

23. The cell culture system of claim 8, wherein the mutant flavivirus genome is a dengue virus genome.

24. The method of claim 12, wherein the flavivirus is dengue virus.

* * * * *

SEQUENCE LISTING

```
<160> NUMBER OF SEQ ID NOS: 42

<210> SEQ ID NO 1
<211> LENGTH: 423
<212> TYPE: DNA
<213> ORGANISM: artificial sequence
<220> FEATURE:
<223> OTHER INFORMATION: synthetic polynucleotide

<400> SEQUENCE: 1
```

```
atgagcggcc ggaaggctca gggcaagacc ctgggcgtga acatggtgag gcgcggcgtg    60
cgcagcctct ccaacaagat caagcagaag accaagcaga tcggcaacag acccggaccg   120
agccggggcg tccaggggtt catcttcttc ttcctgttca acatcctcac aggtaagaag   180
atcacggctc acctgaagag gctctggaag atgctggacc ctcgccaggg gctcgcggtg   240
ctcagaaagg tgaagcgggt cgtcgcctcc ctgatgcgcg gcctgtcctc tcgcaagagg   300
cgctcccacg atgtgctcac cgtccaattc ctcattctgg gaatgctgct gatgactggc   360
ggcgtgaccc tggtgcgcaa gaaccgctgg ctgctgctga atgtgaccag tgaggacctc   420
ggg                                                                 423

<210> SEQ ID NO 2
<211> LENGTH: 11
<212> TYPE: RNA
<213> ORGANISM: artificial sequence
<220> FEATURE:
<223> OTHER INFORMATION: synthetic polynucleotide

<400> SEQUENCE: 2
gucaauaugc u                                                         11

<210> SEQ ID NO 3
<211> LENGTH: 11
<212> TYPE: RNA
<213> ORGANISM: artificial sequence
<220> FEATURE:
<223> OTHER INFORMATION: synthetic polynucleotide

<400> SEQUENCE: 3
gugaacaugu u                                                         11

<210> SEQ ID NO 4
<211> LENGTH: 8
<212> TYPE: PRT
<213> ORGANISM: artificial sequence
<220> FEATURE:
<223> OTHER INFORMATION: synthetic peptide

<400> SEQUENCE: 4

Ser Val Gly Ala Val Thr Leu Ser
1               5

<210> SEQ ID NO 5
<211> LENGTH: 8
<212> TYPE: PRT
<213> ORGANISM: artificial sequence
<220> FEATURE:
<223> OTHER INFORMATION: synthetic peptide

<400> SEQUENCE: 5

Gln Lys Lys Arg Gly Gly Lys Thr
1               5

<210> SEQ ID NO 6
<211> LENGTH: 14295
<212> TYPE: DNA
<213> ORGANISM: artificial sequence
<220> FEATURE:
<223> OTHER INFORMATION: synthetic polynucleotide

<400> SEQUENCE: 6
gagtaaatcc tgtgtgctaa ttgaggtgca ttggtctgca aatcgagttg ctaggcaata    60
```

```
aacacatttg gattaatttt aatcgttcgt tgagcgatta gcagagaact gaccagaaca    120
tgtctggtcg taaagctcag ggaaaaaccc tgggcgtcaa tatggtacga cgaggagttc    180
gctccttgtc aaacaccatg gtgagcaagg gcgaggagct gttcaccggg gtggtgccca    240
tcctggtcga gctggacggc gacgtaaacg gccacaagtt cagcgtgtcc ggcgagggcg    300
agggcgatgc cacctacggc aagctgaccc tgaagttcat ctgcaccacc ggcaagctgc    360
ccgtgccctg gcccaccctc gtgaccaccc tgacctacgg cgtgcagtgc ttcagccgct    420
accccgacca catgaagcag cacgacttct tcaagtccgc catgcccgaa ggctacgtcc    480
aggagcgcac catcttcttc aaggacgacg gcaactacaa gacccgcgcc gaggtgaagt    540
tcgagggcga cacccktggtg aaccgcatcg agctgaaggg catcgacttc aaggaggacg    600
gcaacatcct ggggcacaag ctggagtaca actacaacag ccacaacgtc tatatcatgg    660
ccgacaagca gaagaacggc atcaaggtga acttcaagat ccgccacaac atcgaggacg    720
gcagcgtgca gctcgccgac cactaccagc agaacacccc catcggcgac ggccccgtgc    780
tgctgcccga caaccactac ctgagcaccc agtccgccct gagcaaagac cccaacgaga    840
agcgcgatca catggtcctg ctggagttcg tgaccgccgc cgggatcact ctcggcatgg    900
acgagctgta caagcttgga ttgtcctcaa ggaaacgccg ttcccatgat gttctgactg    960
tgcaattcct aattttggga atgctgttga tgacgggtgg agtgaccttg gtgcggaaaa   1020
acagatggtt gctcctaaat gtgacatctg aggacctcgg gaaaacattc tctgtgggca   1080
caggcaactg cacaacaaac attttggaag ccaagtactg gtgcccagac tcaatggaat   1140
acaactgtcc caatctcagt ccaagagagg agccagatga cattgattgc tggtgctatg   1200
gggtggaaaa cgttagagtc gcatatggta agtgtgactc agcaggcagg tctaggaggt   1260
caagaagggc cattgacttg cctacgcatg aaaaccatgg tttgaagacc cggcaagaaa   1320
aatggatgac tggaagaatg ggtgaaaggc aactccaaaa gattgagaga tggttcgtga   1380
ggaacccctt ttttgcagtg acggctctga ccattgccta ccttgtggga agcaacatga   1440
cgcaacgagt cgtgattgcc ctactggtct tggctgttgg tccggcctac tcagctcact   1500
gcattggaat tactgacagg gatttcattg aggggtgca tggaggaact tgggtttcag   1560
ctaccctgga gcaagacaag tgtgtcactg ttatggcccc tgacaagcct tcattggaca   1620
tctcactaga gacagtagcc attgatagac ctgctgaggt gaggaaagtg tgttacaatg   1680
cagttctcac tcatgtgaag attaatgaca agtgccccag cactggagag gcccacctag   1740
ctgaagagaa cgaaggggac aatgcgtgca agcgcactta ttctgataga ggctggggca   1800
atggctgtgg cctatttggg aaagggagca ttgtggcatg cgccaaattc acttgtgcca   1860
aatccatgag tttgtttgag gttgatcaga ccaaaattca gtatgtcatc agagcacaat   1920
tgcatgtagg ggccaagcag gaaaattgga ataccgacat taagactctc aagtttgatg   1980
ccctgtcagg ctcccaggaa gtcgagttca ttgggtatgg aaaagctaca ctggaatgcc   2040
aggtgcaaac tgcggtggac tttggtaaca gttacatcgc tgagatggaa acagagagct   2100
ggatagtgga cagacagtgg gcccaggact tgaccctgcc atggcagagt ggaagtggcg   2160
gggtgtggag agagatgcat catccttgtcg aatttgaacc tccgcatgcc gccactatca   2220
gagtactggc cctgggaaac caggaaggct ccttgaaaac agctcttact ggcgcaatga   2280
gggttacaaa ggacacaaat gacaacaacc tttacaaact acatggtgga catgtttctt   2340
gcagagtgaa attgtcagct ttgacactca aggggacatc ctacaaaata tgcactgaca   2400
aaatgttttt tgtcaagaac ccaactgaca ctggccatgg cactgttgtg atgcaggtga   2460
```

```
aagtgtcaaa aggagccccc tgcaggattc cagtgatagt agctgatgat cttacagcgg    2520
caatcaataa aggcattttg gttacagtta accccatcgc ctcaaccaat gatgatgaag    2580
tgctgattga ggtgaaccca ccttttggag acagctacat tatcgttggg agaggagatt    2640
cacgtctcac ttaccagtgg cacaaagagg gaagctcaat aggaaagttg ttcactcaga    2700
ccatgaaagg cgtggaacgc ctggccgtca tgggagacac cgcctgggat tcagctccg    2760 ctggagggtt cttcacttcg gttgggaaag gaattcatac ggtgtttggc tctgcctttc    2820 agggctatt tggcggcttg aactggataa caaaggtcat catggggcg gtacttatat    2880 gggttggcat caacacaaga aacatgacaa tgtccatgag catgatcttg gtaggagtga    2940
tcatgatgtt tttgtctcta ggagttgggg cggatcaagg atgcgccatc aactttggca    3000
agagagagct caagtgcgga gatggtatct tcatatttag agactctgat gactggctga    3060
acaagtactc atactatcca gaagatcctg tgaagcttgc atcaatagtg aaagcctctt    3120
ttgaagaagg gaagtgtggc ctaaattcag ttgactccct tgagcatgag atgtggagaa    3180
gcagggcaga tgagatcaat gccattttg aggaaaacga ggtggacatt tctgttgtcg    3240
tgcaggatcc aaagaatgtt taccagagag gaactcatcc attttccaga attcgggatg    3300
gtctgcagta tggttggaag acttggggta agaaccttgt gttctcccca gggaggaaga    3360
atggaagctt catcatagat ggaaagtcca ggaaagaatg cccgttttca aaccgggtct    3420
ggaattcttt ccagatagag gagtttggga cgggagtgtt caccacacgc gtgtacatgg    3480
acgcagtctt tgaatacacc atagactgcg atggatctat cttgggtgca gcggtgaacg    3540
gaaaaaagag tgcccatggc tctccaacat tttggatggg aagtcatgaa gtaaatggga    3600
catggatgat ccacaccttg gaggcattag attacaagga gtgtgagtgg ccactgacac    3660
atacgattgg aacatcagtt gaagagagtg aaatgttcat gccgagatca atcggaggcc    3720
cagttagctc tcacaatcat atccctggat acaaggttca gacgaacgga ccttggatgc    3780
aggtaccact agaagtgaag agagaagctt gcccagggac tagcgtgatc attgatggca    3840
actgtgatgg acggggaaaa tcaaccagat ccaccacgga tagcgggaaa gttattcctg    3900
aatggtgttg ccgctcctgc acaatgccgc ctgtgagctt ccatggtagt gatgggtgtt    3960
ggtatcccat ggaaattagg ccaaggaaaa cgcatgaaag ccatctggtg cgctcctggg    4020
ttacagctgg agaaatacat gctgtccctt ttggtttggt gagcatgatg atagcaatgg    4080
aagtggtcct aaggaaaaga cagggaccaa agcaaatgtt ggttggagga gtagtgctct    4140
tgggagcaat gctggtcggg caagtaactc tccttgattt gctgaaactc acagtggctg    4200
tgggattgca tttccatgag atgaacaatg gaggagacgc catgtatatg gcgttgattg    4260
ctgccttttc aatcagacca gggctgctca tcggctttgg gctcaggacc ctatggagcc    4320
ctcgggaacg ccttgtgctg acccctaggag cagccatggt ggagattgcc ttgggtggcg    4380
tgatgggcgg cctgtggaag tatctaaatg cagtttctct ctgcatcctg acaataaatg    4440
ctgttgcttc taggaaagca tcaaatacca tcttgccct catggctctg ttgacacctg    4500
tcactatggc tgaggtgaga cttgccgcaa tgttcttttg tgccgtggtt atcataggg    4560 tccttcacca gaatttcaag gacacctcca tgcagaagac tatacctctg gtggccctca    4620
cactcacatc ttacctgggc ttgacacaac cttttttggg cctgtgtgca tttctggcaa    4680
cccgcatatt tgggcgaagg agtatcccag tgaatgaggc actcgcagca gctggtctag    4740
tgggagtgct ggcaggactg gcttttcagg agatggagaa cttccttggt ccgattgcag    4800
```

```
ttggaggact cctgatgatg ctggttagcg tggctgggag ggtggatggg ctagagctca      4860
agaagcttgg tgaagtttca tgggaagagg aggcggagat cagcgggagt tccgcccgct      4920
atgatgtggc actcagtgaa caaggggagt tcaagctgct ttctgaagag aaagtgccat      4980
gggaccaggt tgtgatgacc tcgctggcct tggttgtggc tgccctccat ccatttgctc      5040
ttctgctggt ccttgctggg tggctgtttc atgtcagggg agctaggaga agtggggatg      5100
tcttgtggga tattcccact cctaagatca tcgaggaatg tgaacatctg gaggatggga      5160
tttatggcat attccagtca accttcttgg gggcctccca gcgaggagtg ggagtggcac      5220 agggagggt gttccacaca atgtggcatg tcacaagagg agctttcctt gtcaggaatg      5280
gcaagaagtt gattccatct tgggcttcag taaaggaaga ccttgtcgcc tatggtggct      5340
catggaagtt ggaaggcaga tgggatggag aggaagaggt ccagttgatc gcggctgttc      5400
caggaaagaa cgtggtcaac gtccagacaa aaccgagctt gttcaaagtg aggaatgggg      5460
gagaaatcgg ggctgtcgct cttgactatc cgagtggcac ttcaggatct cctattgtta      5520
acaggaacgg agaggtgatt gggctgtacg gcaatggcat ccttgtcggt gacaactcct      5580
tcgtgtccgc catatcccag actgaggtga aggaagaagg aaaggaggag ctccaagaga      5640
tcccgacaat gctaaagaaa ggaatgacaa ctgtccttga ttttcatcct ggagctggga      5700
agacaagacg tttcctccca cagatcttgg ccgagtgcgc acggagacgc ttgcgcactc      5760
ttgtgttggc ccccaccagg gttgttcttt ctgaaatgaa ggaggctttt cacggcctgg      5820
acgtgaaatt ccacacacag cttttccg ctcacggcag cgggagagaa gtcattgatg      5880
ccatgtgcca tgccacccta acttacagga tgttggaacc aactagggtt gttaactggg      5940
aagtgatcat tatggatgaa gcccattttt tggatccagc tagcatagcc gctagaggtt      6000
gggcagcgca cagagctagg gcaaatgaaa gtgcaacaat cttgatgaca gccacaccgc      6060
ctgggactag tgatgaattt ccacattcaa atggtgaaat agaagatgtt caaacggaca      6120
tacccagtga gccctggaac acagggcatg actggatcct agctgacaaa aggcccacgg      6180
catggttcct tccatccatc agagctgcaa atgtcatggc tgcctctttg cgtaaggctg      6240
gaaagagtgt ggtggtcctg aacaggaaaa cctttgagag agaataccc acgataaagc      6300 agaagaaacc tgactttata ttggccactg acatagctga aatgggagcc aacctttgcg      6360
tggagcgagt gctggattgc aggacggctt ttaagcctgt gcttgtggat gaagggagga      6420
aggtggcaat aaaagggcca cttcgtatct ccgcatcctc tgctgctcaa aggagggggc      6480
gcattgggag aaatcccaac agagatggag actcatacta ctattctgag cctacaagtg      6540
aaaataatgc ccaccacgtc tgctggttgg aggcctcaat gctcttggac aacatggagg      6600
tgaggggtgg aatggtcgcc ccactctatg gcgttgaagg aactaaaaca ccagtttccc      6660
ctggtgaaat gagactgagg gatgaccaga ggaaagtctt cagagaacta gtgaggaatt      6720
gtgacctgcc cgtttggctt tcgtggcaag tggccaaggc tggtttgaag acgaatgatc      6780
gtaagtggtg ttttgaaggc cctgaggaac atgagatctt gaatgacagc ggtgaaacag      6840
tgaagtgcag ggctcctgga ggagcaaaga agcctctgcg cccaaggtgg tgtgatgaaa      6900
gggtgtcatc tgaccagagt gcgctgtctg aatttattaa gtttgctgaa ggtaggaggg      6960
gagctgctga agtgctagtt gtgctgagtg aactccctga tttcctggct aaaaaaggtg      7020
gagaggcaat ggataccatc agtgtgttcc tccactctga ggaaggctct agggcttacc      7080
gcaatgcact atcaatgatg cctgaggcaa tgacaatagt catgctgttt atactggctg      7140
gactactgac atcgggaatg gtcatctttt tcatgtctcc caaaggcatc agtagaatgt      7200
```

```
ctatggcgat gggcacaatg gccggctgtg gatatctcat gttccttgga ggcgtcaaac    7260
ccactcacat ctcctatgtc atgctcatat tctttgtcct gatggtggtt gtgatccccg    7320
agccagggca acaaaggtcc atccaagaca ccaagtggc  atacctcatt attggcatcc    7380
tgacgctggt ttcagcggtg gcagccaacg agctaggcat gctggagaaa accaaagagg    7440
acctctttgg gaagaagaac ttaattccat ctagtgcttc accctggagt tggccggatc    7500
ttgacctgaa gccaggagct gcctggacag tgtacgttgg cattgttaca atgctctctc    7560
caatgttgca ccactggatc aaagtcgaat atggcaacct gtctctgtct ggaatagccc    7620
agtcagcctc agtcctttct ttcatggaca agggatacc  attcatgaag atgaatatct    7680
cggtcataat gctgctggtc agtggctgga attcaataac agtgatgcct ctgctctgtg    7740
gcatagggtg cgccatgctc cactggtctc tcattttacc tggaatcaaa gcgcagcagt    7800
caaagcttgc acagagaagg gtgttccatg gcgttgccga gaaccctgtg gttgatggga    7860
atccaacagt tgacattgag gaagctcctg aaatgcctgc cctttatgag aagaaactgg    7920
ctctatatct ccttcttgct ctcagcctag cttctgttgc catgtgcaga acgcccttt    7980 cattggctga aggcattgtc ctagcatcag ctgccttagg gccgctcata gagggaaaca    8040
ccagccttct ttggaatgga cccatggctg tctccatgac aggagtcatg aggggaatc    8100 actatgcttt tgtgggagtc atgtacaatc tatggaagat gaaaactgga cgccggggga    8160
gcgcgaatgg aaaaactttg ggtgaagtct ggaagaggga actgaatctg ttggacaagc    8220
gacagtttga gttgtataaa aggaccgaca ttgtggaggt ggatcgtgat acggcacgca    8280
ggcatttggc cgaagggaag gtggacaccg gggtggcggt ctccaggggg accgcaaagt    8340
taaggtggtt ccatgagcgt ggctatgtca agctggaagg tagggtgatt gacctggggt    8400
gtggccgcgg aggctggtgt tactacgctg ctgcgcaaaa ggaagtgagt ggggtcaaag    8460
gatttactct tggaagagac ggccatgaga acccatgaa  tgtgcaaagt ctgggatgga    8520
acatcatcac cttcaaggac aaaactgata tccaccgcct agaaccagtg aaatgtgaca    8580
cccttttgtg tgacattgga gagtcatcat cgtcatcggt cacagagggg gaaaggaccg    8640
tgagagttct tgatactgta gaaaaatggc tggcttgtgg ggttgacaac ttctgtgtga    8700
aggtgttagc tccatacatg ccagatgttc ttgagaaact ggaattgctc caaaggaggt    8760
ttggcggaac agtgatcagg aaccctctct ccaggaattc cactcatgaa atgtactacg    8820
tgtctggagc ccgcagcaat gtcacatta  ctgtgaacca acatcccgc  ctcctgatga    8880 ggagaatgag gcgtccaact ggaaaagtga ccctggaggc tgacgtcatc ctcccaattg    8940
ggacacgcag tgttgagaca gacaagggac ccctggacaa agaggccata aagaaaggg    9000 ttgagaggat aaaatctgag tacatgacct cttggtttta tgacaatgac aaccctaca    9060 ggacctggca ctactgtggc tcctatgtca caaaaacctc aggaagtgcg gcgagcatgg    9120
taaatggtgt tattaaaatt ctgacatatc catgggacag gatagaggag gtcacaagaa    9180
tggcaatgac tgacacaacc cctttggac  agcaaagagt gtttaaagaa aaagttgaca    9240
ccagagcaaa ggatccacca gcgggaacta ggaagatcat gaaagttgtc aacaggtggc    9300
tgttccgcca cctggccaga gaaaagaacc ccagactgtg cacaaaggaa gaatttattg    9360
caaaagtccg aagtcatgca gccattggag cttacctgga agaacaagaa cagtggaaga    9420
ctgccaatga ggctgtccaa gacccaaagt tctgggaact ggtggatgaa gaaaggaagc    9480
tgcaccaaca aggcaggtgt cggacttgtg tgtacaacat gatggggaaa agagagaaga    9540
```

-continued

```
agctgtcaga gtttgggaaa gcaaagggaa gccgtgccat atggtatatg tggctgggag    9600
cgcggtatct tgagtttgag gccctgggat tcctgaatga ggaccattgg gcttccaggg    9660
aaaactcagg aggaggagtg gaaggcattg gcttacaata cctaggatat gtgatcagag    9720
acctggctgc aatggatggt ggtggattct acgcggatga caccgctgga tgggacacgc    9780
gcatcacaga ggcagacctt gatgatgaac aggagatctt gaactacatg agcccacatc    9840
acaaaaaact ggcacaagca gtgatggaaa tgacatacaa gaacaaagtg gtgaaagtgt    9900
tgagaccagc cccaggaggg aaagcctaca tggatgtcat aagtcgacga gaccagagag    9960
gatccgggca ggtagtgact tatgctctga acaccatcac caacttgaaa gtccaattga   10020
tcagaatggc agaagcagag atggtgatac atcaccaaca tgttcaagat tgtgatgaat   10080
cagttctgac caggctggag gcatggctca ctgagcacgg atgtgacaga ctgaaggaga   10140
tggcggtgag tggagacgac tgtgtggtcc ggcccatcga tgacaggttc ggcctggccc   10200
tgtcccatct caacgccatg tccaaggtta gaaggacata tctgaatgg cagccatcaa    10260 aagggtggaa tgattgggag aatgtgccct tctgttccca ccacttccat gaactacagc   10320
tgaaggatgg caggaggatt gtggtgcctt gccgagaaca ggacgagctc attgggagag   10380
gaagggtgtc tccaggaaac ggctggatga tcaaggaaac agcttgcctc agcaaagcct   10440
atgccaacat gtggtcactg atgtatttc acaaaaggga catgaggcta ctgtcattgg    10500
ctgtttcctc agctgttccc acctcatggg ttccacaagg acgcacaaca tggtcgattc   10560
atgggaaagg ggagtggatg accacggaag acatgcttga ggtgtggaac agagtatgga   10620
taaccaacaa cccacacatg caggacaaga caatggtgaa aaaatggaga gatgtccctt   10680
atctaaccaa gagacaagac aagctgtgcg gatcactgat tggaatgacc aatagggcca   10740
cctgggcctc ccacatccat ttagtcatcc atcgtatccg aacgctgatt ggacaggaga   10800
aatacactga ctacctaaca gtcatggaca ggtattctgt ggatgctgac ctgcaactgg   10860
gtgagcttat ctgaaacacc atctaacagg aataaccggg atacaaacca cgggtggaga   10920
accggactcc ccacaacctg aaaccgggat ataaaccacg gctggagaac cggactccgc   10980
acttaaaatg aaacagaaac cgggataaaa actacggatg gagaaccgga ctccacacat   11040
tgagacagaa gaagttgtca gcccagaacc ccacacgagt tttgccactg ctaagctgtg   11100
aggcagtgca ggctgggaca gccgacctcc aggttgcgaa aaacctggtt tctgggacct   11160 cccacccag agtaaaaaga acggagcctc cgctaccacc ctcccacgtg gtggtagaaa    11220 gacgggtct agaggttaga ggagaccctc cagggaacaa atagtgggac catattgacg    11280
ccagggaaag accggagtgg ttctctgctt ttcctccaga ggtctgtgag cacagtttgc   11340
tcaagaataa gcagaccttt ggatgacaaa cacaaaacca ctgggtcggc atggcatctc   11400
cacctcctcg cggtccgacc tgggcatccg aaggaggacg cacgtccact cggatggcta   11460
agggagagcc acgagctcct cgacagatca taatcagcca taccacattt gtagaggttt   11520
tacttgcttt aaaaaacctc ccacacctcc ccctgaacct gaaacataaa atgaatgcaa   11580
ttgttgttgt taacttgttt attgcagctt ataatggtta caaataaagc aatagcatca   11640
caaatttcac aaataaagca ttttttttcac tgcattctag ttgtggtttg tccaaactca   11700
tcaagatctc gagcaagacg tttcccgttg aatatggctc ataacacccc ttgtattact   11760
gtttatgtaa gcagacagtt ttattgttca tgatgatata ttttatcttt gtgcaatgta   11820
acatcagaga ttttgagaca caacgtggct ttgttgaata aatcgaactt tgctgagtt    11880 gaaggatcag atcacgcatc ttcccgacaa cgcagaccgt tccgtggcaa agcaaaagtt   11940
```

```
caaaatcacc aactggtcca cctacaacaa agctctcatc aaccgtggct ccctcacttt    12000
ctggctggat gatgggcga ttcaggcctg gtatgagtca gcaacacctt cttcacgagg    12060
cagacctcag cgctagcgga gtgtatactg gcttactatg ttggcactga tgagggtgtc    12120
agtgaagtgc ttcatgtggc aggagaaaaa aggctgcacc ggtgcgtcag cagaatatgt    12180
gatacaggat atattccgct tcctcgctca ctgactcgct acgctcggtc gttcgactgc    12240
ggcgagcgga atggcttac gaacggggcg gagatttcct ggaagatgcc aggaagatac    12300
ttaacaggga agtgagaggg ccgcggcaaa gccgtttttc cataggctcc gcccccctga    12360
caagcatcac gaaatctgac gctcaaatca gtggtggcga aacccgacag gactataaag    12420
ataccaggcg tttcccctgg cggctccctc gtgcgctctc ctgttcctgc ctttcggttt    12480
accggtgtca ttccgctgtt atggccgcgt ttgtctcatt ccacgcctga cactcagttc    12540
cgggtaggca gttcgctcca agctggactg tatgcacgaa ccccccgttc agtccgaccg    12600
ctgcgcctta tccggtaact atcgtcttga gtccaacccg gaaagacatg caaaagcacc    12660
actggcagca gccactggta attgatttag aggagttagt cttgaagtca tgcgccggtt    12720
aaggctaaac tgaaaggaca agttttggtg actgcgctcc tccaagccag ttacctcggt    12780
tcaaagagtt ggtagctcag agaaccttcg aaaaaccgcc ctgcaaggcg ttttttcgt    12840 tttcagagca agagattacg cgcagaccaa aacgatctca agaagatcat cttattaagg    12900
ggtctgacgc tcagtggaac gaaaactcac gttaagggat tttggtcatg agattatcaa    12960
aaaggatctt cacctagatc cttttaaatt aaaaatgaag ttttaaatca atctaaagta    13020
tatatgagta aacttggtct gacagttacc aatgcttaat cagtgaggca cctatctcag    13080
cgatctgtct atttcgttca tccatagttg cctgactccc cgtcgtgtag ataactacga    13140
tacgggaggg cttaccatct ggccccagtg ctgcaatgat accgcgagac ccacgctcac    13200
cggctccaga tttatcagca ataaaccagc cagccggaag ggccgagcgc agaagtggtc    13260
ctgcaacttt atccgcctcc atccagtcta ttaattgttg ccgggaagct agagtaagta    13320
gttcgccagt taatagtttg cgcaacgttg ttgccattgc tgcaggcatc gtggtgtcac    13380
gctcgtcgtt tggtatggct tcattcagct ccggttccca acgatcaagg cgagttacat    13440
gatcccccat gttgtgcaaa aaagcggtta gctccttcgg tcctccgatc gttgtcagaa    13500
gtaagttggc cgcagtgtta tcactcatgg ttatggcagc actgcataat tctcttactg    13560
tcatgccatc cgtaagatgc ttttctgtga ctggtgagta ctcaaccaag tcattctgag    13620
aatagtgtat gcggcgaccg agttgctctt gcccggcgtc aacacgggat aataccgcgc    13680
cacatagcag aactttaaaa gtgctcatca ttggaaaacg ttcttcgggg cgaaaactct    13740
caaggatctt accgctgttg agatccagtt cgatgtaacc cactcgtgca cccaactgat    13800
cttcagcatc ttttactttc accagcgttt ctgggtgagc aaaaacagga aggcaaaatg    13860
ccgcaaaaaa gggaataagg gcgacacgga aatgttgaat actcatactc ttcctttttc    13920
aatattattg aagcatttat cagggttatt gtctcatgag cggatacata tttgaatgta    13980
tttagaaaaa taaacaaata ggggttccgc gcacatttcc ccgaaaagtg ccacctgacg    14040
tgtcgacgcg gccgctagcg atgaccctgc tgattggttc gctgaccatt tccggtgcg    14100 ggacggcgtt accagaaact cagaaggttc gtccaaccaa accgactctg acggcagttt    14160
acgagagaga tgatagggtc tgcttcagta agccagatgc tacacaatta ggcttgtaca    14220
tattgtcgtt agaacgcggc tacaattaat acataaccct atgtatcata cacatacgat    14280
```
ttaggtgaca ctata                                                     14295

<210> SEQ ID NO 7
<211> LENGTH: 10863
<212> TYPE: DNA
<213> ORGANISM: artificial sequence
<220> FEATURE:
<223> OTHER INFORMATION: synthetic polynucleotide

<400> SEQUENCE: 7

```
gatgggcggc gcatgagaga agcccagacc aattacctac ccaaaatgga gaaagttcac    60
gttgacatcg aggaagacag cccattcctc agagctttgc agcggagctt cccgcagttt   120
gaggtagaag ccaagcaggt cactgataat gaccatgcta atgccagagc gttttcgcat   180
ctggcttcaa aactgatcga aacggaggtg gacccatccg acacgatcct tgacattgga   240
agtgcgcccg cccgcagaat gtattctaag cacaagtatc attgtatctg tccgatgaga   300
tgtgcggaag atccggacag attgtataag tatgcaacta agctgaagaa aaactgtaag   360
gaaataactg ataaggaatt ggacaagaaa atgaaggagc tggccgccgt catgagcgac   420
cctgacctgg aaactgagac tatgtgcctc cacgacgacg agtcgtgtcg ctacgaaggg   480
caagtcgctg tttaccagga tgtatacgcg gttgacggac cgacaagtct ctatcaccaa   540
gccaataagg gagttagagt cgcctactgg ataggctttg acaccacccc ttttatgttt   600
aagaacttgg ctggagcata tccatcatac tctaccaact gggccgacga aaccgtgtta   660
acggctcgta acataggcct atgcagctct gacgttatgg agcggtcacg tagagggatg   720
tccattctta gaaagaagta tttgaaacca tccaacaatg ttctattctc tgttggctcg   780
accatctacc acgagaagag ggacttactg aggagctggc acctgccgtc tgtatttcac   840
ttacgtggca agcaaaatta cacatgtcgg tgtgagacta tagttagttg cgacgggtac   900
gtcgttaaaa gaatagctat cagtccaggc ctgtatggga agccttcagg ctatgctgct   960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta ccttttgccc  1200
gtagtggccc aggcatttgc taggtgggca aggaatatat aggaagatca agaagatgaa  1260
aggccactag gactacgaga tagacagtta gtcatggggt gttgttgggc ttttagaagg  1320
cacaagataa catctatttta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagccgt cacctctcat taccgccgag  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctgggccc ggctcagtgg agacacctcg tggcttgata  1680
aaggttacca gctacgatgg cgaggacaag atcggctctt acgctgtgct ttctccgcag  1740
gctgtactca agagtgaaaa attatcttgc atccaccctc tcgctgaaca agtcatagtg  1800
ataacacact ctggccgaaa agggcgttat gccgtggaac cataccatgg taaagtagtg  1860
gtgccagagg acatgcaat acccgtccag gactttcaag ctctgagtga aagtgccacc  1920
attgtgtaca acgaacgtga gttcgtaaac aggtacctgc accatattgc cacacatgga  1980
ggagcgctga acactgatga agaatattac aaaactgtca gcccagcga gcacgacggc  2040
```

```
gaatacctgt acgacatcga caggaaacag tgcgtcaaga aagaactagt cactgggcta    2100
gggctcacag gcgagctggt ggatcctccc ttccatgaat tcgcctacga gagtctgaga    2160
acacgaccag ccgctcctta ccaagtacca accataggg tgtatggcgt gccaggatca     2220
ggcaagtctg gcatcattaa aagcgcagtc accaaaaaag atctagtggt gagcgccaag    2280
aaagaaaact gtgcagaaat tataagggac gtcaagaaaa tgaaagggct ggacgtcaat    2340
gccagaactg tggactcagt gctcttgaat ggatgcaaac accccgtaga gaccctgtat    2400
attgacgaag cttttgcttg tcatgcaggt actctcagag cgctcatagc cattataaga    2460
cctaaaaagg cagtgctctg cggggatccc aaacagtgcg gttttttaa catgatgtgc      2520
ctgaaagtgc attttaacca cgagatttgc acacaagtct tccacaaaag catctctcgc    2580
cgttgcacta aatctgtgac ttcggtcgtc tcaaccttgt tttacgacaa aaaaatgaga    2640
acgacgaatc cgaaagagac taagattgtg attgacacta ccggcagtac caaacctaag    2700
caggacgatc tcattctcac ttgtttcaga gggtgggtga agcagttgca aatagattac    2760
aaaggcaacg aaataatgac ggcagctgcc tctcaagggc tgacccgtaa aggtgtgtat    2820
gccgttcggt acaaggtgaa tgaaaatcct ctgtacgcac ccacctcaga acatgtgaac    2880
gtcctactga cccgcacgga ggaccgcatc gtgtggaaaa cactagccgg cgacccatgg    2940
ataaaaacac tgactgccaa gtaccctggg aatttcactg ccacgataga ggagtggcaa    3000
gcagagcatg atgccatcat gaggcacatc ttggagagac cggaccctac cgacgtcttc    3060
cagaataagg caaacgtgtg ttgggccaag gctttagtgc cggtgctgaa gaccgctggc    3120
atagacatga ccactgaaca atggaacact gtggattatt ttgaaacgga caaagctcac    3180
tcagcagaga tagtattgaa ccaactatgc gtgaggttct ttggactcga tctggactcc    3240
ggtctatttt ctgcacccac tgttccgtta tccattagga ataatcactg ggataactcc    3300
ccgtcgccta acatgtacgg gctgaataaa gaagtggtcc gtcagctctc tcgcaggtac    3360
ccacaactgc ctcgggcagt tgccactgga agagtctatg acatgaacac tggtacactg    3420
cgcaattatg atccgcgcat aaacctagta cctgtaaaca gaagactgcc tcatgcttta    3480
gtcctccacc ataatgaaca cccacagagt gactttttctt cattcgtcag caaattgaag    3540
ggcagaactg tcctggtggt cggggaaaag ttgtccgtcc caggcaaaat ggttgactgg    3600
ttgtcagacc ggcctgaggc taccttcaga gctcggctgg atttaggcat cccaggtgat    3660
gtgcccaaat atgacataat atttgttaat gtgaggaccc catataaata ccatcactat    3720
cagcagtgtg aagaccatgc cattaagctt agcatgttga ccaagaaagc ttgtctgcat    3780
ctgaatcccg gcggaacctg tgtcagcata ggttatggtt acgctgacag ggccagcgaa    3840
agcatcattg tgctatagc gcggcagttc aagttttccc gggtatgcaa accgaaatcc     3900
tcacttgaag agacggaagt tctgtttgta ttcattgggt acgatcgcaa ggcccgtacg    3960
cacaatcctt acaagctttc atcaaccttg accaacattt atacaggttc cagactccac    4020
gaagccggat gtgcaccctc atatcatgtg gtgcgagggg atattgccac ggccaccgaa    4080
ggagtgatta taaatgctgc taacagcaaa ggacaacctg gcggagggt gtgcggagcg     4140
ctgtataaga aattcccgga aagcttcgat ttacagccga tcgaagtagg aaaagcgcga    4200
ctggtcaaag gtgcagctaa acatatcatt catgccgtag gaccaaactt caacaaagtt    4260
tcggaggttg aaggtgacaa acagttggca gaggcttatg agtccgctaa gattgtcaac    4320
gataacaatt acaagtcagt agcgattcca ctttgtccac cggcatcttt tccgggaaca    4380
```

```
aagatcgact aacccaatca ttgaaccatt tgctgacagc tttagacacc actgatgcag    4440
atgtagccat atactgcagg gacaagaaat gggaatgact ctcaaggaag cagtggctag    4500
gagagaagca gtggaggaga tatgcatatc cgacgactct tcagtgacag aacctgatgc    4560
agagctggtg agggtgcatc cgaagagttc tttggctgga aggaagggct acagcacaag    4620
cgatggcaaa actttctcat atttggaagg gaccaagttt caccaggcgg ccaaggatat    4680
agcagaaatt aatgccatgt ggcccgttgc aacggaggcc aatgagcagg tatgcatgta    4740
tatcctcgga gaaagcatga gcagtattag gtcgaaatgc cccgtcgaag agtcggaagc    4800
ctccacacca cctagcacgc tgccttgctt gtgcatccat gccatgactc cagaaagagt    4860
acagcgccta aaagcctcac gtccagaaca aattactgtg tgctcatcct ttccattgcc    4920
gaagtataga atcactggtg tgcagaagat ccaatgctcc cagcctatat tgttctcacc    4980
gaaagtgcct gcgtatattc atccaaggaa gtatctcgtg aaacaccac cggtagacga    5040 gactccggag ccatcggcag agaaccaatc cacagagggg acacctgaac aaccaccact    5100
tataaccgag gatgagacca ggactagaac gcctgagccg atcatcatcg aagaggaaga    5160
agaggatagc ataagtttgc tgtcagatgg cccgacccac caggtgctgc aagtcgaggc    5220
agacattcac gggccgccct ctgtatctag ctcatcctgg tccattcctc atgcatccga    5280
ctttgatgtg gacagtttat ccatacttga caccctggag ggagctagcg tgaccagcgg    5340
ggcaacgtca gccgagacta actcttactt cgcaaagagt atggagtttc tggcgcgacc    5400
ggtgcctgcg cctcgaacag tattcaggaa ccctccacat cccgctccgc gcacaagaac    5460
accgtcactt gcacccagca gggcctgctc gagaaccagc ctagtttcca ccccgccagg    5520
cgtgaatagg gtgatcacta gagaggagct cgaggcgctt accccgtcac gcactcctag    5580
caggtcggtc tcgagaacca gcctggtctc caacccgcca ggcgtaaata gggtgattac    5640
aagagaggag tttgaggcgt tcgtagcaca acaacaatga cggtttgatg cgggtgcata    5700 catctttttcc tccgacaccg gtcaagggca tttacaacaa aaatcagtaa ggcaaacggt    5760
gctatccgaa gtggtgttgg agaggaccga attggagatt tcgtatgccc cgcgcctcga    5820
ccaagaaaaa gaagaattac tacgcaagaa attacagtta aatcccacac ctgctaacag    5880
aagcagatac cagtccagga aggtggagaa catgaaagcc ataacagcta gacgtattct    5940
gcaaggccta gggcattatt tgaaggcaga aggaaagtg gagtgctacc gaaccctgca    6000
tcctgttcct ttgtattcat ctagtgtgaa ccgtgccttt tcaagcccca aggtcgcagt    6060
ggaagcctgt aacgccatgt gaaagagaa cttttccgact gtggcttctt actgtattat    6120
tccagagtac gatgcctatt ggacatggt tgacggagct tcatgctgct tagacactgc    6180 cagttttttgc cctgcaaagc tgcgcagctt tccaaagaaa cactcctatt tggaacccac    6240
aatacgatcg gcagtgcctt cagcgatcca gaacacgctc cagaacgtcc tggcagctgc    6300
cacaaaaaga aattgcaatg tcacgcaaat gagagaattg cccgtattgg attcggcggc    6360
ctttaatgtg gaatgcttca agaaatatgc gtgtaataat gaatattggg aaacgtttaa    6420
agaaaacccc atcaggctta ctgaagaaaa cgtggtaaat tacattacca aattaaaagg    6480
accaaaagct gctgctcttt ttgcgaagac acataatttg aatatgttgc aggacatacc    6540
aatggacagg tttgtaatgg acttaaagag agacgtgaaa gtgactccag gaacaaaaca    6600
tactgaagaa cggcccaagg tacaggtgat ccaggctgcc gatccgctag caacagcgta    6660
tctgtgcgga atccaccgag agctggtag gagattaaat gcggtcctgc ttccgaacat    6720
tcatacactg tttgatatgt cggctgaaga ctttgacgct attatagccg agcacttcca    6780
```

-continued

```
gcctggggat tgtgttctgg aaactgacat cgcgtcgttt gataaaagtg aggacgacgc   6840
catggctctg accgcgttaa tgattctgga agacttaggt gtggacgcag agctgttgac   6900
gctgattgag gcggctttcg gcgaaatttc atcaatacat ttgcccacta aaactaaatt   6960
taaattcgga gccatgatga atctggaat gttcctcaca ctgtttgtga acacagtcat    7020
taacattgta atcgcaagca gagtgttgag agaacggcta accggatcac catgtgcagc   7080
attcattgga gatgacaata tcgtgaaagg agtcaaatcg acaaattaa tggcagacag    7140
gtgcgccacc tggttgaata tggaagtcaa gattatagat gctgtggtgg gcgagaaagc   7200
gccttatttc tgtggagggt ttattttgtg tgactccgtg accggcacag cgtgccgtgt   7260
ggcagacccc ctaaaaaggc tgtttaagct tggcaaacct ctggcagcag acgatgaaca   7320
tgatgatgac aggagaaggg cattgcatga agagtcaaca cgctggaacc gagtgggtat   7380
tctttcagag ctgtgcaagg cagtagaatc aaggtatgaa accgtaggaa cttccatcat   7440
agttatggcc atgactactc tagctagcag tgttaaatca ttcagctacc tgagaggggc   7500
ccctataact ctctacggct aacctgaatg gactacgaca tagtctagtc cgccaagtct   7560
agaccatgtc tggtcgtaaa gctcagggaa aaacccctggg cgtcaatatg gtacgacgag   7620
gagttcgctc cttgtcaaac aaaataaaac aaaaaacaaa acaaattgga aacagacctg   7680
gaccttcaag aggtgttcaa ggatttatct ttttcttttt gttcaacatt ttgactggaa   7740
aaagatcac agcccaccta agaggttgt ggaaaatgct ggacccaaga caaggcttgg    7800
ctgttctaag gaaagtcaag agagtggtgg ccagtttgat gagaggattg tcctcaagga   7860
aacgccgttc ccatgatgtt ctgactgtgc aattcctaat tttgggaatg ctgttgatga   7920
cgggtggata agggccccta taactctcta cggctaacct gaatggacta cgacatagtc   7980
tagtccgcca agtctagagc ttaccatgac cgagtacaag cccacggtgc gcctcgccac   8040
ccgcgacgac gtccccaggg ccgtacgcac cctcgccgcc gcgttcgccg actacccgc    8100
cacgcgccac accgtcgatc cggaccgcca catcgagcgg gtcaccgagc tgcaagaact   8160
cttcctcacg cgcgtcgggc tcgacatcgg caaggtgtgg gtcgcggacg acggcgccgc   8220
ggtggcggtc tggaccacgc cggagagcgt cgaagcgggg gcggtgttcg ccgagatcgg   8280
cccgcgcatg gccgagttga gcggttcccg gctggccgcg cagcaacaga tggaaggcct   8340
cctggcgccg caccggccca aggagcccgc gtggttcctg gccaccgtcg gcgtctcgcc   8400
cgaccaccag ggcaagggtc tgggcagcgc cgtcgtgctc cccggagtgg aggcggccga   8460
gcgcgccggg gtgccgcct tcctggagac ctccgcgccc cgcaacctcc ccttctacga    8520
gcggctcggc ttcaccgtca ccgccgacgt cgagtgcccg aaggaccgcg cgacctggtg   8580
catgacccgc aagcccggtg cctgacgccc gccccacgac ccgcagcgcc cgaccgaaag   8640
gagcgcacga ccccatgatc gctagaccat ggggtaccga gtatgttacg tgcaaaggtg   8700
attgtcaccc cccgaaagac catattgtga cacaccctca gtatcacgcc caaacattta   8760
cagccgcggt gtcaaaaacc gcgtggacgt ggttaacatc cctgctggga ggatcagccg   8820
taattattat aattggcttg gtgctggcta ctattgtggc catgtacgtg ctgaccaacc   8880
agaaacataa ttgaatacag cagcaattgg caagctgctt acatagaact cgcggcgatt   8940
ggcatgccgc cttaaaattt ttattttatt ttttcttttc ttttccgaat cggattttgt   9000
ttttaatatt tcaaaaaaaa aaaaaaaaaa aaaaaacgc gtcgagggga attaattctt    9060
gaagacgaaa gggccaggtg gcacttttcg gggaaatgtg cgcggaaccc ctatttgttt   9120
```

| | | | | |
|---|---|---|---|---|
| attttttctaa | atacattcaa | atatgtatcc | gctcatgaga | caataaccct gataaatgct | 9180 |
| tcaataatat | tgaaaaagga | agagtatgag | tattcaacat | ttccgtgtcg cccttattcc | 9240 |
| ctttttttgcg | gcattttgcc | ttcctgtttt | tgctcaccca | gaaacgctgg tgaaagtaaa | 9300 |
| agatgctgaa | gatcagttgg | gtgcacgagt | gggttacatc | gaactggatc tcaacagcgg | 9360 |
| taagatcctt | gagagttttc | gccccgaaga | acgttttcca | atgatgagca cttttaaagt | 9420 |
| tctgctatgt | ggcgcggtat | tatcccgtgt | tgacgccggg | caagagcaac tcggtcgccg | 9480 |
| catacactat | tctcagaatg | acttggttga | gtactcacca | gtcacagaaa agcatcttac | 9540 |
| ggatggcatg | acagtaagag | aattatgcag | tgctgccata | accatgagtg ataacactgc | 9600 |
| ggccaactta | cttctgacaa | cgatcggagg | accgaaggag | ctaaccgctt ttttgcacaa | 9660 |
| catgggggat | catgtaactc | gccttgatcg | ttgggaaccg | gagctgaatg aagccatacc | 9720 |
| aaacgacgag | cgtgacacca | cgatgcctgt | agcaatggca | acaacgttgc gcaaactatt | 9780 |
| aactggcgaa | ctacttactc | tagcttcccg | gcaacaatta | atagactgga tggaggcgga | 9840 |
| taaagttgca | ggaccacttc | tgcgctcggc | ccttccggct | ggctggttta ttgctgataa | 9900 |
| atctggagcc | ggtgagcgtg | ggtctcgcgg | tatcattgca | gcactggggc cagatggtaa | 9960 |
| gccctcccgt | atcgtagtta | tctacacgac | ggggagtcag | gcaactatgg atgaacgaaa | 10020 |
| tagacagatc | gctgagatag | gtgcctcact | gattaagcat | tggtaactgt cagaccaagt | 10080 |
| ttactcatat | atactttaga | ttgatttaaa | acttcatttt | taatttaaaa ggatctaggt | 10140 |
| gaagatcctt | tttgataatc | tcatgaccaa | aatcccttaa | cgtgagtttt cgttccactg | 10200 |
| agcgtcagac | cccgtagaaa | agatcaaagg | atcttcttga | gatcctttt ttctgcgcgt | 10260 |
| aatctgctgc | ttgcaaacaa | aaaaaccacc | gctaccagcg | gtggtttgtt tgccggatca | 10320 |
| agagctacca | actctttttc | cgaaggtaac | tggcttcagc | agagcgcaga taccaaatac | 10380 |
| tgtccttcta | gtgtagccgt | agttaggcca | ccacttcaag | aactctgtag caccgcctac | 10440 |
| atacctcgct | ctgctaatcc | tgttaccagt | ggctgctgcc | agtggcgata agtcgtgtct | 10500 |
| taccgggttg | gactcaagac | gatagttacc | ggataaggcg | cagcggtcgg gctgaacggg | 10560 |
| gggttcgtgc | acacagccca | gcttggagcg | aacgacctac | accgaactga gatacctaca | 10620 |
| gcgtgagcat | tgagaaagcg | ccacgcttcc | cgaagggaga | aaggcggaca ggtatccggt | 10680 |
| aagcggcagg | gtcggaacag | gagagcgcac | gagggagctt | ccagggggaa acgcctggta | 10740 |
| tctttatagt | cctgtcgggt | ttcgccacct | ctgacttgag | cgtcgatttt tgtgatgctc | 10800 |
| gtcaggggg | cggagcctat | ggaaaaacgc | cagcaacgcg | agctcgattt aggtgacact | 10860 |
| ata | | | | | 10863 |

<210> SEQ ID NO 8
<211> LENGTH: 10796
<212> TYPE: DNA
<213> ORGANISM: artificial sequence
<220> FEATURE:
<223> OTHER INFORMATION: synthetic polynucleotide

<400> SEQUENCE: 8

| | | | | |
|---|---|---|---|---|
| gatgggcggc | gcatgagaga | agcccagacc | aattacctac | ccaaaatgga gaaagttcac | 60 |
| gttgacatcg | aggaagacag | cccattcctc | agagctttgc | agcggagctt cccgcagttt | 120 |
| gaggtagaag | ccaagcaggt | cactgataat | gaccatgcta | atgccagagc gttttcgcat | 180 |
| ctggcttcaa | aactgatcga | aacggaggtg | gacccatccg | acacgatcct tgacattgga | 240 |
| agtgcgcccg | cccgcagaat | gtattctaag | cacaagtatc | attgtatctg tccgatgaga | 300 |

```
tgtgcggaag atccggacag attgtataag tatgcaacta agctgaagaa aaactgtaag    360
gaaataactg ataaggaatt ggacaagaaa atgaaggagc tggccgccgt catgagcgac    420
cctgacctgg aaactgagac tatgtgcctc cacgacgacg agtcgtgtcg ctacgaaggg    480
caagtcgctg tttaccagga tgtatacgcg gttgacggac cgacaagtct ctatcaccaa    540
gccaataagg gagttagagt cgcctactgg ataggctttg acaccacccc ttttatgttt    600
aagaacttgg ctggagcata tccatcatac tctaccaact gggccgacga aaccgtgtta    660
acggctcgta acataggcct atgcagctct gacgttatgg agcggtcacg tagagggatg    720
tccattctta gaaagaagta tttgaaacca tccaacaatg ttctattctc tgttggctcg    780
accatctacc acgagaagag ggacttactg aggagctggc acctgccgtc tgtatttcac    840
ttacgtggca agcaaaatta cacatgtcgg tgtgagacta tagttagttg cgacgggtac    900
gtcgttaaaa gaatagctat cagtccaggc ctgtatggga agccttcagg ctatgctgct    960
acgatgcacc gcgagggatt cttgtgctgc aaagtgacag acacattgaa cggggagagg   1020
gtctcttttc ccgtgtgcac gtatgtgcca gctacattgt gtgaccaaat gactggcata   1080
ctggcaacag atgtcagtgc ggacgacgcg caaaaactgc tggttgggct caaccagcgt   1140
atagtcgtca acggtcgcac ccagagaaac accaatacca tgaaaaatta cctttttgccc   1200 gtagtggccc aggcatttgc taggtgggca aggaatatat aggaagatca agaagatgaa   1260
aggccactag gactacgaga tagacagtta gtcatggggt gttgttgggc ttttagaagg   1320
cacaagataa catctatttta taagcgcccg gatacccaaa ccatcatcaa agtgaacagc   1380
gatttccact cattcgtgct gcccaggata ggcagtaaca cattggagat cgggctgaga   1440
acaagaatca ggaaaatgtt agaggagcac aaggagccgt cacctctcat taccgccgag   1500
gacgtacaag aagctaagtg cgcagccgat gaggctaagg aggtgcgtga agccgaggag   1560
ttgcgcgcag ctctaccacc tttggcagct gatgttgagg agcccactct ggaagccgat   1620
gtcgacttga tgttacaaga ggctggggcc ggctcagtgg agacacctcg tggcttgata   1680
aaggttacca gctacgatgg cgaggacaag atcggctctt acgctgtgct ttctccgcag   1740
gctgtactca agagtgaaaa attatcttgc atccaccctc tcgctgaaca agtcatagtg   1800
ataacacact ctggccgaaa agggcgttat gccgtggaac cataccatgg taaagtagtg   1860
gtgccagagg gacatgcaat acccgtccag gactttcaag ctctgagtga aagtgccacc   1920
attgtgtaca cgaacgtga gttcgtaaac aggtacctgc accatattgc cacacatgga   1980
ggagcgctga cactgatga agaatattac aaaactgtca agcccagcga gcacgacggc   2040
gaatacctgt acgacatcga caggaaacag tgcgtcaaga agaactagt cactgggcta   2100 gggctcacag gcgagctggt ggatcctccc ttccatgaat cgcctacga gagtctgaga   2160 acacgaccag ccgctcctta ccaagtacca accataggg tgtatggcgt gccaggatca   2220
ggcaagtctg gcatcattaa aagcgcagtc accaaaaaag atctagtggt gagcgccaag   2280
aaagaaaact gtgcagaaat tataagggac gtcaagaaaa tgaaagggct ggacgtcaat   2340
gccagaactg tggactcagt gctcttgaat ggatgcaaac accccgtaga gaccctgtat   2400
attgacgaag cttttgcttg tcatgcaggt actctcagag cgctcatagc cattataaga   2460
cctaaaaagg cagtgctctg cggggatccc aaacagtgcg gttttttaa catgatgtgc   2520 ctgaaagtgc attttaacca cgagatttgc acacaagtct tccacaaaag catctctcgc   2580
cgttgcacta aatctgtgac ttcggtcgtc tcaaccttgt tttacgacaa aaaaatgaga   2640
```

-continued

```
acgacgaatc cgaaagagac taagattgtg attgacacta ccggcagtac caaacctaag      2700
caggacgatc tcattctcac ttgtttcaga gggtgggtga agcagttgca aatagattac      2760
aaaggcaacg aaataatgac ggcagctgcc tctcaagggc tgacccgtaa aggtgtgtat      2820
gccgttcggt acaaggtgaa tgaaaatcct ctgtacgcac ccacctcaga acatgtgaac      2880
gtcctactga cccgcacgga ggaccgcatc gtgtggaaaa cactagccgg cgacccatgg      2940
ataaaaacac tgactgccaa gtaccctggg aatttcactg ccacgataga ggagtggcaa      3000
gcagagcatg atgccatcat gaggcacatc ttggagagac cggaccctac cgacgtcttc      3060
cagaataagg caaacgtgtg ttgggccaag gctttagtgc cggtgctgaa gaccgctggc      3120
atagacatga ccactgaaca atggaacact gtggattatt ttgaaacgga caaagctcac      3180
tcagcagaga tagtattgaa ccaactatgc gtgaggttct ttggactcga tctggactcc      3240
ggtctatttt ctgcacccac tgttccgtta tccattagga ataatcactg ggataactcc      3300
ccgtcgccta acatgtacgg gctgaataaa gaagtggtcc gtcagctctc tcgcaggtac      3360
ccacaactgc ctcgggcagt tgccactgga agagtctatg acatgaacac tggtacactg      3420
cgcaattatg atccgcgcat aaacctagta cctgtaaaca gaagactgcc tcatgcttta      3480
gtcctccacc ataatgaaca cccacagagt gactttttctt cattcgtcag caaattgaag      3540
ggcagaactg tcctggtggt cggggaaaag ttgtccgtcc caggcaaaat ggttgactgg      3600
ttgtcagacc ggcctgaggc taccttcaga gctcggctgg attaggcat cccaggtgat       3660
gtgcccaaat atgacataat atttgttaat gtgaggaccc catataaata ccatcactat      3720
cagcagtgtg aagaccatgc cattaagctt agcatgttga ccaagaaagc ttgtctgcat      3780
ctgaatcccg gcggaacctg tgtcagcata ggttatggtt acgctgacag ggccagcgaa      3840
agcatcattg tgctatagc gcggcagttc aagttttccc gggtatgcaa accgaaatcc      3900
tcacttgaag agacggaagt tctgtttgta ttcattgggt acgatcgcaa ggcccgtacg      3960
cacaatcctt acaagctttc atcaaccttg accaacattt atacaggttc cagactccac      4020
gaagccggat gtgcaccctc atatcatgtg gtgcgagggg atattgccac ggccaccgaa      4080
ggagtgatta taaatgctgc taacagcaaa ggacaacctg cgcgaggggt gtgcggagcg      4140
ctgtataaga aattcccgga aagcttcgat ttacagccga tcgaagtagg aaaagcgcga      4200
ctggtcaaag gtgcagctaa acatatcatt catgccgtag gaccaaactt caacaaagtt      4260
tcggaggttg aaggtgacaa acagttggca gaggcttatg agtccatcgc taagattgtc      4320
aacgataaca attacaagtc agtagcgatt ccactgttgt ccaccggcat ctttccggg       4380
aacaaagatc gactaaccca atcattgaac catttgctga cagctttaga caccactgat      4440
gcagatgtag ccatatactg cagggacaag aaatgggaaa tgactctcaa ggaagcagtg      4500
gctaggagag aagcagtgga ggagatatgg atatccgacg actcttcagt gacagaacct      4560
gatgcagagc tggtgagggt gcatccgaag agttctttgg ctggaaggaa gggctacagc      4620
acaagcgatg gcaaaacttt ctcatatttg gaagggacca gtttcacca ggcggccaag       4680
gatatagcag aaattaatgc catgtggccc gttgcaacgg aggccaatga gcaggtatgc      4740
atgtatatcc tcggagaaag catgagcagt attaggtcga atgccccgt cgaagagtcg        4800
gaagcctcca caccacctag cacgctgcct tgcttgtgca tccatgccat gactccagaa      4860
agagtacagc gcctaaaagc ctcacgtcca gaacaaatta ctgtgtgctc atcctttcca      4920
ttgccgaagt atagaatcac tggtgtgcag aagatccaat gctcccagcc tatattgttc      4980
tcaccgaaag tgcctgcgta tattcatcca aggaagtatc tcgtggaaac accaccggta      5040
```

```
gacgagactc cggagccatc ggcagagaac caatccacag aggggacacc tgaacaacca   5100
ccacttataa ccgaggatga gaccaggact agaacgcctg agccgatcat catcgaagag   5160
gaagaagagg atagcataag tttgctgtca gatggcccga cccaccaggt gctgcaagtc   5220
gaggcagaca ttcacgggcc gccctctgta tctagctcat cctggtccat tcctcatgca   5280
tccgactttg atgtggacag tttatccata cttgacaccc tggagggagc tagcgtgacc   5340
agcggggcaa cgtcagccga gactaactct tacttcgcaa agagtatgga gtttctggcg   5400
cgaccggtgc ctgcgcctcg aacagtattc aggaaccctc acatcccgc tccgcgcaca    5460
agaacaccgt cacttgcacc cagcagggcc tgctcgagaa ccagcctagt ttccaccccg   5520
ccaggcgtga atagggtgat cactagagag gagctcgagg cgcttacccc gtcacgcact   5580
cctagcaggt cggtctcgag aaccagcctg gtctccaacc cgccaggcgt aaatagggtg   5640
attacaagag aggagtttga ggcgttcgta gcacaacaac aatgacggtt tgatgcgggt   5700
gcatacatct tttcctccga caccggtcaa gggcatttac aacaaaaatc agtaaggcaa   5760
acggtgctat ccgaagtggt gttggagagg accgaattgg agatttcgta tgccccgcgc   5820
ctcgaccaag aaaaagaaga attactacgc aagaaattac agttaaatcc cacacctgct   5880
aacagaagca gataccagtc caggaaggtg agaacatga aagccataac agctagacgt    5940
attctgcaag gcctagggca ttatttgaag gcagaaggaa aagtggagtg ctaccgaacc   6000
ctgcatcctg ttcctttgta ttcatctagt gtgaaccgtg cctttttcaag ccccaaggtc   6060
gcagtggaag cctgtaacgc catgttgaaa gagaactttc cgactgtggc ttcttactgt   6120
attattccag agtacgatgc ctatttggac atggttgacg gagcttcatg ctgcttagac   6180
actgccagtt tttgccctgc aaagctgcgc agctttccaa agaaacactc ctatttggaa   6240
cccacaatac gatcggcagt gccttcagcg atccagaaca cgctccagaa cgtcctggca   6300
gctgccacaa aaagaaattg caatgtcacg caaatgagag aattgcccgt attggattcg   6360
gcggccttta atgtggaatg cttcaagaaa tatgcgtgta ataatgaata ttgggaaacg   6420
tttaaagaaa accccatcag gcttactgaa gaaaacgtgg taaattacat taccaaatta   6480
aaaggaccaa aagctgctgc tcttttttgcg aagacacata atttgaatat gttgcaggac   6540
ataccaatgg acaggtttgt aatggactta aagagagacg tgaaagtgac tccaggaaca   6600
aaacatactg aagaacggcc caaggtacag gtgatccagg ctgccgatcc gctagcaaca   6660
gcgtatctgt gcggaatcca ccgagagctg gttaggagat aaatgcggt cctgcttccg    6720
aacattcata cactgtttga tatgtcggct gaagactttg acgctattat agccgagcac   6780
ttccagcctg gggattgtgt tctggaaact gacatcgcgt cgtttgataa aagtgaggac   6840
gacgccatgg ctctgaccgc gttaatgatt ctggaagact aggtgtgga cgcagagctg    6900
ttgacgctga ttgaggcggc tttcggcgaa atttcatcaa tacatttgcc cactaaaact   6960
aaatttaaat tcgagccat gatgaaatct ggaatgttcc tcacactgtt tgtgaacaca    7020
gtcattaaca ttgtaatcgc aagcagagtg ttgagagaac ggctaaccgg atcaccatgt   7080
gcagcattca ttggagatga caatatcgtg aaaggagtca atcggacaa attaatggca    7140
gacaggtgcg ccacctggtt gaatatgaa gtcaagatta tagatgctgt ggtgggcgag    7200
aaagcgcctt atttctgtgg agggtttatt ttgtgtgact ccgtgaccgg cacagcgtgc   7260
cgtgtggcag acccccctaaa aaggctgttt aagcttggca aacctctggc agcagacgat   7320
gaacatgatg atgacaggag aagggcattg catgaagagt caacacgctg gaaccgagtg   7380
```

```
ggtattcttt cagagctgtg caaggcagta gaatcaaggt atgaaaccgt aggaacttcc      7440
atcatagtta tggccatgac tactctagct agcagtgtta aatcattcag ctacctgaga      7500
ggggccccta taactctcta cggctaacct gaatggacta cgacatagtc tagtccgcca      7560
aagaggtgtt caaggattta tcttttttctt tttgttcaac attttgactg gaaaaaagat     7620
cacagcccac ctaaagaggt tgtggaaaat gctggaccca agacaaggct tggctgttct      7680
aaggaaagtc aagagagtgg tggccagttt gatgagagga ttgtcctcaa ggaaacgccg      7740
ttcccatgat gttctgactg tgcaattcct aattttggga atgctgttga tgacgggtgg      7800
agtgaccttg gtgcggaaaa acagatggtt gctcctaaat gtgacatctg aggacctcgg      7860
gtaagggccc ctataactct ctacggctaa cctgaatgga ctacgacata gtctagtccg      7920
ccaagtctag agcttaccat gaccgagtac aagcccacgg tgcgcctcgc cacccgcgac      7980
gacgtcccca gggccgtacg caccctcgcc gccgcgttcg ccgactaccc cgccacgcgc      8040
cacaccgtcg atccggaccg ccacatcgag cgggtcaccg agctgcaaga actcttcctc      8100
acgcgcgtcg ggctcgacat cggcaaggtg tgggtcgcgg acgacggcgc cgcggtggcg      8160
gtctggacca cgccggagag cgtcgaagcg ggggcggtgt cgccgagat cggcccgcgc       8220 atggccgagt tgagcggttc ccggctggcc gcgcagcaac agatggaagg cctcctggcg      8280
ccgcaccggc caaggagcc cgcgtggttc ctggccaccg tcggcgtctc gcccgaccac        8340
cagggcaagg gtctgggcag cgccgtcgtg ctccccggag tggaggcggc cgagcgcgcc      8400
ggggtgcccg ccttcctgga gacctccgcg ccccgcaacc tccccttcta cgagcggctc      8460
ggcttcaccg tcaccgccga cgtcgagtgc ccgaaggacc gcgcgacctg gtgcatgacc      8520
cgcaagcccg gtgcctgacg cccgccccac gacccgcagc gcccgaccga aggagcgca       8580 cgaccccatg atcgctagac catggggtac cgagtatgtt acgtgcaaag gtgattgtca      8640
ccccccgaaa gaccatattg tgacacaccc tcagtatcac gcccaaacat ttacagccgc     8700
ggtgtcaaaa accgcgtgga cgtggttaac atccctgctg gaggatcagc cgtaattat       8760 tataattggc ttggtgctgg ctactattgt ggccatgtac gtgctgacca accagaaaca      8820
taattgaata cagcagcaat tggcaagctg cttacataga actcgcggcg attggcatgc      8880
cgccttaaaa ttttattttt attttttctt ttctttttccg aatcggattt tgttttttaat    8940 atttcaaaaa aaaaaaaaaa aaaaaaaaaa cgcgtcgagg ggaattaatt cttgaagacg      9000
aaagggccag gtggcacttt tcggggaaat gtgcgcggaa cccctatttg tttatttttc      9060
taaatacatt caaatatgta tccgctcatg agacaataac cctgataaat gcttcaataa      9120
tattgaaaaa ggaagagtat gagtattcaa catttccgtg tcgcccttat tcccttttttt    9180 gcggcatttt gccttcctgt ttttgctcac ccagaaacgc tggtgaaagt aaaagatgct     9240
gaagatcagt tgggtgcacg agtgggttac atcgaactgg atctcaacag cggtaagatc     9300
cttgagagtt ttcgccccga agaacgtttt ccaatgatga gcactttaaa agttctgcta     9360
tgtggcgcgg tattatcccg tgttgacgcc gggcaagagc aactcggtcg ccgcatacac     9420
tattctcaga atgacttggt tgagtactca ccagtcacag aaaagcatct tacggatggc     9480
atgacagtaa gagaattatg cagtgctgcc ataaccatga gtgataacac tgcggccaac     9540
ttacttctga caacgatcgg aggaccgaag gagctaaccg cttttttttgca caacatgggg   9600 gatcatgtaa ctcgccttga tcgttgggaa ccggagctga atgaagccat accaaacgac     9660
gagcgtgaca ccacgatgcc tgtagcaatg gcaacaacgt tgcgcaaact attaactggc     9720
gaactactta ctctagcttc ccggcaacaa ttaatagact ggatggaggc ggataaagtt     9780
```

```
gcaggaccac ttctgcgctc ggcccttccg gctggctggt ttattgctga taaatctgga    9840
gccggtgagc gtgggtctcg cggtatcatt gcagcactgg ggccagatgg taagccctcc    9900
cgtatcgtag ttatctacac gacggggagt caggcaacta tggatgaacg aaatagacag    9960
atcgctgaga taggtgcctc actgattaag cattggtaac tgtcagacca agtttactca    10020
tatatacttt agattgattt aaaacttcat ttttaattta aaaggatcta ggtgaagatc    10080 cttttttgata atctcatgac caaaatccct taacgtgagt tttcgttcca ctgagcgtca    10140
gaccccgtag aaaagatcaa aggatcttct tgagatcctt ttttctgcg cgtaatctgc    10200 tgcttgcaaa caaaaaaacc accgctacca gcggtggttt gtttgccgga tcaagagcta    10260
ccaactcttt ttccgaaggt aactggcttc agcagagcgc agataccaaa tactgtcctt    10320
ctagtgtagc cgtagttagg ccaccacttc aagaactctg tagcaccgcc tacatacctc    10380
gctctgctaa tcctgttacc agtggctgct gccagtggcg ataagtcgtg tcttaccggg    10440
ttggactcaa gacgatagtt accggataag gcgcagcggt cgggctgaac ggggggttcg    10500
tgcacacagc ccagcttgga gcgaacgacc tacaccgaac tgagatacct acagcgtgag    10560
cattgagaaa gcgccacgct tcccgaaggg agaaaggcgg acaggtatcc ggtaagcggc    10620
agggtcggaa caggagagcg cacgagggag cttccagggg gaaacgcctg gtatctttat    10680
agtcctgtcg ggtttcgcca cctctgactt gagcgtcgat ttttgtgatg ctcgtcaggg    10740
gggcggagcc tatggaaaaa cgccagcaac gcgagctcga tttaggtgac actata         10796

<210> SEQ ID NO 9
<211> LENGTH: 12839
<212> TYPE: DNA
<213> ORGANISM: artificial sequence
<220> FEATURE:
<223> OTHER INFORMATION: synthetic polynucleotide

<400> SEQUENCE: 9
gatgggcggc gcatgagaga agcccagacc aattacctac ccaaaatgga gaaagttcac       60
gttgacatcg aggaagacag cccattcctc agagctttgc agcggagctt cccgcagttt      120
gaggtagaag ccaagcaggt cactgataat gaccatgcta atgccagagc gttttcgcat      180
ctggcttcaa aactgatcga aacggaggtg gacccatccg acacgatcct tgacattgga      240
agtgcgcccg cccgcagaat gtattctaag cacaagtatc attgtatctg tccgatgaga      300
tgtgcggaag atccggacag attgtataag tatgcaacta agctgaagaa aaactgtaag      360
gaaataactg ataaggaatt ggacaagaaa atgaaggagc tggccgccgt catgagcgac      420
cctgacctgg aaactgagac tatgtgcctc cacgacgacg agtcgtgtcg ctacgaaggg      480
caagtcgctc tttaccagga tgtatacgcg gttgacggac cgacaagtct ctatcaccaa      540
gccaataagg gagttagagt cgcctactgg ataggctttg acaccacccc ttttatgttt      600
aagaacttgg ctggagcata tccatcatac tctaccaact gggccgacga aaccgtgtta      660
acggctcgta acataggcct atgcagctct gacgttatgg agcggtcacg tagagggatg      720
tccattctta gaaagaagta tttgaaacca tccaacaatg ttctattctc tgttggctcg      780
accatctacc acgagaagag ggacttactg aggagctggc acctgccgtc tgtatttcac      840
ttacgtggca gcaaaatta cacatgtcgg tgtgagacta gttagttg cgacgggtac      900 gtcgttaaaa gaatagctat cagtccaggc ctgtatggga agccttcagg ctatgctgct      960
acgatgcacc gcgagggatt cttgtgctgc aaagtgacag acacattgaa cggggagagg     1020
```

```
gtctcttttc cgtgtgcac gtatgtgcca gctacattgt gtgaccaaat gactggcata    1080
ctggcaacag atgtcagtgc ggacgacgcg caaaaactgc tggttgggct caaccagcgt    1140
atagtcgtca acggtcgcac ccagagaaac accaatacca tgaaaaatta ccttttgccc    1200
gtagtggccc aggcatttgc taggtgggca aaggaatata aggaagatca agaagatgaa    1260
aggccactag gactacgaga tagacagtta gtcatggggt gttgttgggc ttttagaagg    1320
cacaagataa catctattta aagcgcccg gatacccaaa ccatcatcaa agtgaacagc    1380
gatttccact cattcgtgct gcccaggata ggcagtaaca cattggagat cgggctgaga    1440
acaagaatca ggaaaatgtt agaggagcac aaggagccgt cacctctcat taccgccgag    1500
gacgtacaag aagctaagtg cgcagccgat gaggctaagg aggtgcgtga agccgaggag    1560
ttgcgcgcag ctctaccacc tttggcagct gatgttgagg agcccactct ggaagccgat    1620
gtcgacttga tgttacaaga ggctggggcc ggctcagtgg agacacctcg tggcttgata    1680
aaggttacca gctacgatgg cgaggacaag atcggctctt acgctgtgct ttctccgcag    1740
gctgtactca agagtgaaaa attatcttgc atccaccctc tcgctgaaca agtcatagtg    1800
ataacacact ctggccgaaa agggcgttat gccgtggaac cataccatgg taaagtagtg    1860
gtgccagagg gacatgcaat acccgtccag gactttcaag ctctgagtga aagtgccacc    1920
attgtgtaca acgaacgtga gttcgtaaac aggtacctgc accatattgc cacacatgga    1980
ggagcgctga acactgatga agaatattac aaaactgtca gcccagcga gcacgacggc    2040 gaatacctgt acgacatcga caggaaacag tgcgtcaaga agaactagt cactgggcta    2100 gggctcacag gcgagctggt ggatcctccc ttccatgaat cgcctacga gagtctgaga    2160 acacgaccag ccgctcctta ccaagtacca accataggg tgtatggcgt gccaggatca    2220
ggcaagtctg gcatcattaa aagcgcagtc accaaaaaag atctagtggt gagcgccaag    2280
aaagaaaact gtgcagaaat tataagggac gtcaagaaaa tgaagggct ggacgtcaat    2340 gccagaactg tggactcagt gctcttgaat ggatgcaaac accccgtaga gaccctgtat    2400
attgacgaag cttttgcttg tcatgcaggt actctcagag cgctcatagc cattataaga    2460
cctaaaaagg cagtgctctg cggggatccc aaacagtgcg gtttttttaa catgatgtgc    2520
ctgaaagtgc attttaacca cgagatttgc acacaagtct tccacaaaag catctctcgc    2580
cgttgcacta atctgtgac ttcggtcgtc caaccttgt tttacgacaa aaaaatgaga    2640
acgacgaatc cgaaagagac taagattgtg attgacacta ccggcagtac caaacctaag    2700
caggacgatc tcattctcac ttgtttcaga gggtgggtga agcagttgca aatagattac    2760
aaaggcaacg aaataatgac ggcagctgcc tctcaagggc tgacccgtaa aggtgtgtat    2820
gccgttcggt acaaggtgaa tgaaaatcct ctgtacgcac ccacctcaga acatgtgaac    2880
gtcctactga cccgcacgga ggaccgcatc gtgtggaaaa cactagccgg cgacccatgg    2940
ataaaaacac tgactgccaa gtaccctggg aatttcactg ccacgataga ggagtggcaa    3000
gcagagcatg atgccatcat gaggcacatc ttggagagac cggaccctac cgacgtcttc    3060
cagaataagg caaacgtgtg ttgggccaag gctttagtgc cggtgctgaa gaccgctggc    3120
atagacatga ccactgaaca atggaacact gtggattatt ttgaaacgga caaagctcac    3180
tcagcagaga tagtattgaa ccaactatgc gtgaggttct ttggactcga tctggactcc    3240
ggtctatttt ctgcacccac tgttccgtta tccattagga ataatcactg ggataactcc    3300
ccgtcgccta acatgtacgg gctgaataaa gaagtggtcc gtcagctctc tcgcaggtac    3360
ccacaactgc ctcgggcagt tgccactgga agagtctatg acatgaacac tggtacactg    3420
```

```
cgcaattatg atccgcgcat aaacctagta cctgtaaaca gaagactgcc tcatgcttta    3480
gtcctccacc ataatgaaca cccacagagt gacttttctt cattcgtcag caaattgaag    3540
ggcagaactg tcctggtggt cggggaaaag ttgtccgtcc caggcaaaat ggttgactgg    3600
ttgtcagacc ggcctgaggc taccttcaga gctcggctgg atttaggcat cccaggtgat    3660
gtgcccaaat atgacataat atttgttaat gtgaggaccc catataaata ccatcactat    3720
cagcagtgtg aagaccatgc cattaagctt agcatgttga ccaagaaagc ttgtctgcat    3780
ctgaatcccg gcggaacctg tgtcagcata ggttatggtt acgctgacag ggccagcgaa    3840
agcatcattg tgctatagc gcggcagttc aagttttccc gggtatgcaa accgaaatcc     3900
tcacttgaag agacggaagt tctgtttgta ttcattgggt acgatcgcaa ggcccgtacg    3960
cacaatcctt acaagctttc atcaaccttg accaacattt atacaggttc cagactccac    4020
gaagccggat gtgcaccctc atatcatgtg gtgcgagggg atattgccac ggccaccgaa    4080
ggagtgatta taaatgctgc taacagcaaa ggacaacctg cggagggggt gtgcggagcg    4140
ctgtataaga aattcccgga aagcttcgat ttacagccga tcgaagtagg aaaagcgcga    4200
ctggtcaaag gtgcagctaa acatatcatt catgccgtag gaccaaactt caacaaagtt    4260
tcggaggttg aaggtgacaa acagttggca gaggcttatg agtccatcgc taagattgtc    4320
aacgataaca attacaagtc agtagcgatt ccactgttgt ccaccggcat cttttccggg    4380
aacaaagatc gactaaccca atcattgaac catttgctga cagctttaga caccactgat    4440
gcagatgtag ccatatactg cagggacaag aaatgggaaa tgactctcaa ggaagcagtg    4500
gctaggagag aagcagtgga ggagatatgc atatccgacg actcttcagt gacagaacct    4560
gatgcagagc tggtgagggt gcatccgaag agttctttgg ctggaaggaa gggctacagc    4620
acaagcgatg gcaaaacttt ctcatatttg gaagggacca gtttcacca ggcggccaag     4680 gatatagcag aaattaatgc catgtggccc gttgcaacgg aggccaatga gcaggtatgc    4740
atgtatatcc tcggagaaag catgagcagt attaggtcga atgccccgt cgaagagtcg     4800 gaagcctcca caccacctag cacgctgcct tgcttgtgca tccatgccat gactccagaa    4860
agagtacagc gcctaaaagc ctcacgtcca gaacaaatta ctgtgtgctc atcctttcca    4920
ttgccgaagt atagaatcac tggtgtgcag aagatccaat gctcccagcc tatattgttc    4980
tcaccgaaag tgcctgcgta tattcatcca aggaagtatc tcgtggaaac accaccggta    5040
gacgagactc cggagccatc ggcagagaac caatccacag aggggacacc tgaacaacca    5100
ccacttataa ccgaggatga gaccaggact agaacgcctg agccgatcat catcgaagag    5160
gaagaagagg atagcataag tttgctgtca gatggcccga cccaccaggt gctgcaagtc    5220
gaggcagaca ttcacgggcc gccctctgta tctagctcat cctggtccat tcctcatgca    5280
tccgactttg atgtggacag tttatccata cttgacaccc tggagggagc tagcgtgacc    5340
agcggggcaa cgtcagccga gactaactct tacttcgcaa agagtatgga gtttctggcg    5400
cgaccggtgc ctgcgcctcg aacagtattc aggaaccctc cacatccgc tccgcgcaca    5460 agaacaccgt cacttgcacc cagcagggcc tgctcgagaa ccagcctagt ttccaccccg    5520
ccaggcgtga ataggggtgat cactagagag gagctcgagg cgcttacccc gtcacgcact    5580
cctagcaggt cggtctcgag aaccagcctg tctccaacc cgccaggcgt aaatagggtg     5640 attcaagag aggagtttga ggcgttcgta gcacaacaac aatgacggtt tgatgcgggt     5700
gcatacatct tttcctccga caccggtcaa gggcatttac aacaaaaatc agtaaggcaa    5760
```

```
acggtgctat ccgaagtggt gttggagagg accgaattgg agatttcgta tgccccgcgc    5820
ctcgaccaag aaaagaaga attactacgc aagaaattac agttaaatcc cacacctgct    5880
aacagaagca gataccagtc caggaaggtg gagaacatga aagccataac agctagacgt    5940
attctgcaag gcctagggca ttatttgaag gcagaaggaa aagtggagtg ctaccgaacc    6000
ctgcatcctg ttcctttgta ttcatctagt gtgaaccgtg ccttttcaag ccccaaggtc    6060
gcagtggaag cctgtaacgc catgttgaaa gagaactttc cgactgtggc ttcttactgt    6120
attattccag agtacgatgc ctatttggac atggttgacg gagcttcatg ctgcttagac    6180
actgccagtt tttgccctgc aaagctgcgc agctttccaa agaaacactc ctatttggaa    6240
cccacaatac gatcggcagt gccttcagcg atccagaaca cgctccagaa cgtcctggca    6300
gctgccacaa aaagaaattg caatgtcacg caaatgagag aattgcccgt attggattcg    6360
gcggccttta atgtggaatg cttcaagaaa tatgcgtgta ataatgaata ttgggaaacg    6420
tttaaagaaa accccatcag gcttactgaa gaaaacgtgg taaattacat taccaaatta    6480
aaaggaccaa aagctgctgc tcttttttgcg aagacacata atttgaatat gttgcaggac    6540
ataccaatgg acaggtttgt aatggactta aagagagacg tgaaagtgac tccaggaaca    6600
aaacatactg aagaacggcc caaggtacag gtgatccagg ctgccgatcc gctagcaaca    6660
gcgtatctgt gcggaatcca ccgagagctg gttaggagat aaatgcggt cctgcttccg     6720
aacattcata cactgtttga tatgtcggct gaagactttg acgctattat agccgagcac    6780
ttccagcctg ggattgtgt tctggaaact gacatcgcgt cgtttgataa aagtgaggac     6840
gacgccatgg ctctgaccgc gttaatgatt ctggaagact taggtgtgga cgcagagctg    6900
ttgacgctga ttgaggcggc tttcggcgaa atttcatcaa tacatttgcc cactaaaact    6960
aaatttaaat tcgagccat gatgaaatct ggaatgttcc tcacactgtt tgtgaacaca     7020
gtcattaaca ttgtaatcgc aagcagagtg ttgagagaac ggctaaccgg atcaccatgt    7080
gcagcattca ttgagatga caatatcgtg aaaggagtca atcggacaa attaatggca      7140
gacaggtgcg ccacctggtt gaatatggaa gtcaagatta tagatgctgt ggtgggcgag    7200
aaagcgcctt atttctgtgg agggttttatt ttgtgtgact ccgtgaccgg cacagcgtgc    7260
cgtgtggcag accccctaaa aaggctgttt aagcttggca aacctctggc agcagacgat    7320
gaacatgatg atgacaggag aagggcattg catgaagagt caacacgctg gaaccgagtg    7380
ggtattcttt cagagctgtg caaggcagta gaatcaaggt atgaaaccgt aggaacttcc    7440
atcatagtta tggccatgac tactctagct agcagtgtta aatcattcag ctacctgaga    7500
ggggccccta taactctcta cggctaacct gaatggacta cgacatagtc tagtccgcca    7560
agtctagacc atgtctggtc gtaaagctca gggaaaaacc ctgggcgtca atatggtacg    7620
acgaggagtt cgctccttgt caaacaaaat aaaacaaaaa acaaaacaaa ttggaaacag    7680
acctggacct tcaagaggtg ttcaaggatt tatcttttc ttttttgttca acattttgac    7740
tggaaaaaag atcacagccc acctaaagag gttgtgaaa atgctggacc caagacaagg    7800
cttggctgtt ctaaggaaag tcaagagagt ggtggccagt tgatgagag gattgtcctc    7860
aaggaaacgc cgttcccatg atgttctgac tgtgcaattc ctaattttgg gaatgctgtt    7920
gatgacgggt ggagtgacct tggtgcggaa aaacagatgg ttgctcctaa atgtgacatc    7980
tgaggacctc gggaaaacat tctctgtggg cacaggcaac tgcacaacaa acattttgga    8040
agccaagtac tggtgcccag actcaatgga atacaactgt cccaatctca gtccaagaga    8100
ggagccagat gacattgatt gctggtgcta tgggtggaa aacgttagag tcgcatatgg    8160
```

```
taagtgtgac tcagcaggca ggtctaggag gtcaagaagg gccattgact tgcctacgca   8220
tgaaaaccat ggtttgaaga cccggcaaga aaaatggatg actggaagaa tgggtgaaag   8280
gcaactccaa aagattgaga gatggttcgt gaggaacccc ttttttgcag tgacggctct   8340
gaccattgcc taccttgtgg gaagcaacat gacgcaacga gtcgtgattg ccctactggt   8400
cttggctgtt ggtccggcct actcagctca ctgcattgga attactgaca gggatttcat   8460 tgaggggggtg catggaggaa cttgggtttc agctaccctg gagcaagaca agtgtgtcac   8520
tgttatggcc cctgacaagc cttcattgga catctcacta gagacagtag ccattgatag   8580
acctgctgag gtgaggaaag tgtgttacaa tgcagttctc actcatgtga agattaatga   8640
caagtgcccc agcactggag aggcccacct agctgaagag aacgaagggg acaatgcgtg   8700
caagcgcact tattctgata gaggctgggg caatggctgt ggcctatttg gaaagggag   8760 cattgtggca tgcgccaaat tcacttgtgc caaatccatg agtttgtttg aggttgatca   8820
gaccaaaatt cagtatgtca tcagagcaca attgcatgta ggggccaagc aggaaaattg   8880
gaataccgac attaagactc tcaagtttga tgccctgtca ggctcccagg aagtcgagtt   8940
cattgggtat ggaaaagcta cactggaatg ccaggtgcaa actgcggtgg actttggtaa   9000
cagttacatc gctgagatgg aaacagagag ctggatagtg gacagacagt gggcccagga   9060
cttgaccctg ccatggcaga gtggaagtgg cggggtgtgg agagagatgc atcatcttgt   9120
cgaatttgaa cctccgcatg ccgccactat cagagtactg gccctgggaa accaggaagg   9180
ctccttgaaa acagctctta ctggcgcaat gagggttaca aaggacacaa atgcaacaa   9240 cctttacaaa ctacatggtg gacatgtttc ttgcagagtg aaattgtcag ctttgacact   9300
caaggggaca tcctacaaaa tatgcactga caaaatgttt tttgtcaaga acccaactga   9360
cactggccat ggcactgttg tgatgcaggt gaaagtgtca aaaggagccc cctgcaggat   9420
tccagtgata gtagctgatg atcttacagc ggcaatcaat aaaggcattt tggttacagt   9480
taaccccatc gcctcaacca atgatgatga agtgctgatt gaggtgaacc caccttttgg   9540
agacagctac attatcgttg ggagaggaga ttcacgtctc acttaccagt ggcacaaaga   9600
gggaagctca ataggaaagt tgttcactca gaccatgaaa ggcgtggaac gcctggccgt   9660
catgggagac accgcctggg atttcagctc cgctggaggg ttcttcactt cggttgggaa   9720
aggaattcat acggtgtttg gctctgcctt tcaggggcta tttggcggct tgaactggat   9780
aacaaaggtc atcatggggg cggtacttat atgggttggc atcaacacaa gaaacatgac   9840
aatgtccatg agcatgatct tggtaggagt gatcatgatg tttttgtctc taggagttgg   9900
ggcgtaagcg gcccctataa ctctctacgg ctaacctgaa tggactacga catagtctag   9960
tccgccaagt ctagagctta ccatgaccga gtacaagccc acgtgcgcc tcgccacccg   10020 cgacgacgtc cccagggccg tacgcaccct cgccgccgcg ttcgccgact accccgccac   10080
gcgccacacc gtcgatccgg accgccacat cgagcgggtc accgagctgc aagaactctt   10140
cctcacgcgc gtcgggctcg acatcggcaa ggtgtgggtc gcggacgacg cgccgcggt   10200 ggcggtctgg accacgccgg agagcgtcga agcgggggcg gtgttcgccg agatcggccc   10260
gcgcatggcc gagttgagcg gttcccggct ggccgcgcag caacagatgg aaggcctcct   10320
ggcgccgcac cggcccaagg agccgcgtg gttcctggcc accgtcggcg tctcgcccga   10380
ccaccagggc aagggtctgg gcagcgccgt cgtgctcccc ggagtggagg cggccgagcg   10440
cgccggggtg cccgccttcc tggagacctc cgcgccccgc aacctcccct tctacgagcg   10500
```

```
gctcggcttc accgtcaccg ccgacgtcga gtgcccgaag gaccgcgcga cctggtgcat    10560
gacccgcaag cccggtgcct gacgcccgcc ccacgacccg cagcgcccga ccgaaaggag    10620
cgcacgaccc catgatcgct agaccatggg gtaccgagta tgttacgtgc aaaggtgatt    10680 gtcaccccc gaaagaccat attgtgacac accctcagta tcacgcccaa acatttacag    10740
ccgcggtgtc aaaaaccgcg tggacgtggt taacatccct gctgggagga tcagccgtaa    10800
ttattataat tggcttggtg ctggctacta ttgtggccat gtacgtgctg accaaccaga    10860
aacataattg aatacagcag caattggcaa gctgcttaca tagaactcgc ggcgattggc    10920
atgccgcctt aaaattttta ttttattttt tcttttcttt tccgaatcgg attttgtttt    10980
taatatttca aaaaaaaaaa aaaaaaaaaa aaaacgcgtc gagggaatt aattcttgaa    11040 gacgaaaggg ccaggtggca cttttcgggg aaatgtgcgc ggaaccccta tttgtttatt    11100
tttctaaata cattcaaata tgtatccgct catgagacaa taaccctgat aaatgcttca    11160
ataatattga aaaggaaga gtatgagtat tcaacatttc cgtgtcgccc ttattccctt    11220
ttttgcggca ttttgccttc ctgttttgc tcacccagaa acgctggtga agtaaaaga    11280 tgctgaagat cagttgggtg cacgagtggg ttacatcgac tggatctcaa cagcggtaag    11340
atccttgaga gttttcgccc cgaagaacgt tttccaatga tgagcacttt taagttctg    11400 ctatgtggcg cggtattatc ccgtgttgac gccgggcaag agcaactcgg tcgccgcata    11460
cactattctc agaatgactt ggttgagtac tcaccagtca cagaaaagca tcttacggat    11520
ggcatgacag taagagaatt atgcagtgct gccataacca tgagtgataa cactgcggcc    11580
aacttacttc tgacaacgat cggaggaccg aaggagctaa ccgcttttt gcacaacatg    11640 ggggatcatg taactcgcct tgatcgttgg gaaccggagc tgaatgaagc cataccaaac    11700
gacgagcgtg acaccacgat gcctgtagca atggcaacaa cgttgcgcaa actattaact    11760
ggcgaactac ttactctagc ttcccggcaa caattaatag actggatgga ggcggataaa    11820
gttgcaggac cacttctgcg ctcggccctt ccggctggct ggtttattgc tgataaatct    11880
ggagccggtg agcgtgggtc tcgcggtatc attgcagcac tggggccaga tggtaagccc    11940
tcccgtatcg tagttatcta cacgacgggg agtcaggcaa ctatggatga acgaaataga    12000
cagatcgctg agataggtgc ctcactgatt aagcattggt aactgtcaga ccaagtttac    12060
tcatatatac tttagattga tttaaaactt catttttaat ttaaaaggat ctaggtgaag    12120 atccttttg ataatctcat gaccaaaatc ccttaacgtg agttttcgtt ccactgagcg    12180
tcagaccccg tagaaaagat caaaggatct tcttgagatc ctttttttct gcgcgtaatc    12240
tgctgcttgc aaacaaaaaa accaccgcta ccagcggtgg tttgtttgcc ggatcaagag    12300
ctaccaactc ttttttccgaa ggtaactggc ttcagcagag cgcagatacc aaatactgtc    12360
cttctagtgt agccgtagtt aggccaccac ttcaagaact ctgtagcacc gcctacatac    12420
ctcgctctgc taatcctgtt accagtggct gctgccagtg gcgataagtc gtgtcttacc    12480
gggttggact caagacgata gttaccggat aaggcgcagc ggtcgggctg aacggggggt    12540
tcgtgcacac agcccagctt ggagcgaacg acctacaccg aactgagata cctacagcgt    12600
gagcattgag aaagcgccac gcttcccgaa gggagaaagg cggacaggta tccggtaagc    12660
ggcagggtcg gaacaggaga gcgcacgagg gagcttccag ggggaaacgc ctggtatctt    12720
tatagtcctg tcgggtttcg ccacctctga cttgagcgtc gatttttgtg atgctcgtca    12780
ggggggcgga gcctatggaa aaacgccagc aacgcgagct cgatttaggt gacactata    12839
```

-continued

<210> SEQ ID NO 10
<211> LENGTH: 10926
<212> TYPE: DNA
<213> ORGANISM: artificial sequence
<220> FEATURE:
<223> OTHER INFORMATION: synthetic polynucleotide

<400> SEQUENCE: 10

| | | | | | |
|---|---|---|---|---|---|
| gatgggcggc | gcatgagaga | agcccagacc | aattacctac | ccaaaatgga | gaaagttcac | 60 |
| gttgacatcg | aggaagacag | cccattcctc | agagctttgc | agcggagctt | cccgcagttt | 120 |
| gaggtagaag | ccaagcaggt | cactgataat | gaccatgcta | atgccagagc | gttttcgcat | 180 |
| ctggcttcaa | aactgatcga | aacggaggtg | gacccatccg | acacgatcct | tgacattgga | 240 |
| agtgcgcccg | cccgcagaat | gtattctaag | cacaagtatc | attgtatctg | tccgatgaga | 300 |
| tgtgcggaaa | tccggacag | attgtataag | tatgcaacta | agctgaagaa | aaactgtaag | 360 |
| gaaataactg | ataaggaatt | ggacaagaaa | atgaaggagc | tggccgccgt | catgagcgac | 420 |
| cctgacctgg | aaactgagac | tatgtgcctc | cacgacgacg | agtcgtgtcg | ctacgaaggg | 480 |
| caagtcgctg | tttaccagga | tgtatacgcg | gttgacggac | cgacaagtct | ctatcaccaa | 540 |
| gccaataagg | gagttagagt | cgcctactgg | ataggctttg | acaccacccc | ttttatgttt | 600 |
| aagaacttgg | ctggagcata | tccatcatac | tctaccaact | gggccgacga | aaccgtgtta | 660 |
| acggctcgta | acataggcct | atgcagtctc | gacgttatgg | agcggtcacg | tagagggatg | 720 |
| tccattctta | gaaagaagta | tttgaaacca | tccaacaatg | ttctattctc | tgttggctcg | 780 |
| accatctacc | acgagaagag | ggacttactg | aggagctggc | acctgccgtc | tgtatttcac | 840 |
| ttacgtggca | agcaaaatta | cacatgtcgg | tgtgagacta | tagttagttg | cgacgggtac | 900 |
| gtcgttaaaa | gaatagctat | cagtccaggc | ctgtatggga | agccttcagg | ctatgctgct | 960 |
| acgatgcacc | gcgagggatt | cttgtgctgc | aaagtgacag | acacattgaa | cggggagagg | 1020 |
| gtctcttttc | ccgtgtgcac | gtatgtgcca | gctacattgt | gtgaccaaat | gactggcata | 1080 |
| ctggcaacag | atgtcagtgc | ggacgacgcg | caaaaactgc | tggttgggct | caaccagcgt | 1140 |
| atagtcgtca | acggtcgcac | ccagagaaac | accaatacca | tgaaaaatta | ccttttgccc | 1200 |
| gtagtggccc | aggcatttgc | taggtgggca | aggaatata | aggaagatca | agaagatgaa | 1260 |
| aggccactag | gactacgaga | tagacagtta | gtcatggggt | gttgttgggc | ttttagaagg | 1320 |
| cacaagataa | catctatta | taagcgcccg | gatacccaaa | ccatcatcaa | agtgaacagc | 1380 |
| gatttccact | cattcgtgct | gcccaggata | ggcagtaaca | cattggagat | cgggctgaga | 1440 |
| acaagaatca | ggaaaatgtt | agaggagcac | aaggagccgt | cacctctcat | taccgccgag | 1500 |
| gacgtacaag | aagctaagtg | cgcagccgat | gaggctaagg | aggtgcgtga | agccgaggag | 1560 |
| ttgcgcgcag | ctctaccacc | tttggcagct | gatgttgagg | agcccactct | ggaagccgat | 1620 |
| gtcgacttga | tgttacaaga | ggctgggcc | ggctcagtgg | agacacctcg | tggcttgata | 1680 |
| aaggttacca | gctacgatgg | cgaggacaag | atcggctctt | acgctgtgct | ttctccgcag | 1740 |
| gctgtactca | agagtgaaaa | attatcttgc | atccaccctc | tcgctgaaca | agtcatagtg | 1800 |
| ataacacact | ctggccgaaa | agggcgttat | gccgtggaac | cataccatgg | taaagtagtg | 1860 |
| gtgccagagg | gacatgcaat | acccgtccag | gactttcaag | ctctgagtga | aagtgccacc | 1920 |
| attgtgtaca | acgaacgtga | gttcgtaaac | aggtacctgc | accatattgc | cacacatgga | 1980 |
| ggagcgctga | acactgatga | agaatattac | aaaactgtca | gcccagcga | gcacgacggc | 2040 |
| gaatacctgt | acgacatcga | caggaaacag | tgcgtcaaga | aagaactagt | cactgggcta | 2100 |

```
gggctcacag gcgagctggt ggatcctccc ttccatgaat tcgcctacga gagtctgaga    2160
acacgaccag ccgctcctta ccaagtacca accataggg tgtatggcgt gccaggatca     2220
ggcaagtctg gcatcattaa aagcgcagtc accaaaaaag atctagtggt gagcgccaag    2280
aaagaaaact gtgcagaaat tataagggac gtcaagaaaa tgaaagggct ggacgtcaat    2340
gccagaactg tggactcagt gctcttgaat ggatgcaaac accccgtaga gaccctgtat    2400
attgacgaag cttttgcttg tcatgcaggt actctcagag cgctcatagc cattataaga    2460
cctaaaaagg cagtgctctg cggggatccc aaacagtgcg gttttttta catgatgtgc     2520 ctgaaagtgc attttaacca cgagatttgc acacaagtct tccacaaaag catctctcgc    2580
cgttgcacta atctgtgac ttcggtcgtc tcaaccttgt tttacgacaa aaaaatgaga      2640
acgacgaatc cgaaagagac taagattgtg attgacacta ccggcagtac caaacctaag    2700
caggacgatc tcattctcac ttgtttcaga gggtgggtga agcagttgca aatagattac    2760
aaaggcaacg aaataatgac ggcagctgcc tctcaagggc tgacccgtaa aggtgtgtat    2820
gccgttcggt acaaggtgaa tgaaaatcct ctgtacgcac ccacctcaga acatgtgaac    2880
gtcctactga cccgcacgga ggaccgcatc gtgtggaaaa cactagccgg cgacccatgg    2940
ataaaaacac tgactgccaa gtaccctggg aatttcactg ccacgataga ggagtggcaa    3000
gcagagcatg atgccatcat gaggcacatc ttggagagac cggaccctac cgacgtcttc    3060
cagaataagg caaacgtgtg ttgggccaag gctttagtgc cggtgctgaa gaccgctggc    3120
atagacatga ccactgaaca atggaacact gtggattatt ttgaaacgga caaagctcac    3180
tcagcagaga tagtattgaa ccaactatgc gtgaggttct ttggactcga tctggactcc    3240
ggtctatttt ctgcacccac tgttccgtta tccattagga ataatcactg ggataactcc    3300
ccgtcgccta acatgtacgg gctgaataaa gaagtggtcc gtcagctctc tcgcaggtac    3360
ccacaactgc ctcgggcagt tgccactgga agagtctatg acatgaacac tggtacactg    3420
cgcaattatg atccgcgcat aaacctagta cctgtaaaca gaagactgcc tcatgcttta    3480
gtcctccacc ataatgaaca cccacagagt gacttttctt cattcgtcag caaattgaag    3540
ggcagaactg tcctggtggt cggggaaaag ttgtccgtcc caggcaaaat ggttgactgg    3600
ttgtcagacc ggcctgaggc taccttcaga gctcggctgg atttaggcat cccaggtgat    3660
gtgcccaaat atgacataat atttgttaat gtgaggaccc catataaata ccatcactat    3720
cagcagtgtg aagaccatgc cattaagctt agcatgttga ccaagaaagc ttgtctgcat    3780
ctgaatcccg gcggaacctg tgtcagcata ggttatggtt acgctgacag ggccagcgaa    3840
agcatcattg gtgctatagc gcggcagttc aagttttccc gggtatgcaa accgaaatcc    3900
tcacttgaag agacggaagt tctgtttgta ttcattgggt acgatcgcaa ggcccgtacg    3960
cacaatcctt acaagctttc atcaaccttg accaacattt atacaggttc cagactccac    4020
gaagccggat gtgcaccctc atatcatgtg gtgcgagggg atattgccac ggccaccgaa    4080
ggagtgatta taaatgctgc taacagcaaa ggacaacctg gcgagggggt gtgcggagcg    4140
ctgtataaga aattcccgga aagcttcgat ttacagccga tcgaagtagg aaaagcgcga    4200
ctggtcaaag gtgcagctaa acatatcatt catgccgtag gaccaaactt caacaaagtt    4260
tcggaggttg aaggtgacaa acagttggca gaggcttatg agtccatcgc taagattgtc    4320
aacgataaca attacaagtc agtagcgatt ccactgttgt ccaccggcat ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
```

```
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacccct ggaggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gcttcaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa cccatcagg cttactgaag aaaacgtggt aaattacatt accaaattaa    6480
aaggaccaaa agctgctgct cttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
```

```
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gtctagacca tgagcggccg gaaggctcag ggcaagaccc tgggcgtgaa catggtgagg    7620
cgcggcgtgc gcagcctctc caacaagatc aagcagaaga ccaagcagat cggcaacaga    7680
cccgaccga gccggggcgt ccaggggttc atcttcttct tcctgttcaa catcctcaca    7740
ggtaagaaga tcacggctca cctgaagagg ctctggaaga tgctggaccc tcgccagggg    7800
ctcgcggtgc tcagaaaggt gaagcgggtc gtcgcctccc tgatgcgcgg cctgtcctct    7860
cgcaagaggc gctcccacga tgtgctcacc gtccaattcc tcattctgga atgctgctga    7920
tgactggcgg cgtgaccctg gtgcgcaaga accgctggct gctgctgaat gtgaccagtg    7980
aggacctcgg gtaagggccc ctataactct ctacggctaa cctgaatgga ctacgacata    8040
gtctagtccg ccaagtctag agcttaccat gaccgagtac aagcccacgg tgcgcctcgc    8100
cacccgcgac gacgtcccca gggccgtacg caccctcgcc gccgcgttcg ccgactaccc    8160
cgccacgcgc cacaccgtcg atccggaccg ccacatcgag cgggtcaccg agctgcaaga    8220
actcttcctc acgcgcgtcg ggctcgacat cggcaaggtg tgggtcgcgg acgacggcgc    8280
cgcggtggcg gtctggacca cgcccggagag cgtcgaagcg ggggcggtgt tcgccgagat    8340
cggcccgcgc atggccgagt tgagcggttc ccggctggcc gcgcagcaac agatggaagg    8400
cctcctggcg ccgcaccggc caaggagcc gcgtggttc ctggccaccg tcggcgtctc    8460
gcccgaccac cagggcaagg gtctgggcag cgccgtcgtg ctccccggag tggaggcggc    8520
cgagcgcgcg ggggtgcccg ccttcctgga gacctccgcg ccccgcaacc tcccttcta    8580
cgagcggctc ggcttcaccg tcaccgccga cgtcgaggtg cccgaaggac cgcgcacctg    8640
gtgcatgacc cgcaagcccg tgcctgacg cccgcccac gacccgcagc gcccgaccga    8700
aaggagcgca cgacccatg atcgctagac catggggtac cgagtatgtt acgtgcaaag    8760
gtgattgtca ccccccgaaa gaccatattg tgacacaccc tcagtatcac gcccaaacat    8820
ttacagccgc ggtgtcaaaa accgcgtgga cgtggttaac atccctgctg ggaggatcag    8880
ccgtaattat tataattggc ttggtgctgg ctactattgt ggccatgtac gtgctgacca    8940
accagaaaca taattgaata cagcagcaat tggcaagctg cttacataga actcgcggcg    9000
attggcatgc cgccttaaaa ttttatttt attttttctt ttcttttccg aatcggattt    9060
tgttttaat atttcaaaaa aaaaaaaaaa aaaaaaaaa cgcgtcgagg ggaattaatt    9120
cttgaagacg aaagggccag gtggcacttt cggggaaat gtgcgcggaa ccctatttg    9180
tttatttttc taaatacatt caaatatgta tccgctcatg agacaataac cctgataaat    9240
```

```
gcttcaataa tattgaaaaa ggaagagtat gagtattcaa catttccgtg tcgcccttat    9300
tccctttttt gcggcatttt gccttcctgt ttttgctcac ccagaaacgc tggtgaaagt    9360
aaaagatgct gaagatcagt tgggtgcacg agtgggttac atcgaactgg atctcaacag    9420
cggtaagatc cttgagagtt ttcgccccga agaacgtttt ccaatgatga gcacttttaa    9480
agttctgcta tgtggcgcgg tattatcccg tgttgacgcc gggcaagagc aactcggtcg    9540
ccgcatacac tattctcaga atgacttggt tgagtactca ccagtcacag aaaagcatct    9600
tacggatggc atgacagtaa gagaattatg cagtgctgcc ataaccatga gtgataacac    9660
tgcggccaac ttacttctga caacgatcgg aggaccgaag gagctaaccg cttttttgca    9720
caacatgggg gatcatgtaa ctcgccttga tcgttgggaa ccggagctga atgaagccat    9780
accaaacgac gagcgtgaca ccacgatgcc tgtagcaatg gcaacaacgt tgcgcaaact    9840
attaactggc gaactactta ctctagcttc ccggcaacaa ttaatagact ggatggaggc    9900
ggataaagtt gcaggaccac ttctgcgctc ggcccttccg gctggctggt ttattgctga    9960
taaatctgga gccggtgagc gtgggtctcg cggtatcatt gcagcactgg ggccagatgg    10020
taagccctcc cgtatcgtag ttatctacac gacggggagt caggcaacta tggatgaacg    10080
aaatagacag atcgctgaga taggtgcctc actgattaag cattggtaac tgtcagacca    10140
agtttactca tatatacttt agattgattt aaaacttcat ttttaattta aaaggatcta    10200
ggtgaagatc cttttgata atctcatgac caaaatccct taacgtgagt tttcgttcca    10260
ctgagcgtca gacccgtag aaaagatcaa aggatcttct tgagatcctt ttttctgcg    10320 cgtaatctgc tgcttgcaaa caaaaaaacc accgctacca gcggtggttt gtttgccgga    10380
tcaagagcta ccaactcttt ttccgaaggt aactggcttc agcagagcgc agataccaaa    10440
tactgtcctt ctagtgtagc cgtagttagg ccaccacttc aagaactctg tagcaccgcc    10500
tacatacctc gctctgctaa tcctgttacc agtggctgct gccagtggcg ataagtcgtg    10560
tcttaccggg ttggactcaa gacgatagtt accggataag gcgcagcggt cgggctgaac    10620
ggggggttcg tgcacacagc ccagcttgga gcgaacgacc tacaccgaac tgagatacct    10680
acagcgtgag cattgagaaa gcgccacgct tcccgaaggg agaaaggcgg acaggtatcc    10740
ggtaagcggc agggtcggaa caggagagcg cacgagggag cttccagggg gaaacgcctg    10800
gtatctttat agtcctgtcg ggtttcgcca cctctgactt gagcgtcgat ttttgtgatg    10860
ctcgtcaggg gggcggagcc tatggaaaaa cgccagcaac gcgagctcga tttaggtgac    10920
actata                                                              10926
```

<210> SEQ ID NO 11
<211> LENGTH: 12836
<212> TYPE: DNA
<213> ORGANISM: artificial
<220> FEATURE:
<223> OTHER INFORMATION: Synthetic polynucleotide

<400> SEQUENCE: 11

```
gatgggcggc gcatgagaga agcccagacc aattacctac ccaaaatgga gaaagttcac      60
gttgacatcg aggaagacag cccattcctc bagagctttg cagcggagct tcccgcagtt     120
tgaggtagaa gccaagcagg tcactgataa tgaccatgct aatgccagag cgttttcgca     180
tctggcttca aaactgatcg aaacggaggt ggacccatcc gacacgatcc ttgacattgg     240
aagtgcgccc gcccgcagaa tgtattctaa gcacaagtat cattgtatct gtccgatgag     300
```

```
atgtgcggaa gatccggaca gattgtataa gtatgcaact aagctgaaga aaaactgtaa   360
ggaaataact gataaggaat tggacaagaa aatgaaggag ctggccgccg tcatgagcga   420
ccctgacctg gaaactgaga ctatgtgcct ccacgacgac gagtcgtgtc gctacgaagg   480
gcaagtcgct gtttaccagg atgtatacgc ggttgacgga ccgacaagtc tctatcacca   540
agccaataag ggagttagag tcgcctactg gataggcttt gacaccaccc cttttatgtt   600
taagaacttg gctggagcat atccatcata ctctaccaac tgggccgacg aaaccgtgtt   660
aacggctcgt aacataggcc tatgcagctc tgacgttatg gagcggtcac gtagagggat   720
gtccattctt agaaagaagt atttgaaacc atccaacaat gttctattct ctgttggctc   780
gaccatctac cacgagaaga gggacttact gaggagctgg cacctgccgt ctgtatttca   840
cttacgtggc aagcaaaatt acacatgtcg gtgtgagact atagttagtt gcgacgggta   900
cgtcgttaaa agaatagcta tcagtccagg cctgtatggg aagccttcag gctatgctgc   960
tacgatgcac cgcgagggat tcttgtgctg caaagtgaca gacacattga acggggagag  1020
ggtctctttt cccgtgtgca cgtatgtgcc agctacattg tgtgaccaaa tgactggcat  1080
actggcaaca gatgtcagtg cggacgacgc gcaaaaactg ctggttgggc tcaaccagcg  1140
tatagtcgtc aacggtcgca cccagagaaa caccaatacc atgaaaaatt acctttgcc  1200 cgtagtggcc caggcatttg ctaggtgggc aaaggaatat aaggaagatc aagaagatga  1260
aaggccacta ggactacgag atagacagtt agtcatgggg tgttgttggg cttttagaag  1320
gcacaagata acatctattt ataagcgccc ggatacccaa accatcatca aagtgaacag  1380
cgatttccac tcattcgtgc tgcccaggat aggcagtaac acattggaga tcgggctgag  1440
aacaagaatc aggaaaatgt tagaggagca caaggagccg tcacctctca ttaccgccga  1500
ggacgtacaa gaagctaagt gcgcagccga tgaggctaag gaggtgcgtg aagccgagga  1560
gttgcgcgca gctctaccac ctttggcagc tgatgttgag gagcccactc tggaagccga  1620
tgtcgacttg atgttacaag aggctggggc cggctcagtg gagacacctc gtggcttgat  1680
aaaggttacc agctacgatg gcgaggacaa gatcggctct tacgctgtgc tttctccgca  1740
ggctgtactc aagagtgaaa aattatcttg catccaccct ctcgctgaac aagtcatagt  1800
gataacacac tctggccgaa aagggcgtta tgccgtggaa ccataccatg gtaaagtagt  1860
ggtgccagag ggacatgcaa tacccgtcca ggactttcaa gctctgagtg aaagtgccac  1920
cattgtgtac aacgaacgtg agttcgtaaa caggtacctg caccatattg ccacacatgg  1980
aggagcgctg aacactgatg aagaatatta caaaactgtc aagcccagcg agcacgacgg  2040
cgaatacctg tacgacatcg acaggaaaca gtgcgtcaag aaagaactag tcactgggct  2100
agggctcaca ggcgagctgg tggatcctcc cttccatgaa ttcgcctacg agagtctgag  2160
aacacgacca gccgctcctt accaagtacc aaccataggg gtgtatggcg tgccaggatc  2220
aggcaagtct ggcatcatta aaagcgcagt caccaaaaaa gatctagtgg tgagcgccaa  2280
gaaagaaaac tgtgcagaaa ttataaggga cgtcaagaaa atgaaaggc tggacgtcaa  2340 tgccagaact gtggactcag tgctcttgaa tggatgcaaa caccccgtag agaccctgta  2400
tattgacgaa gcttttgctt gtcatgcagg tactctcaga gcgctcatag ccattataag  2460
acctaaaaag gcagtgctct gcggggatcc caaacagtgc ggttttttta acatgatgtg  2520
cctgaaagtg cattttaacc acgagatttg cacacaagtc ttccacaaaa gcatctctcg  2580
ccgttgcact aaatctgtga cttcggtcgt ctcaaccttg ttttacgaca aaaaaatgag  2640
aacgacgaat ccgaaagaga ctaagattgt gattgacact accggcagta ccaaacctaa  2700
```

```
gcaggacgat ctcattctca cttgtttcag agggtgggtg aagcagttgc aaatagatta    2760
caaaggcaac gatatgacgg cagctgcctc tcaagggctg acccgtaaag gtgtgtatgc    2820
cgttcggtac aaggtgaatg aaaatcctct gtacgcaccc acctcagaac atgtgaacgt    2880
cctactgacc cgcacggagg accgcatcgt gtggaaaaca ctagccggcg acccatggat    2940
aaaaacactg actgccaagt accctgggaa tttcactgcc acgatagagg agtggcaagc    3000
agagcatgat gccatcatga ggcacatctt ggagagaccg gaccctaccg acgtcttcca    3060
gaataaggca acgtgtgtt gggccaaggc tttagtgccg gtgctgaaga ccgctggcat    3120
agacatgacc actgaacaat ggaacactgt ggattatttt gaaacggaca agctcactc    3180 agcagagata gtattgaacc aactatgcgt gaggttcttt ggactcgatc tggactccgg    3240 tctatttct gcacccactg ttccgttatc cattaggaat aatcactggg ataactcccc    3300
gtcgcctaac atgtacgggc tgaataaaga agtggtccgt cagctctctc gcaggtaccc    3360
acaactgcct cgggcagttg ccactggaag agtctatgac atgaacactg gtacactgcg    3420
caattatgat ccgcgcataa acctagtacc tgtaaacaga agactgcctc atgctttagt    3480
cctccaccat aatgaacacc cacagagtga ctttcttca ttcgtcagca aattgaaggg    3540
cagaactgtc ctggtggtcg gggaaaagtt gtccgtccca ggcaaaatgg ttgactggtt    3600
gtcagaccgg cctgaggcta ccttcagagc tcggctggat ttaggcatcc caggtgatgt    3660
gcccaaatat gacataatat tgttaatgt gaggacccca tataaatacc atcactatca    3720
gcagtgtgaa gaccatgcca ttaagcttag catgttgacc aagaaagctt gtctgcatct    3780
gaatcccggc ggaacctgtg tcagcatagg ttatggttac gctgacaggg ccagcgaaag    3840
catcattggt gctatagcgc ggcagttcaa gttttcccgg gtatgcaaac cgaaatcctc    3900
acttgaagag acggaagttc tgtttgtatt cattgggtac gatcgcaagg cccgtacgca    3960
caatccttac aagctttcat caaccttgac caacatttat acaggttcca gactccacga    4020
agccggatgt gcaccctcat atcatgtggt gcgagggat attgccacgg ccaccgaagg    4080
agtgattata aatgctgcta acagcaaagg acaacctggc ggaggggtgt gcggagcgct    4140
gtataagaaa ttcccggaaa gcttcgattt acagccgatc gaagtaggaa agcgcgact    4200 ggtcaaaggt gcagctaaac atatcattca tgccgtagga ccaaacttca caaagttc    4260 ggaggttgaa ggtgacaaac agttggcaga ggcttatgag tccatcgcta agattgtcaa    4320
cgataacaat tacaagtcag tagcgattcc actgttgtcc accggcatct tttccgggaa    4380
caaagatcga ctaacccaat cattgaacca tttgctgaca gctttagaca ccactgatgc    4440
agatgtagcc atatactgca gggacaagaa atgggaaatg actctcaagg aagcagtggc    4500
taggagagaa gcagtggagg agatatgcat atccgacgac tcttcagtga cagaacctga    4560
tgcagagctg gtgagggtgc atccgaagag ttctttggct ggaaggaagg gctacagcac    4620
aagcgatggc aaaactttct catatttgga agggaccaag tttcaccagg cggccaagga    4680
tatagcagaa attaatgcca tgtggcccgt tgcaacggag gccaatgagc aggtatgcat    4740
gtatatcctc ggagaaagca tgagcagtat taggtcgaaa tgccccgtcg aagagtcgga    4800
agcctccaca ccacctagca cgctgccttg cttgtgcatc catgccatga ctccagaaag    4860
agtacagcgc ctaaaagcct cacgtccaga acaaattact gtgtgctcat cctttccatt    4920
gccgaagtat agaatcactg gtgtgcagaa gatccaatgc tcccagccta tattgttctc    4980
accgaaagtg cctgcgtata ttcatccaag gaagtatctc gtggaaacac caccggtaga    5040
```

```
cgagactccg gagccatcgg cagagaacca atccacagag gggacacctg aacaaccacc    5100
acttataacc gaggatgaga ccaggactag aacgcctgag ccgatcatca tcgaagagga    5160
agaagaggat agcataagtt tgctgtcaga tggcccgacc caccaggtgc tgcaagtcga    5220
ggcagacatt cacgggccgc cctctgtatc tagctcatcc tggtccattc ctcatgcatc    5280
cgactttgat gtggacagtt tatccatact tgacaccctg gagggagcta gcgtgaccag    5340
cggggcaacg tcagccgaga ctaactctta cttcgcaaag agtatggagt ttctggcgcg    5400
accggtgcct gcgcctcgaa cagtattcag gaaccctcca catcccgctc cgcgcacaag    5460
aacaccgtca cttgcaccca gcagggcctg ctcgagaacc agcctagttt ccaccccgcc    5520
aggcgtgaat agggtgatca ctagagagga gctcgaggcg cttacccgt cacgcactcc    5580 tagcaggtcg gtctcgagaa ccagctggtc tccaacccgc caggcgtaaa tagggtgatt    5640
acaagagagg agtttgaggc gttcgtagca caacaacaat gacggtttga tgcgggtgca    5700
tacatctttt cctccgacac cggtcaaggg catttacaac aaaaatcagt aaggcaaacg    5760
gtgctatccg aagtggtgtt ggagaggacc gaattggaga tttcgtatgc cccgcgcctc    5820
gaccaagaaa aagaagaatt actacgcaag aaattacagt taaatcccac acctgctaac    5880
agaagcagat accagtccag gaaggtggag aacatgaaag ccataacagc tagacgtatt    5940
ctgcaaggcc tagggcatta tttgaaggca gaaggaaaag tggagtgcta ccgaaccctg    6000
catcctgttc ctttgtattc atctagtgtg aaccgtgcct tttcaagccc caaggtcgca    6060
gtggaagcct gtaacgccat gttgaaagag aactttccga ctgtggcttc ttactgtatt    6120
attccagagt acgatgccta tttgacatg gttgacggag cttcatgctg cttagacact    6180
gccagttttt gccctgcaaa gctgcgcagc tttccaaaga aacactccta tttggaaccc    6240
acaatacgat cggcagtgcc ttcagcgatc cagaacacgc tccagaacgt cctggcagct    6300
gccacaaaaa gaaattgcaa tgtcacgcaa atgagagaat tgcccgtatt ggattcggcg    6360
gcctttaatg tggaatgctt caagaaatat gcgtgtaata atgaatattg ggaaacgttt    6420
aaagaaaacc ccatcaggct tactgaagaa aacgtggtaa attacattac caaattaaaa    6480
ggaccaaaag ctgctgctct ttttgcgaag acacataatt tgaatatgtt gcaggacata    6540
ccaatggaca ggtttgtaat ggacttaaag agagacgtga aagtgactcc aggaacaaaa    6600
catactgaag aacggcccaa ggtacaggtg atccaggctg ccgatccgct agcaacagcg    6660
tatctgtgcg gaatccaccg agagctggtt aggagattaa atgcggtcct gcttccgaac    6720
attcatacac tgtttgatat gtcggctgaa gactttgacg ctattatagc cgagcacttc    6780
cagcctgggg attgtgttct ggaaactgac atcgcgtcgt ttgataaaag tgaggacgac    6840
gccatggctc tgaccgcgtt aatgattctg gaagacttag gtgtggacgc agagctgttg    6900
acgctgattg aggcggcttt cggcgaaatt tcatcaatac atttgcccac taaaactaaa    6960
tttaaattcg gagccatgat gaaatctgga atgttcctca cactgtttgt gaacacagtc    7020
attaacattg taatcgcaag cagagtgttg agagaacggc taaccggatc accatgtgca    7080
gcattcattg gagatgacaa tatcgtgaaa ggagtcaaat cggacaaatt aatggcagac    7140
aggtgcgcca cctggttgaa tatggaagtc aagattatag atgctgtggt gggcgagaaa    7200
gcgccttatt tctgtggagg gtttattttg tgtgactccg tgaccggcac agcgtgccgt    7260
gtggcagacc ccctaaaaag gctgtttaag cttggcaaac tctggcagc agacgatgaa    7320 catgatgatg acaggagaag ggcattgcat gaagagtcaa cacgctggaa ccgagtgggt    7380
attctttcag agctgtgcaa ggcagtagaa tcaaggtatg aaaccgtagg aacttccatc    7440
```

```
atagttatgg ccatgactac tctagctagc agtgttaaat cattcagcta cctgagaggg    7500
gccccuataa ctctctacgg ctaacctgaa tggactacga catagtctag tccgccaagt    7560
ctagaccatg agcggccgga aggctcaggg caagaccctg ggcgtgaaca tggtgaggcg    7620
cggcgtgcgc agcctctcca acaagatcaa gcagaagacc aagcagatcg caacagacc    7680 cggaccgagc cggggcgtcc aggggttcat cttcttcttc ctgttcaaca tcctcacagg    7740
taagaagatc acggctcacc tgaagaggct ctggaagatg ctggaccctc gccaggggct    7800
cgcggtgctc agaaaggtga agcgggtcgt cgcctccctg atgcgcggcc tgtcctctcg    7860
caagaggcgc tcccacgatg tgctcaccgt ccaattcctc attctgggaa tgctgttgat    7920
gacgggtgga gtgaccttgg tgcggaaaaa cagatggttg ctcctaaatg tgacatctga    7980
ggacctcggg aaaacattct ctgtgggcac aggcaactgc acaacaaaca tttggaagc    8040 caagtactgg tgcccagact caatggaata caactgtccc aatctcagtc aagagagga    8100 gccagatgac attgattgct ggtgctatgg ggtggaaaac gttagagtcg catatggtaa    8160
gtgtgactca gcaggcaggt ctaggaggtc aagaagggcc attgacttgc ctacgcatga    8220
aaaccatggt ttgaagaccc ggcaagaaaa atggatgact ggaagaatgg gtgaaaggca    8280
actccaaaag attgagagat ggttcgtgag gaacccctt tttgcagtga cggctctgac    8340
cattgcctac cttgtgggaa gcaacatgac gcaacgagtc gtgattgccc tactggtctt    8400
ggctgttggt ccggcctact cagctcactg cattggaatt actgacaggg atttcattga    8460
gggggtgcat ggaggaactt gggttcagc tacctggag caagacaagt gtgtcactgt    8520 tatgcccct gacaagcctt cattggacat ctcactagag acagtagcca ttgatagacc    8580
tgctgaggtg aggaaaagtgt gttacaatgc agttctcact catgtgaaga ttaatgacaa    8640
gtgccccagc actggagagg cccacctagc tgaagagaac gaaggggaca atgcgtgcaa    8700
gcgcacttat tctgatagag gctggggcaa tggctgtggc ctatttggga aaaggagcat    8760
tgtggcatgc gccaaattca cttgtgccaa atccatgagt ttgtttgagg ttgatcagac    8820
caaaattcag tatgtcatca gagcacaatt gcatgtaggg gccaagcagg aaaattggaa    8880
taccgacatt aagactctca gtttgatgc cctgtcaggc tcccaggaag tcgagttcat    8940
tgggtatgga aaagctacac tggaatgcca ggtgcaaact gcggtggact ttggtaacag    9000
ttacatcgct gagatggaaa cagagagctg gatagtggac agacagtggg cccaggactt    9060
gaccctgcca tggcagagtg gaagtggcgg ggtgtggaga gagatgcatc atcttgtcga    9120
atttgaacct ccgcatgccg ccactatcag agtactggcc ctgggaaacc aggaaggctc    9180
cttgaaaaca gctcttactg gcgcaatgag ggttacaaag gacacaaatg acaacaacct    9240
ttacaaacta catggtggac atgttcttg cagagtgaaa ttgtcagctt tgacactcaa    9300
ggggacatcc tacaaaatat gcactgacaa atgtttttt gtcaagaacc caactgacac    9360
tggccatggc actgttgtga tgcaggtgaa agtgtcaaaa ggagcccct gcaggattcc    9420 agtgatagta gctgatgatc ttacagcggc aatcaataaa ggcattttgg ttacagttaa    9480
ccccatcgcc tcaaccaatg atgatgaagt gctgattgag gtgaacccac cttttgaga    9540 cagctacatt atcgtgggga gaggagattc acgtctcact taccagtggc acaaagaggg    9600
aagctcaata ggaaagttgt tcactcagac catgaaaggc gtggaacgcc tggccgtcat    9660
gggagacacc gcctggggatt tcagctccgc tggagggttc ttcacttcgg ttgggaaagg    9720
aattcatacg gtgtttggct ctgcctttca ggggctattt ggcggcttga actggataac    9780
```

```
aaaggtcatc atgggggcgg tacttatatg ggttggcatc aacacaagaa acatgacaat   9840
gtccatgagc atgatcttgg taggagtgat catgatgttt ttgtctctag gagttggggc   9900
gtaagcggcc cctataactc tctacggcta acctgaatgg actacgacat agtctagtcc   9960
gccaagtcta gagcttacca tgaccgagta caagcccacg gtgcgcctcg ccacccgcga  10020
cgacgtcccc agggccgtac gcaccctcgc cgccgcgttc gccgactacc ccgccacgcg  10080
ccacaccgtc gatccggacc gccacatcga gcgggtcacc gagctgcaag aactcttcct  10140
cacgcgcgtc gggctcgaca tcggcaaggt gtgggtcgcg gacgacggcg ccgcggtggc  10200
ggtctggacc acgccggaga gcgtcgaagc ggggcggtg ttcgccgaga tcggcccgcg  10260
catggccgag ttgagcggtt cccggctggc cgcgcagcaa cagatggaag gcctcctggc  10320
gccgcaccgg cccaaggagc ccgcgtggtt cctggccacc gtcggcgtct cgcccgacca  10380
ccagggcaag ggtctgggca gcgccgtcgt gctccccgga gtggaggcgg ccgagcgcgc  10440
cggggtgccc gccttcctgg agacctccgc gccccgcaac ctccccttct acgagcggct  10500
cggcttcacc gtcaccgccg acgtcgaggt gcccgaagga ccgcgcacct gatgcatgac  10560
ccgcaagccc ggtgcctgac gcccgcccca cgacccgcag cgcccgaccg aaaggagcgc  10620
acgaccccat gatcgctaga ccatgggta ccgagtatgt tacgtgcaaa ggtgattgtc  10680
accccccgaa agaccatatt gtgacacacc ctcagtatca cgcccaaaca tttacagccg  10740
cggtgtcaaa aaccgcgtgg acgtggttaa catccctgct gggaggatca gccgtaatta  10800
ttataattgg cttggtgctg gctactattg tggccatgta cgtgctgacc aaccagaaac  10860
ataattgaat acagcagcaa ttggcaagct gcttacatag aactcgcggc gattgcatgc  10920
cgccttaaaa ttttatttt attttttctt ttcttttccg aatcggattt tgttttaat  10980 atttcaaaaa aaaaaaaaa aaaaaaaaa cgcgtcgagg ggaattaatt cttgaagacg  11040
aaagggccag gtggcacttt tcggggaaat gtgcgcggaa cccctatttg tttatttttc  11100
taaatacatt caaatatgta tccgctcatg agacaataac cctgataaat gcttcaataa  11160
tattgaaaaa ggaagagtat gagtattcaa catttccgtg tcgcccttat ccccttttt  11220 gcggcatttt gccttcctgt ttttgctcac ccagaaacgc tggtgaaagt aaaagatgct  11280
gaagatcagt tgggtgcacg agtgggttac atcgaactgg atctcaacag cggtaagatc  11340
cttgagagtt ttcgccccga agaacgtttt ccaatgatga gcacttttaa agttctgcta  11400
tgtggcgcgg tattatcccg tgttgacgcc gggcaagagc aactcggtcg ccgcatacac  11460
tattctcaga atgacttggt tgagtactca ccagtcacag aaaagcatct tacgatggc  11520 atgacagtaa gagaattatg cagtgctgcc ataaccatga gtgataacac tgcggccaac  11580
ttacttctga caacgatcgg aggaccgaag gagctaaccg cttttttgca caacatgggg  11640
gatcatgtaa ctcgccttga tcgttgggaa ccggagctga atgaagccat accaaacgac  11700
gagcgtgaca ccacgatgcc tgtagcaatg gcaacaacgt tgcgcaaact attaactggc  11760
gaactactta ctctagcttc ccggcaacaa ttaatagact ggatggaggc ggataaagtt  11820
gcaggaccac ttctgcgctc ggcccttccg gctggctggt ttattgctga taaatctgga  11880
gccggtgagc gtgggtctcg cggtatcatt gcagcactgg ggccagatgg taagccctcc  11940
cgtatcgtag ttatctacac gacggggagt caggcaacta tggatgaacg aaatagacag  12000
atcgctgaga taggtgcctc actgattaag cattggtaac tgtcagacca agtttactca  12060
tatatacttt agattgattt aaaacttcat ttttaattta aaaggatcta ggtgaagatc  12120
ctttttgata atctcatgac caaaatccct taacgtgagt tttcgttcca ctgagcgtca  12180
```

```
gaccccgtag aaaagatcaa aggatcttct tgagatcctt ttttctgcg cgtaatctgc    12240 tgcttgcaaa caaaaaaacc accgctacca gcggtggttt gtttgccgga tcaagagcta    12300
ccaactcttt ttccgaaggt aactggcttc agcagagcgc agataccaaa tactgtcctt    12360
ctagtgtagc cgtagttagg ccaccacttc aagaactctg tagcaccgcc tacatacctc    12420
gctctgctaa tcctgttacc agtggctgct gccagtggcg ataagtcgtg tcttaccggg    12480
ttggactcaa gacgatagtt accggataag gcgcagcggt cgggctgaac ggggggttcg    12540
tgcacacagc ccagcttgga gcgaacgacc tacaccgaac tgagatacct acagcgtgag    12600
cattgagaaa gcgccacgct tcccgaaggg agaaaggcgg acaggtatcc ggtaagcggc    12660
agggtcggaa caggagagcg cacgagggag cttccagggg gaaacgcctg gtatctttat    12720
agtcctgtcg ggtttcgcca cctctgactt gagcgtcgat ttttgtgatg ctcgtcaggg    12780
gggcggagcc tatggaaaaa cgccagcaac gcgagctcga tttaggtgac actata        12836

<210> SEQ ID NO 12
<211> LENGTH: 93
<212> TYPE: RNA
<213> ORGANISM: artificial sequence
<220> FEATURE:
<223> OTHER INFORMATION: synthetic polynucleotide

<400> SEQUENCE: 12
augagcaaaa agccuggugg accuggaaaa uccagagcag ugaacauguu gaagagaggc    60
augccaaggg uccucagucu gaucggccuu aag                                 93

<210> SEQ ID NO 13
<211> LENGTH: 21
<212> TYPE: RNA
<213> ORGANISM: artificial sequence
<220> FEATURE:
<223> OTHER INFORMATION: synthetic polynucleotide

<400> SEQUENCE: 13
ucaaaacaaa agaaaagaua a                                              21

<210> SEQ ID NO 14
<211> LENGTH: 31
<212> TYPE: PRT
<213> ORGANISM: artificial
<220> FEATURE:
<223> OTHER INFORMATION: synthetic peptide

<400> SEQUENCE: 14

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys
            20                  25                  30

<210> SEQ ID NO 15
<211> LENGTH: 6
<212> TYPE: PRT
<213> ORGANISM: artificial sequence
<220> FEATURE:
<223> OTHER INFORMATION: synthetic peptide

<400> SEQUENCE: 15

Ser Lys Gln Lys Lys Arg
1               5
```

```
<210> SEQ ID NO 16
<211> LENGTH: 90
<212> TYPE: RNA
<213> ORGANISM: artificial sequence
<220> FEATURE:
<223> OTHER INFORMATION: synthetic polynucleotide

<400> SEQUENCE: 16
augucuaaga aaccaggagg gcccggcaag agccgggcug ucaauaugcu aaaacgcgga     60
augccccgcg uguuguccuu gauuggacuu                                     90

<210> SEQ ID NO 17
<211> LENGTH: 33
<212> TYPE: PRT
<213> ORGANISM: artificial sequence
<220> FEATURE:
<223> OTHER INFORMATION: synthetic peptide

<400> SEQUENCE: 17

Met Ser Lys Lys Pro Gly Gly Pro Gly Gly Pro Gly Lys Ser Arg Ala
1               5                  10                  15

Val Asn Met Leu Lys Arg Gly Met Pro Arg Val Leu Ser Leu Ile Gly
            20                  25                  30

Leu

<210> SEQ ID NO 18
<211> LENGTH: 18
<212> TYPE: RNA
<213> ORGANISM: artificial sequence
<220> FEATURE:
<223> OTHER INFORMATION: synthetic polynucleotide

<400> SEQUENCE: 18
aagcaaaaga aaagagga                                                  18

<210> SEQ ID NO 19
<211> LENGTH: 6
<212> TYPE: PRT
<213> ORGANISM: artificial sequence
<220> FEATURE:
<223> OTHER INFORMATION: synthetic peptide

<400> SEQUENCE: 19

Lys Gln Lys Lys Arg Gly
1               5

<210> SEQ ID NO 20
<211> LENGTH: 11
<212> TYPE: RNA
<213> ORGANISM: artificial sequence
<220> FEATURE:
<223> OTHER INFORMATION: synthetic polynucleotide

<400> SEQUENCE: 20
cucaauaugc u                                                         11

<210> SEQ ID NO 21
<211> LENGTH: 11
<212> TYPE: RNA
<213> ORGANISM: artificial sequence
<220> FEATURE:
<223> OTHER INFORMATION: synthetic polynucleotide

<400> SEQUENCE: 21
gacaauaugc u                                                         11
```

<210> SEQ ID NO 22
<211> LENGTH: 11
<212> TYPE: RNA
<213> ORGANISM: artificial sequence
<220> FEATURE:
<223> OTHER INFORMATION: synthetic polynucleotide

<400> SEQUENCE: 22
gugaauaugc u                                                                11

<210> SEQ ID NO 23
<211> LENGTH: 11
<212> TYPE: RNA
<213> ORGANISM: artificial sequence
<220> FEATURE:
<223> OTHER INFORMATION: synthetic polynucleotide

<400> SEQUENCE: 23
gucuauaugc u                                                                11

<210> SEQ ID NO 24
<211> LENGTH: 11
<212> TYPE: RNA
<213> ORGANISM: artificial sequence
<220> FEATURE:
<223> OTHER INFORMATION: synthetic polynucleotide

<400> SEQUENCE: 24
gucauuaugc u                                                                11

<210> SEQ ID NO 25
<211> LENGTH: 11
<212> TYPE: RNA
<213> ORGANISM: artificial sequence
<220> FEATURE:
<223> OTHER INFORMATION: synthetic polynucleotide

<400> SEQUENCE: 25
gucaaaaugc u                                                                11

<210> SEQ ID NO 26
<211> LENGTH: 11
<212> TYPE: RNA
<213> ORGANISM: artificial sequence
<220> FEATURE:
<223> OTHER INFORMATION: synthetic polynucleotide

<400> SEQUENCE: 26
gucaauuugc u                                                                11

<210> SEQ ID NO 27
<211> LENGTH: 11
<212> TYPE: RNA
<213> ORGANISM: artificial sequence
<220> FEATURE:
<223> OTHER INFORMATION: synthetic polynucleotide

<400> SEQUENCE: 27
gucaauaucc u                                                                11

<210> SEQ ID NO 28
<211> LENGTH: 11
<212> TYPE: RNA
<213> ORGANISM: artificial sequence
<220> FEATURE:

```
<223> OTHER INFORMATION: synthetic polynucleotide

<400> SEQUENCE: 28
gucaauaugg u                                                            11

<210> SEQ ID NO 29
<211> LENGTH: 11
<212> TYPE: RNA
<213> ORGANISM: artificial sequence
<220> FEATURE:
<223> OTHER INFORMATION: synthetic polynucleotide

<400> SEQUENCE: 29
gucaauaugc a                                                            11

<210> SEQ ID NO 30
<211> LENGTH: 11
<212> TYPE: RNA
<213> ORGANISM: artificial sequence
<220> FEATURE:
<223> OTHER INFORMATION: synthetic polynucleotide

<400> SEQUENCE: 30
agcauauuga c                                                            11

<210> SEQ ID NO 31
<211> LENGTH: 11
<212> TYPE: RNA
<213> ORGANISM: artificial sequence
<220> FEATURE:
<223> OTHER INFORMATION: synthetic polynucleotide

<400> SEQUENCE: 31
agcauauuga g                                                            11

<210> SEQ ID NO 32
<211> LENGTH: 11
<212> TYPE: RNA
<213> ORGANISM: artificial sequence
<220> FEATURE:
<223> OTHER INFORMATION: synthetic polynucleotide

<400> SEQUENCE: 32
agcauauugu c                                                            11

<210> SEQ ID NO 33
<211> LENGTH: 11
<212> TYPE: RNA
<213> ORGANISM: artificial sequence
<220> FEATURE:
<223> OTHER INFORMATION: synthetic polynucleotide

<400> SEQUENCE: 33
agcauauuca c                                                            11

<210> SEQ ID NO 34
<211> LENGTH: 11
<212> TYPE: RNA
<213> ORGANISM: artificial sequence
<220> FEATURE:
<223> OTHER INFORMATION: synthetic polynucleotide

<400> SEQUENCE: 34
agcauauaga c                                                            11
```

```
<210> SEQ ID NO 35
<211> LENGTH: 11
<212> TYPE: RNA
<213> ORGANISM: artificial sequence
<220> FEATURE:
<223> OTHER INFORMATION: synthetic polynucleotide

<400> SEQUENCE: 35
agcauaauga c                                                          11

<210> SEQ ID NO 36
<211> LENGTH: 11
<212> TYPE: RNA
<213> ORGANISM: artificial sequence
<220> FEATURE:
<223> OTHER INFORMATION: synthetic polynucleotide

<400> SEQUENCE: 36
agcauuuuga c                                                          11

<210> SEQ ID NO 37
<211> LENGTH: 11
<212> TYPE: RNA
<213> ORGANISM: artificial sequence
<220> FEATURE:
<223> OTHER INFORMATION: synthetic polynucleotide

<400> SEQUENCE: 37
agcaaauuga c                                                          11

<210> SEQ ID NO 38
<211> LENGTH: 11
<212> TYPE: RNA
<213> ORGANISM: artificial sequence
<220> FEATURE:
<223> OTHER INFORMATION: synthetic polynucleotide

<400> SEQUENCE: 38
aggauauuga c                                                          11

<210> SEQ ID NO 39
<211> LENGTH: 11
<212> TYPE: RNA
<213> ORGANISM: artificial sequence
<220> FEATURE:
<223> OTHER INFORMATION: synthetic polynucleotide

<400> SEQUENCE: 39
accauauuga c                                                          11

<210> SEQ ID NO 40
<211> LENGTH: 11
<212> TYPE: RNA
<213> ORGANISM: artificial sequence
<220> FEATURE:
<223> OTHER INFORMATION: synthetic polynucleotide

<400> SEQUENCE: 40
ugcauauuga c                                                          11

<210> SEQ ID NO 41
<211> LENGTH: 11
<212> TYPE: RNA
<213> ORGANISM: artificial sequence
<220> FEATURE:
<223> OTHER INFORMATION: synthetic polynucleotide
```

```
<400> SEQUENCE: 41
gucuauuugc u                                                          11

<210> SEQ ID NO 42
<211> LENGTH: 11
<212> TYPE: RNA
<213> ORGANISM: artificial sequence
<220> FEATURE:
<223> OTHER INFORMATION: synthetic polynucleotide

<400> SEQUENCE: 42
agcaaauaga c                                                          11
```